US006214970B1

(12) United States Patent
Fuerst et al.

(10) Patent No.: US 6,214,970 B1
(45) Date of Patent: *Apr. 10, 2001

(54) HEPATITIS E VIRUS ANTIGENS AND USES THEREFOR

(75) Inventors: Thomas R. Fuerst, San Antonio, TX (US); C. Patrick McAtee, San Jose, CA (US); Patrice O. Yarbough, Union City, CA (US); Yi-Fan Zhang, Mountain View, CA (US)

(73) Assignee: Genelabs Technologies, Inc., Redwood City, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/542,634

(22) Filed: Oct. 13, 1995

Related U.S. Application Data

(63) Continuation-in-part of application No. 08/327,952, filed on Oct. 24, 1994, now abandoned, which is a continuation-in-part of application No. 08/240,049, filed on May 9, 1994, now Pat. No. 5,686,239, which is a continuation-in-part of application No. 07/876,941, filed on May 1, 1992, now Pat. No. 5,885,768, and a continuation-in-part of application No. 07/870,985, filed on Apr. 20, 1992, which is a continuation-in-part of application No. 07/822,335, filed on Jan. 17, 1992, now abandoned, which is a continuation-in-part of application No. 07/505,888, filed on Apr. 5, 1990, now abandoned, which is a continuation-in-part of application No. 07/420,921, filed on Oct. 13, 1989, now abandoned, which is a continuation-in-part of application No. 07/367,486, filed on Jun. 16, 1989, now abandoned, which is a continuation-in-part of application No. 07/336,672, filed on Apr. 11, 1989, now abandoned, which is a continuation-in-part of application No. 07/208,997, filed on Jun. 17, 1988, now abandoned.

(51) Int. Cl.[7] .................................................. C07K 14/08

(52) U.S. Cl. ............................................. 530/350; 435/5

(58) Field of Search .......................... 424/189.1; 530/806, 530/810, 826, 350; 536/23.72; 435/320.1, 5, 69.3

(56) References Cited

FOREIGN PATENT DOCUMENTS

| WO91/15603 | 10/1991 | (WO) . |
| WO93/14116 | 7/1993 | (WO) . |
| WO93/14208 | 7/1993 | (WO) . |
| WO94/06913 | 3/1994 | (WO) . |
| WO95/08632 | 3/1995 | (WO) . |

OTHER PUBLICATIONS

Bradley, D.W., et al., Enterically Transmitted Non–A, Non–B Hepatitis: Serial Passage of Disease in Cynomolgus Macaques and Tamarins and Recovery of Disease–Associated 27– to 34– nm Viruslike Particles, *Proc. Natl. Acad. Sci. USA* 84(17):6277–6281 (1987).

Dawson, G.J., et al., "Solid–Phase Enzyme–Linked Immunosorbent Assay for Hepatitis E Virus IgG and IgM Antibodies Utilizing Recombinant Antigens and Synthetic Peptides," *J. Virol. Methods* 38(1):175–186 (1992).

Huang, C.–C., et al., "Molecular Cloning and Sequencing of the Mexico Isolate of Hepatitis E Virus (HEV)," *Virology* 191(2):550–558 (1992).

Kaur, M., et al., "Human Linear B–Cell Epitopes Encoded by the Hepatitis E Virus Include Determinants in the RNA–Dependent RNA Polymerase," *Proc. Natl. Acad. Sci. USA* 89 (May):3855–3858 (1992).

Khudyakov, Y.E., et al., "Epitope Mapping in Proteins of Hepatitis E Virus," *Virology* 194(4):89–96 (1993).

Lok, A.S.F., et al., "Comparison of Reactivity of ORF 2 and ORF 3 HEV Antigens in IgG and IgM Anti–HEV Assays," *Int'l Symposium on Viral Hepatitis and Liver Disease* (Scientific Program and Abstract Volume), Abstract 694, pp. 262 (1993).

Purdy, M.A., et al., "Expression of a Hepatitis E Virus (HEV)–trpE Fusion Protein Containing Epitopes Recognized by Antibodies in Sera From Human Cases and Experimentally Infected Primates," *Archives of Virology* 123(3–4):335–349 (1992).

Purdy, M.A., et al., "Preliminary Evidence That a trpE–HEV Fusion Protein Protects Cynomolgus Macaques Against Challenge with Wild–Type Hepatitis E Virus (HEV)," *J. Med. Virol.* 41:90–94 (1993).

Reyes, G.R., et al., "Isolation of a cDNA from the Virus Responsible for Enterically Transmitted Non–A, Non–B Hepatitis," *Science* 247(4948):1335–1339 (1990).

Tam, A.W., et al., "Hepatitis E Virus (HEV): Molecular Cloning and Sequenceing of the Full–Length Viral Genome," *Virology* 185(1):120–132 (1991).

Tsarev, S.A., et al., "ELISA for Antibody to Hepatitis E Virus (HEV) Based on Complete Open–Reading Frame–2 Protein Expressed in Insect Cells: Identification of HEV Infection in Primates," *J. Infect. Dis.* 168(2):369–378 (1993).

Tsarev, S.A., et al., "Successful Passive and Active Immunization of Cynomolgus Monkeys Against Hepatitis E," *Proc. Natl. Acad. Sci.* 91(Oct):10198–101202 (1994).

(List continued on next page.)

*Primary Examiner*—Donna Wortman
(74) *Attorney, Agent, or Firm*—Gary R. Fabian; Charles K. Sholtz; Joanne R. Petithory

(57) ABSTRACT

Antigens are provided which are derived from the enterically transmitted non-A/non-B viral hepatitis agent, known as hepatitis E virus (HEV). The HEV antigens and in particular, soluble species of the capsid protein encoded by the carboxy terminal region of HEV ORF2, are immunoreactive with sera from individuals infected with HEV. In one embodiment, these antigens may be produced by a baculovirus expression vector and form virus-like particles (VLPs). The antigens are useful as diagnostic reagents in diagnostic methods and kits for determining infection of an individual with HEV. The antigens are also useful in vaccine compositions effective in methods for preventing HEV infection.

1 Claim, 18 Drawing Sheets

OTHER PUBLICATIONS

Tsarev, S.A., et al., "Infectivity Titration of a Prototype Strain of Hepatitis E Virus in Cynomolgus Monkeys," *J. Med. Vir.* 43:135–142 (1994).

Yarbough, P.O., et al., "Hepatitis E Virus: Identification of Type–Common Epitopes," *J. Virol.* 65:11(5790–5797 (1991).

Yarbough, P.O., et al., "Assay Development of Diagnostic Tests for Hepatitis E" in *Viral Hepatitis and Liver Disease* (Nishoka, K., et al., Eds.) Springer–Verlag, Tokyo, pp. 367–370 (1994).

He, J., et al., "Expression and Diagnostic Utility of Hepatitis E Virus Putative Structural Proteins Expressed in Insect Cells," *J. Clin. Microbiol.* 31(8) :2167–2173 (1993).

Boswell et al. "Sequence comparison and alignment: the measurement and interpretation of sequence similarity". Edited by Lesk, Computational Molecular Biology:Sources and Methods for sequence analysis, Oxford University Press, Oxford. pp. 161–178, 1988.*

* cited by examiner

```
            I-ORF3-->                                              I-ORF2-->
          5110v      5120v      5130v      5140v      5150v      5160v
-BURMA    TGGAATGAATAACATGTCTTTTGCTGCGCCCATGGGTTCGCGACCATGCGCCCTCGGCCT
           GAATGAATAACATGT   TTTGCTGCGCCCATGGGTTCGC ACCATGCGCCCT GGCCT
-MEXICO   CTGAATGAATAACATGTGGTTTGCTGCGCCCATGGGTTCGCCACCATGCGCCCTAGGCCT 5170v      5180v      5190v      5200v      5210v      5220v
-BURMA    ATTTTGTTGCTGCTCCTCATGTTTTTGCCTATGCTGCCCGCGCCACCGCCCGGTCAGCCG
           TTTTG TG TG TCCTC TGTTT TGCCTATG TGCCCGCGCCACCG CCGGTCAGCCG
-MEXICO   CTTTTGCTGTTGTTCCTCTTGTTTCTGCCTATGTTGCCCGCGCCACCGACCGGTCAGCCG 5230v      5240v      5250v      5260v      5270v      5280v
-BURMA    TCTGGCCGCCGTCGTGGGCGGCGCAGCGGCGGTTCCGGCGGTGGTTTCTGGGGTGACCGG
          TCTGGCCGCCGTCGTGGGCGGCGCAGCGGCGGT CCGGCGGTGGTTTCTGGGGTGACCGG
-MEXICO   TCTGGCCGCCGTCGTGGGCGGCGCAGCGGCGGTACCGGCGGTGGTTTCTGGGGTGACCGG 5290v      5300v      5310v      5320v      5330v      5340v
-BURMA    GTTGATTCTCAGCCCTTCGCAATCCCCTATATTCATCCAACCAACCCCTTCGCCCCCGAT
          GTTGATTCTCAGCCCTTCGCAATCCCCTATATTCATCCAACCAACCCCTT GCCCC GA
-MEXICO   GTTGATTCTCAGCCCTTCGCAATCCCCTATATTCATCCAACCAACCCCTTTGCCCCAGAC

I-406.4-2-->
          5350v      5360v      5370v      5380v      5390v      5400v
-BURMA    GTCACCGCTGCGGCCGGGGCTGGACCTCGTGTTCGCCAACCCGCCCGACCACTCGGCTCC
          GT  CCGCTGCG CCGGG CTGGACCTCG TTCGCCAACC GCCCG CCACT GGCTCC
-MEXICO   GTTGCCGCTGCGTCCGGGTCTGGACCTCGCCTTCGCCAACCAGCCCGGCCACTTGGCTCC 5410v      5420v      5430v      5440v      5450v      5460v
-BURMA    GCTTGGCGTGACCAGGCCCAGCGCCCCGCCGTTGCCCTCACGTCGTAGACCTACCACAGCT
           CTTGGCG GA CAGGCCCAGCGCCCC CCG TGCCTC CGTCG  GACCT CCACAGC
-MEXICO   ACTTGGCGAGATCAGGCCCAGCGCCCCTCCGCTGCCTCCCGTCGCCGACCTGCCACAGCC

<--406.4-2-I
            <-ORF3--I
          5470v      5480v      5490v      5500v      5510v      5520v
-BURMA    GGGGCCGCGCCGCTAACCGCGGTCGCTCCGGCCCATGACACCCCGCCAGTGCCTGATGTC
          GGGGC GCG CGCT AC GC GT GC CC GCCCATGACACC C CC GT CC GA GT
-MEXICO   GGGGCTGCGGCGCTGACGGCTGTGGCGCCTGCCCATGACACCTCACCCGTCCCGGACGTT 5530v      5540v      5550v      5560v      5570v      5580v
-BURMA    GACTCCCGCGGCGCCATCTTGCGCCGGCAGTATAACCTATCAACATCTCCCCTTACCTCT
          GA TC CGCGG GC AT   T CGCCG CAGTATAA  T TC AC TC CCCCT AC TC
-MEXICO   GATTCTCGCGGTGCAATTCTACGCCGCCAGTATAATTTGTCTACTTCACCCCTGACATCC 5590v      5600v      5610v      5620v      5630v      5640v
-BURMA    TCCGTGGCCACCGGCACTAACCTGGTTCTTTATGCCGCCCCTCTTAGTCCGCTTTTACCC
          TC GTGGCC C GGCACTAA  T GT CT TATGC GCCCC CTTA TCCGC T T CC
-MEXICO   TCTGTGGCCTCTGGCACTAATTTAGTCCTGTATGCAGCCCCCCTTAATCCGCCTCTGCCG
```

Fig. 2A

```
         5650v      5660v      5670v      5680v      5690v      5700v
-BURMA   CTTCAGGACGGCACCAATACCCATATAATGGCCACGGAAGCTTCTAATTATGCCCAGTAC
         CT CAGGACGG AC AATAC CA AT ATGGCCAC GA GC TC AATTATGC CAGTAC
-MEXICO  CTGCAGGACGGTACTAATACTCACATTATGGCCACAGAGGCCTCCAATTATGCACAGTAC 5710v      5720v      5730v      5740v      5750v      5760v
-BURMA   CGGGTTGCCCGTGCCACAATCCGTTACCGCCCGCTGGTCCCCAATGCTGTCGGCGGTTAC
         CGGGTTGCCCG GC AC ATCCGTTACCG CC CT GT CC AATGC GT GG GG TA
-MEXICO  CGGGTTGCCCGCGCTACTATCCGTTACCGGCCCCTAGTGCCTAATGCAGTTGGAGGCTAT trpE-(C2) I->
         5770v      5780v      5790v      5800v      5810v      5820v
-BURMA   GCCATCTCCATCTCATTCTGGCCACAGACCACCACCACCCCGACGTCCGTTGATATGAAT
         GC AT TCCAT TC TTCTGGCC CA AC ACCAC ACCCC AC TC GTTGA ATGAAT
-MEXICO  GCTATATCCATTTCTTTCTGGCCTCAAACAACCACAACCCCTACATCTGTTGACATGAAT 5830v      5840v      5850v      5860v      5870v      5880v
-BURMA   TCAATAACCTCGACGGATGTTCGTATTTTAGTCCAGCCCGGCATAGCCTCTGAGCTTGTG
         TC AT AC TC AC GATGT  G ATT T GT CA CC GGCATAGC TCTGA  T GT
-MEXICO  TCCATTACTTCCACTGATGTCAGGATTCTTGTTCAACCTGGCATAGCATCTGAATTGGTC 5890v      5900v      5910v      5920v      5930v      5940v
-BURMA   ATCCCAAGTGAGCGCCTACACTATCGTAACCAAGGCTGGCGCTCCGTCGAGACCTCTGGG
         ATCCCAAG GAGCGCCT CACTA CG AA CAAGG TGGCGCTC GT GAGAC TCTGG
-MEXICO  ATCCCAAGCGAGCGCCTTCACTACCGCAATCAAGGTTGGCGCTCGGTTGAGACATCTGGT 5950v      5960v      5970v      5980v      5990v      6000v
-BURMA   GTGGCTGAGGAGGAGGCTACCTCTGGTCTTGTTATGCTTTGCATACATGGCTCACTCGTA
         GT GCTGAGGAGGA GC ACCTC GGTCTTGT ATG T TGCATACATGGCTC C GT
-MEXICO  GTTGCTGAGGAGGAAGCCACCTCCGGTCTTGTCATGTTATGCATACATGGCTCTCCAGTT 6010v      6020v      6030v      6040v      6050v      6060v
-BURMA   AATTCCTATACTAATACACCCTATACCGGTGCCCTCGGGCTGTTGGACTTTGCCCTTGAG
         AA TCCTATAC AATAC CC TATACCGGTGCCCT GG  T  TGGACTTTGCC T GAG
-MEXICO  AACTCCTATACCAATACCCCTTATACCGGTGCCCTTGGCTTACTGGACTTTGCCTTAGAG 6070v      6080v      6090v      6100v      6110v      6120v
-BURMA   CTTGAGTTTCGCAACCTTACCCCCGGTAACACCAATACGCGGGTCTCCCGTTATTCCAGC
         CTTGAGTTTCGCAA CT ACC CC GTAACACCAATAC CG GT TCCCGTTA TCCAGC
-MEXICO  CTTGAGTTTCGCAATCTCACCACCTGTAACACCAATACACGTGTGTCCCGTTACTCCAGC I-SG3-->
         6130v      6140v      6150v      6160v      6170v      6180v
-BURMA   ACTGCTCGCCACCGCCTTCGTCGCGGTGCGGACGGGACTGCCGAGCTCACCACCACGGCT
         ACTGCTCG CAC C  CG G G     GACGGGACTGC GAGCT ACCAC AC GC
-MEXICO  ACTGCTCGTCACTCCGCCCGAGGGGCC---GACGGGACTGCGGAGCTGACCACAACTGCA
```

Fig. 2B

```
              6190v      6200v      6210v      6220v      6230v      6240v
-BURMA    GCTACCCGCTTTATGAAGGACCTCTATTTTACTAGTACTAATGGTGTCGGTGAGATCGGC
          GC ACC G TT ATGAA GA CTC A TTTAC G    TAATGG GT GGTGA TCGGC
-MEXICO   GCCACCAGGTTCATGAAAGATCTCCACTTTACCGGCCTTAATGGGGTAGGTGAAGTCGGC 6250v      6260v      6270v      6280v      6290v      6300v
-BURMA    CGCGGGATAGCCCTCACCCTGTTCAACCTTGCTGACACTCTGCTTGGCGGCCTGCCGACA
          CGCGGGATAGC CT AC  T  T AACCTTGCTGACAC CT CT GGCGG CT CCGACA
-MEXICO   CGCGGGATAGCTCTAACATTACTTAACCTTGCTGACACGCTCCTCGGCGGGCTCCCGACA 6310v      6320v      6330v      6340v      6350v      6360v
-BURMA    GAATTGATTTCGTCGGCTGGTGGCCAGCTGTTCTACTCCCGTCCCGTTGTCTCAGCCAAT
          GAATT ATTTCGTCGGCTGG GG CA CTGTT TA TCCCG CC GTTGTCTCAGCCAAT
-MEXICO   GAATTAATTTCGTCGGCTGGCGGGCAACTGTTTTATTCCCGCCCGGTTGTCTCAGCCAAT 6370v      6380v      6390v      6400v      6410v      6420v
-BURMA    GGCGAGCCGACTGTTAAGTTGTATACATCTGTAGAGAATGCTCAGCAGGATAAGGGTATT
          GGCGAGCC AC GT AAG T TATACATC GT GAGAATGCTCAGCAGGATAAGGGT TT
-MEXICO   GGCGAGCCAACCGTGAAGCTCTATACATCAGTGGAGAATGCTCAGCAGGATAAGGGTGTT 6430v      6440v      6450v      6460v      6470v      6480v
-BURMA    GCAATCCCGCATGACATTGACCTCGGAGAATCTCGTGTGGTTATTCAGGATTATGATAAC
          GC ATCCC CA GA AT GA CT GG GA TC CGTGTGGT ATTCAGGATTATGA AAC
-MEXICO   GCTATCCCCCACGATATCGATCTTGGTGATTCGCGTGTGGTCATTCAGGATTATGACAAC 6490v      6500v      6510v      6520v      6530v      6540v
-BURMA    CAACATGAACAAGATCGGCCGACGCCTTCTCCAGCCCCATCGCGCCCTTTCTCTGTCCTT
          CA CATGA CA GATCGGCC AC CC TC CC GC CCATC CG CCTTT TCTGT CT
-MEXICO   CAGCATGAGCAGGATCGGCCCACCCCGTCGCCTGCGCCATCTCGGCCTTTTTCTGTTCTC 6550v      6560v      6570v      6580v      6590v      6600v
-BURMA    CGAGCTAATGATGTGCTTTGGCTCTCTCTCACCGCTGCCGAGTATGACCAGTCCACTTAT
          CGAGC AATGATGT CTTTGGCT TC CTCAC GC GCCGAGTATGACCAGTCCACTTA
-MEXICO   CGAGCAAATGATGTACTTTGGCTGTCCCTCACTGCAGCCGAGTATGACCAGTCCACTTAC 6610v      6620v      6630v      6640v      6650v      6660v
-BURMA    GGCTCTTCGACTGGCCCAGTTTATGTTTCTGACTCTGTGACCTTGGTTAATGTTGCGACC
          GG TC TC ACTGGCCC GTTTAT T TC GAC   GTGAC TTGGT AATGTTGCGAC
-MEXICO   GGGTCGTCAACTGGCCCGGTTTATATCTCGGACAGCGTGACTTTGGTGAATGTTGCGACT 6670v      6680v      6690v      6700v      6710v      6720v
-BURMA    GGCGCGCAGGCCGTTGCCCGGTCGCTCGATTGGACCAAGGTCACACTTGACGGTCGCCCC
          GGCGCGCAGGCCGT GCCCG TCGCT GA TGG CCAA GTCAC CT GACGG CG CCC
-MEXICO   GGCGCGCAGGCCGTAGCCCGATCGCTTGACTGGTCCAAAGTCACCCTCGACGGGCGGCCC 6730v      6740v      6750v      6760v      6770v      6780v
-BURMA    CTCTCCACCATCCAGCAGTACTCGAAGACCTTCTTTGTCCTGCCGCTCCGCGGTAAGCTC
          CTC C AC  T  AGCA TA TC AAGAC TTCTTTGT CT CC CT CG GG AAGCTC
-MEXICO   CTCCCGACTGTTGAGCAATATTCCAAGACATTCTTTGTGCTCCCCCTTCGTGGCAAGCTC
```

Fig. 2C

```
              6790v      6800v      6810v      6820v      6830v      6840v
-BURMA    TCTTTCTGGGAGGCAGGCACAACTAAAGCCGGGTACCCTTATAATTATAACACCACTGCT
          TC TT TGGGAGGC GGCACAAC AAAGC GG TA CCTTATAATTATAA AC ACTGCT
-MEXICO   TCCTTTTGGGAGGCCGGCACAACAAAAGCAGGTTATCCTTATAATTATAATACTACTGCT 6850v      6860v      6870v      6880v      6890v      6900v
-BURMA    AGCGACCAACTGCTTGTCGAGAATGCCGCCGGGCACCGGGTCGCTATTTCCACTTACACC
          AG GACCA  T CT  T GA AATGC GCCGG CA CGGGTCGC ATTTC AC TA ACC
-MEXICO   AGTGACCAGATTCTGATTGAAAATGCTGCCGGCCATCGGGTCGCCATTTCAACCTATACC 6910v      6920v      6930v      6940v      6950v      6960v
-BURMA    ACTAGCCTGGGTGCTGGTCCCGTCTCCATTTCTGCGGTTGCCGTTTTAGCCCCCCACTCT
          AC AG CT GG GC GGTCC GTC CCATTTCTGCGG  GC GTTTT GC CC C CTC
-MEXICO   ACCAGGCTTGGGGCCGGTCCGGTCGCCATTTCTGCGGCCGCGGTTTTGGCTCCACGCTCC

I-406.3-2-->
              6970v      6980v      6990v      7000v      7010v      7020v
-BURMA    GCGCTAGCATTGCTTGAGGATACCTTGGACTACCCTGCCCGCGCCCATACTTTTGATGAT
          GC CT GC  TGCT GAGGATAC TT GA TA CC G  CG GC CA AC TTTGATGA
-MEXICO   GCCCTGGCTCTGCTGGAGGATACTTTTGATTATCCGGGGCGGGCGCACACATTTGATGAC 7030v      7040v      7050v      7060v      7070v      7080v
-BURMA    TTCTGCCCAGAGTGCCGCCCCCTTGGCCTTCAGGGCTGCGCTTTCCAGTCTACTGTCGCT
          TTCTGCCC GA TGCCGC C  T GGCCT CAGGG TG GCTTTCCAGTC ACTGTCGCT
-MEXICO   TTCTGCCCTGAATGCCGCGCTTTAGGCCTCCAGGGTTGTGCTTTCCAGTCAACTGTCGCT

<--SG3-I
                                  <--406.3-2-I
              7090v      7100v      7110v      7120v      7130v      7140v
-BURMA    GAGCTTCAGCGCCTTAAGATGAAGGTGGGTAAAACTCGGGAGTTGTAGTTTATTTGCTTG
          GAGCT CAGCGCCTTAA  T AAGGTGGGTAAAACTCGGGAGTTGTAGTTTATTTG TG
-MEXICO   GAGCTCCAGCGCCTTAAAGTTAAGGTGGGTAAAACTCGGGAGTTGTAGTTTATTTGGCTG 7150v      7160v          7170v      7180v      7190v
-BURMA    TGCCCCCCTTCTTTCTGTTGC---------TTATTTCTCATTTCTGCGTTCCGCGCTCCC
          TGCCC CCT CTT       TGC       TTATTTC  TTTCT GT CCGCGCTCCC
-MEXICO   TGCCCACCTACTTATATCTGCTGATTTCCTTTATTTCCTTTTTCTCGGTCCCGCGCTCCC

<-I ORF2          <-I trpE-C2
           v 7195
-BURMA    TGA
          TGA
-MEXICO   TGA
```

Fig. 2D

```
              10        20        30        40        50        60
HEV(B)  MNNMSFAAPMGSRPCALGLFCCCSSCFCLCCPRHRPVSRLAAVVGGAAAVPAVVSGVTGL
        X::: :::::::::::::::::::::::::::::::::::::::::::::::::::::::
HEV(M)  MNNMWFAAPMGSPPCALGLFCCCSSCFCLCCPRHRPVSRLAAVVGGAAAVPAVVSGVTGL
              10        20        30        40        50        60

406.4-2
              70        80        90        100       110       120
HEV(B)  ILSPSQSPIFIQPTPSPPMSPLRPGLDLVFANPPDHSAPLGVTRPSAPPLPHVVDLPQLG
        ::::::::::::::: :.   :::::::.:::..::  ::::  .:::::::..:.:::  :
HEV(M)  ILSPSQSPIFIQPTPLPQTLPLRPGLDLAFANQPGHLAPLGEIRPSAPPLPPVADLPQPG
              70        80        90        100       110       120

HEV(B)  PRRZ
        ::X
HEV(M)  LRRZ
```

Fig. 3

```
                    10         20         30         40         50         60
HEV(B)    MRPRPILLLLLMFLPMLPAPPPGQPSGRRRGRRSGGSGGGFWGDRVDSQPFAIPYIHPTN
          X:::.:.:::.:.:::::::::.:::::::::::::.::::::::::::::::::::::::
HEV(M)    MRPRPLLLLLFLLFLPMLPAPPTGQPSGRRRGRRSGGTGGGFWGDRVDSQPFAIPYIHPTN
                    10         20         30         40         50         60

62K
                    70         80         90        100        110        120
HEV(B)    PFAPDVTAAAGAGPRVRQPARPLGSAWRDQAQRPAVASRRRPTTAGAAPLTAVAPAHDTP
          ::::::.:::.:::::.::::::::.::::::::.:::::::::.:::::.:::::::::.
HEV(M)    PFAPDVAAASGSGPRLRQPARPLGSTWRDQAQRPSAASRRRPATAGAAALTAVAPAHDTS
                    70         80         90        100        110        120

130        140        150        160        170        180
HEV(B)    PVPDVDSRGAILRRQYNLSTSPLTSSVATGTNLVLYAAPLSPLLPLQDGTNTHIMATEAS
          ::::::::::::::::::::::::::.::::::::::::::.:.:::::::::::::::::
HEV(M)    PVPDVDSRGAILRRQYNLSTSPLTSSVASGTNLVLYAAPLNPPLPLQDGTNTHIMATEAS
                   130        140        150        160        170        180

C-2
                   190        200        210        220        230        240
HEV(B)    NYAQYRVARATIRYRPLVPNAVGGYAISISFWPQTTTTPTSVDMNSITSTDVRILVQPGI
          ::::::::::::::::::::::::::::::::::::::::::::::::::::::::::::
HEV(M)    NYAQYRVARATIRYRPLVPNAVGGYAISISFWPQTTTTPTSVDMNSITSTDVRILVQPGI
                   190        200        210        220        230        240

250        260        270        280        290        300
HEV(B)    ASELVIPSERLHYRNQGWRSVETSGVAEEEATSGLVMLCIHGSLVNSYTNTPYTGALGLL
          ::::::::::::::::::::::::::::::::::::::::::::: ::::::::::::::
HEV(M)    ASELVIPSERLHYRNQGWRSVETSGVAEEEATSGLVMLCIHGSPVNSYTNTPYTGALGLL
                   250        260        270        280        290        300

SG3
                   310        320        330        340        350        360
HEV(B)    DFALELEFRNLTPGNTNTRVSRYSSTARHRLRRGADGTAELTTTAATRFMKDLYFTSTNG
          ::::::::::::: :::::::::::::::::: .::::::::::::::::::.::. ::
HEV(M)    DFALELEFRNLTTCNTNTRVSRYSSTARHS-ARGADGTAELTTTAATRFMKDLHFTGLNG
                   310        320        330        340        350

370        380        390        400        410        420
HEV(B)    VGEIGRGIALTLFNLADTLLGGLPTELISSAGGQLFYSRPVVSANGEPTVKLYTSVENAQ
          :::.::::::::.:::::::::::::::::::::::::::::::::::::::::::::::
HEV(M)    VGEVGRGIALTLLNLADTLLGGLPTELISSAGGQLFYSRPVVSANGEPTVKLYTSVENAQ
               360        370        380        390        400        410

430        440        450        460        470        480
HEV(B)    QDKGIAIPHDIDLGESRVVIQDYDNQHEQDRPTPSPAPSRPFSVLRANDVLWLSLTAAEY
          ::::.:::::::::: ::::::::::::::::::::::::::::::::::::::::::::
HEV(M)    QDKGVAIPHDIDLGDSRVVIQDYDNQHEQDRPTPSPAPSRPFSVLRANDVLWLSLTAAEY
               420        430        440        450        460        470
```

Fig. 4A

```
             490       500       510       520       530       540
HEV(B)  DQSTYGSSTGPVYVSDSVTLVNVATGAQAVARSLDWTKVTLDGRPLSTIQQYSKTFFVLP
        ::::::::::::::::.:::::::::::::::::::::::::::::..:::::::::::
HEV(M)  DQSTYGSSTGPVYISDSVTLVNVATGAQAVARSLDWSKVTLDGRPLPTVEQYSKTFFVLP
          480       490       500       510       520       530

550       560       570       580       590       600
HEV(B)  LRGKLSFWEAGTTKAGYPYNYNTTASDQLLVENAAGHRVAISTYTTSLGAGPVSISAVAV
        ::::::::::::::::::::::::::::::.:.:::::::::::::::.::::::.:::
HEV(M)  LRGKLSFWEAGTTKAGYPYNYNTTASDQILIENAAGHRVAISTYTTRLGAGPVAISAAAV
          540       550       560       570       580       590

406.3-2
             610       620       630       640       650
HEV(B)  LAPHSALALLEDTLDYPARAHTFDDFCPECRPLGLQGCAFQSTVAELQRLKMVGKTR
        :::.:.::::::::.:::.:.::::::::::.:::::::::::::::::::.:::::
HEV(M)  LAPRALALLEDTFDYPGRAHTFDDFCPECRALGLQGCAFQSTVAELQRLKVKVGKTR
          600       610       620       630       640       650

HEV(B)  ELZ
        :::
HEV(M)  ELZ
```

Fig. 4B

```
                                   10         20        30
MEXICAN(SEQ ID NO:18)    ANQPGHLAPLGEIRPSAPPLPPVADLPQPGLRR
                         :::.:: :::: .:::::::::::.:::: : ::
BURMA(SEQ ID NO:17)      ANPPDHSAPLGVTRPSAPPLPHVVDLPQLGPRR
                                   10         20        30
```

HEPATITIS E VIRUS ANTIGENS AND USES THEREFOR

This application is a continuation-in-part of U.S. application Ser. No. 08/327,952, filed Oct. 24, 1994, abandoned which is a continuation-in-part of U.S. application Ser. No. 08/240,049, filed May 9, 1994, now U.S. Pat. No. 5,686,239, which is a continuation-in-part of U.S. application Ser. No. 07/876,941, filed May 1, 1992, now U.S. Pat. No. 5,885,768, and U.S. application Ser. No. 07/870,985, filed Apr. 20, 1992, which are both continuation-in-part applications of U.S. application Ser. No. 07/822,335, filed Jan. 17, 1992, now abandoned, which is a continuation-in-part of U.S. application Ser. No. 07/505,888, filed Apr. 5, 1990, now abandoned, which is a continuation-in-part of U.S. application Ser. No. 07/420,921, filed Oct. 13, 1989, now abandoned, which is a continuation-in-part of U.S. application Ser. No. 07/367,486, filed Jun. 16, 1989, now abandoned, which is a continuation-in-part of U.S. application Ser. No. 07/336,672, filed Apr. 11, 1989, now abandoned, which is a continuation-in-part of U.S. application Ser. No. 07/208,997, filed Jun. 17, 1988, now abandoned, all of which are herein incorporated by reference.

FIELD OF INVENTION

This invention relates to antigens derived from enterically transmitted nonA/nonB hepatitis viral agent, also referred to herein as hepatitis E virus (HEV), and to diagnostic methods, diagnostic assays, vaccine compositions and vaccine methods, which employ such antigens.

REFERENCES

Arankalle, V. A., et al., The Lancet, 550 (Mar. 12, 1988).
Ausubel, F. M., et al., CURRENT PROTOCOLS IN MOLECULAR BIOLOGY, John Wiley and Sons, Inc., Media Pa.
Beames, et al., Biotechniques 11:378 (1991).
Bradley, D., et al., J. Gen. Virol., 69:731 (1988).
Bradley, D. W., et al., Proc. Nat. Acad. Sci., USA, 84:6277–6281 (1987).
Chauhan, et al., Lancet, 341:149 (1993).
Chomczynski, P., et al., Anal. Biochem. 162:156 (1987).
Cleland, W. W., Biochem. 3:480–495 (1964).
Earl, P. L., et al., "Expression of proteins in mammalian cells using vaccinia" In Current Protocols in Molecular Biology (F. M. Ausubel, et al. Eds.), Greene Publishing Associates & Wiley Interscience, New York (1991).
Elliott, J. I., et al., Anal. Biochem. 211:94–101 (1993).
Gellissen, G., et al., Antonie Van Leeuwenhoek, 62(1–2):79–93 (1992).
Goeddel, D. V., Methods in Enzymology 185 (1990).
Guthrie, C., and G. R. Fink, Methods in Enzymology 194 (1991).
Harlow, E., et al., ANTIBODIES: A LABORATORY MANUAL, Cold Spring Harbor Laboratory Press (1988).
Haynes, J., et al., Nuc. Acid. Res. 11:687–706 (1983).
Huang, C—C., et al., Virology, 191:550–558 (1992).
Kaufman, R. J., "Selection and coamplification of heterologous genes in mammalian cells," in Methods in Enzymology, vol. 185, pp537–566. Academic Press, Inc., San Diego Calif. (1991).
Kawasaki, E. S., et al., in PCR Technology: Principles and Applications of DNA Amplification (H. A. Erlich, ed.) Stockton Press (1989).
Khuroo, M. S., Am. J. Med., 48:818 (1980).
Khuroo, M. S., et al., Am. J. Med., 70:58 (1981).
Koonin, E. V., et al., Proc. Nat. Acad. Sci. USA, 89:8259 (1992).
Krawczynski, K. and D. W. Bradley, J. Inf. Diseases 159:1042–1049 (1989).
Lanford, R. E., et al., In Vitro Cellular and Devel Biol, 25 (2):174 (1989).
Lau, Y. F., et al., Mol. Cell. Biol. 4:1469–1475 (1984).
Maniatis, T., et al., MOLECULAR CLONING: A LABORATORY MANUAL, Cold Spring Harbor Laboratory (1982).
McCaustland, K., et al., J. Virological Methods 35:331–342 (1991).
Moss, B., et al., CURRENT PROTOCOLS IN MOLECULAR BIOLOGY (Section IV, Unit 16) (1991).
Moss, B., et al., U.S. Pat. No. 5,135,855, issued Aug. 4, 1992.
Mullis, K. B., U.S. Pat. No. 4,683,202, issued Jul. 28, 1987.
Mullis, K. B., et al., U.S. Pat. No. 4,683,195, issued Jul. 28, 1987.
Pearson, W. R. and Lipman, D. J., PNAS 85:2444–2448 (1988).
Pearson, W. R., Methods in Enzymology 183:63–98 (1990).
Purdy, M. A., et al., J. Medical Virology 41:90–94 (1993).
Reyes, G., et al., Science 247:1335 (1990).
Reyes, G. R., Arch. Virol. Supp. (Review) 7:15 (1993).
Reilly, P. R., et al., BACULOVIRUS EXPRESSION VECTORS: A LABORATORY MANUAL (1992).
Romanos, M. A., et al., Yeast 8(6):423–488 (1992).
Rosenfeld, J., et al., Anal. Biochem. 203:173–185 (1992).
Rozanov, M. N., et al., J. Gen. Virol., 73:2129 (1992).
Sambrook, J., et al., Molecular Cloning: A Laboratory Manual, Cold Spring Harbor Laboratory. (1989).
Schagger, E. and von Jagow, O., Anal. Biochem. 166:368–379 (1987).
Scoble, H. A., et al., in A Practical Guide to Protein and Peptide Purification (Matsudaira, P., Ed.) Academic Press, NY pp. 125–153 (1993).
Smith, D. B., et al., Gene 67:31 (1988).
Summers, M. D., et al., A Manual of Methods for Baculovirus Vectors and Insect Cell Culture Procedures, Texas Agricultural Experimental Station Bulletin No. 1555, 1988.
Tam, A., et al., Virology, 185:120–131 (1991-a).
Tam, A., et al., Hepatitis E virus: cDNA isolation and sequencing, p. 521–524. In Hollinger, F. B. et al. (ed.), Viral Hepatitis and Liver Disease. Williams and Wilkens, Baltimore. (1991-b).
Tsarev, S. A., et al., Proc. Natl. Acad. Sci. USA 89:559–563 (1992).
Velazquez, O., et al., JAMA 263:3281–3285 (1990).
Wang, A. M., et al. in PCR Protocols: A Guide to Methods and Applications (M. A. Innis, et al., eds.) Academic Press (1990).
Williams, K. R. and Stone, K. L., in Techniques in Protein Chemistry VI (Crabb, J., Ed.) Academic Press, NY pp. 143–153 (1995).
Yarbough, P. O., Serology of HEV in developed and developing countries, INTERaction 2:15–17 (1994).
Yarbough, P. O., et al., J. Virology 65:5790–5797 (1991).
Yarbough, P. O., et al., Assay Development of Diagnostic Tests for Hepatitis E. In Viral Hepatitis and Liver Disease, eds. K. Nishioka, H. Suzuki, S Mishiro, T. Oda, pp. 367–370 (1994).

BACKGROUND OF THE INVENTION

Enterically transmitted non-A/non-B hepatitis viral agent (ET-NANB; also referred to herein as HEV) is the reported cause of hepatitis in several epidemics and sporadic cases in Asia, Africa, Europe, Mexico, and the Indian subcontinent. Infection is usually by water contaminated with feces, although there is some evidence of person to person transmission. The virus does not seem to cause chronic infection. The viral etiology in ET-NANB has been demonstrated by infection of volunteers with pooled fecal isolates; immune electron microscopy (IEM) studies have shown virus particles with 27–34 nm diameters in stools from infected individuals. The virus particles reacted with antibodies in serum from infected individuals from geographically distinct regions, suggesting that a single viral agent or class is responsible for the majority of ET-NANB hepatitis seen worldwide. No antibody reaction was seen in serum from individuals infected with parenterally transmitted NANB virus (also known as hepatitis C virus or HCV), indicating a different specificity between the two NANB types.

In addition to serological differences, the two types of NANB infection show distinct clinical differences. ET-NANB is characteristically an acute infection, often associated with fever and arthralgia, and with portal inflammation and associated bile stasis in liver biopsy specimens (Arankalle, 1988). Symptoms are usually resolved within six weeks. Parenterally transmitted NANB, by contrast, produces a chronic infection in about 50% of the cases. Fever and arthralgia are rarely seen, and inflammation has a predominantly parenchymal distribution (Khuroo, 1980). The course of ET-NANBH is generally uneventful in healthy individuals, and the vast majority of those infected recover without the chronic sequelae seen with HCV. Occasionally the course of disease can be severe, however, as was recently shown by a human volunteer (Chauhan 1993). One peculiar epidemiologic feature of this disease, however, is the markedly high mortality observed in pregnant women; this is reported in numerous studies to be on the order of 10–20% (Khuroo 1981, Reyes 1993). This finding has been seen in a number of epidemiologic studies but at present remains unexplained. Whether this reflects viral pathogenicity, the lethal consequence of the interaction of virus and immune suppressed (pregnant) host, or a reflection of the debilitated prenatal health of a susceptible malnourished population remains to be clarified.

The two viral agents can also be distinguished on the basis of primate host susceptibility. ET-NANB, but not the parenterally transmitted agent, can be transmitted to cynomolgus monkeys. The parenterally transmitted agent is more readily transmitted to chimpanzees than is ET-NANB (Bradley, 1987).

In the earlier-filed parent applications, HEV clones, peptide antigens, and the sequence of the entire HEV genome sequence were disclosed. From HEV ORF-2 expression constructs, recombinant proteins and viral particles were produced.

SUMMARY OF THE INVENTION

The present invention includes a Hepatitis E Virus (HEV) polypeptide composition, consisting of at least one polypeptide derived from the carboxy-terminal 549 amino acids of HEV open reading frame (ORF) 2. The composition may include polypeptides corresponding to this region where the polypeptides have amino acids deleted from the carboxy terminus of the 549 amino acid polypeptide. In one embodiment, at least one polypeptide of the composition contains a carboxy terminal deletion of up to about 24 carboxy terminal amino acids of said 549 amino acid HEV ORF2 polypeptide. Exemplary polypeptides include, but are not limited to, the following: SEQ ID NO:15, SEQ ID NO:16, SEQ ID NO:25, SEQ ID NO:26, SEQ ID NO:27, SEQ ID NO:28, and homologous sequences to those presented herein.

In one embodiment, the composition of the present invention ("the 62K antigen") comprises at least two such polypeptides, for example, two polypeptides having the sequences presented as SEQ ID NO:25 and SEQ ID NO:27 or SEQ ID NO:26 and SEQ ID NO:28 (also including homologous sequences).

The invention further includes a substantially isolated nucleic acid sequence encoding a polypeptide derived from the carboxy-terminal 549 amino acids of HEV open reading frame 2. Exemplary nucleic acid sequences include SEQ ID NO:3, SEQ ID NO:4 and homologous sequences thereto.

In another embodiment, the invention includes an expression vector for producing a Hepatitis E Virus polypeptide antigen composition. Such a vector contains a nucleic acid sequence encoding a polypeptide derived from the carboxy-terminal 549 amino acids of HEV open reading frame 2, where the nucleic acid sequence is (i) inserted into an expression vector, and (ii) operably linked to a promoter able to initiate transcription in a selected host cell. The expression vector may be included in an expression system where the expression vector is carried in a suitable host cell, where the host cell allows the expression of the polypeptides of the present invention. In one embodiment, the expression system includes a baculovirus expression vector where the host cell is an insect cell. Numerous useful expression vectors and systems are known to those skilled in the art and described herein.

In a further embodiment, the present invention includes a Hepatitis E Virus (HEV) polypeptide composition produced by culturing an insect cell containing an expression vector, as described above, under conditions sufficient to express a polypeptide derived from the carboxy-terminal 549 amino acids of HEV open reading frame 2. Such a composition may contain at least one polypeptide having an amino acid sequence selected from the group consisting of SEQ ID NO:15, SEQ ID NO:16, SEQ ID NO:25, SEQ ID NO:26, SEQ ID NO:27, SEQ ID NO:28, and homologous sequences therewith.

In yet another embodiment, the invention includes a Hepatitis E Virus (HEV) polypeptide composition produced by incubating an HEV capsid derived antigen having at least 549 carboxy terminal amino acids of an HEV capsid protein with a baculoviral infected lysate under conditions sufficient to cleave carboxy terminal sequences of the HEV capsid derived antigen.

The present invention also includes another method of producing a Hepatitis E Virus (HEV) polypeptide composition ("62K antigen"). In this method a cell contain one of the above-described expression vectors is cultured under conditions sufficient to express a polypeptide derived from the carboxy-terminal 549 amino acids of HEV open reading frame 2.

The invention further includes a method of detecting hepatitis E virus infection in an individual. In this method, a Hepatitis E Virus (HEV) polypeptide composition, consisting of at least one polypeptide derived from the carboxy-terminal 549 amino acids of HEV open reading frame (ORF) 2, is reacted with a serum sample taken from the individual. The HEV polypeptides are then examined for the presence of bound antibody. In this method, the polypeptides of the HEV polypeptide composition are attached to a solid support, said reacting includes contacting such serum with the support and said examining includes reacting the support and bound antibody with a reporter-labeled anti-human antibody. The invention also includes a kit for ascertaining the presence of antibodies to HEV in a serum sample taken from an individual. Typically the kit includes a solid support with surface-bound antigens wherein the surface-bound antigens are polypeptides of the HEV polypeptide ("62K antigen") composition described herein.

Further, the invention includes vaccine compositions employing the HEV polypeptide antigens of the present invention. A vaccine composition used in immunizing an individual against Hepatitis E Virus (HEV) contains at least one polypeptide derived from the carboxy-terminal 549 amino acids of HEV open reading frame (ORF) 2. The polypeptides of the present invention can be formulated in a pharmaceutically acceptable carrier. The vaccine may include polypeptides corresponding to this region where the polypeptides have amino acids deleted from the carboxy terminus of the 549 amino acid polypeptide. In one embodiment, at least one polypeptide of the vaccine composition contains a carboxy terminal deletion of up to about 24 carboxy terminal amino acids of said 549 amino acid HEV ORF2 polypeptide. Exemplary polypeptides include, but are not limited to, the following: SEQ ID NO:15, SEQ ID NO:16, SEQ ID NO:25, SEQ ID NO:26, SEQ ID NO:27, SEQ ID NO:28, and homologous sequences to those presented herein. The invention also includes a method of inhibiting infection of an individual by HEV. In this method, a vaccine composition of the present invention is administered to a subject using a therapeutically effective amount.

These and other objects and features of the invention will become more fully understood when the following detailed description of the invention is read in conjunction with the accompanying figures.

BRIEF DESCRIPTION OF THE DRAWINGS

FIGS. 2A to 2D, present the nucleotide sequence of ORF2 and ORF3, showing the nucleotide sequences of the HEV ORF2 and ORF3 for Burma (upper line) and Mexico (lower line) strains of HEV;

FIG. 3, presents the amino acid sequence of ORF3, showing the amino acid sequences of the ORF3 protein for Burma (upper line) and Mexico (lower line) strains of HEV;

FIGS. 4A and 4B, presents the amino acid sequence of ORF2, showing the amino acid sequences of the ORF2 protein for the Burma (upper line) and Mexico (lower line) strains of HEV as well as the amino-terminus of each of the 62K, C-2, SG3, 406.3-2 antigens;

FIG. 6a shows PBS-soluble (S) and insoluble (I) proteins from lysate of Sf9 suspension culture cells infected with recombinant baculovirus ORF2-rAcMNPV at various days post infection (DPI) were analyzed by SDS-PAGE. The arrow points to the recombinant ORF-2 protein produced. FIG. 6b is essentially the same as that in FIG. 6a except that immunoblot, instead of Coomassie blue staining, was carried out. The arrows point to the migration of 73K and 62K proteins, respectively.

FIG. 11a has a magnification of ×95,000 and FIG. 11b ×200,000. FIG. 11b shows virus-like particle formation by 73K protein.

DETAILED DESCRIPTION OF THE INVENTION

I. DEFINITIONS

Figure 1:
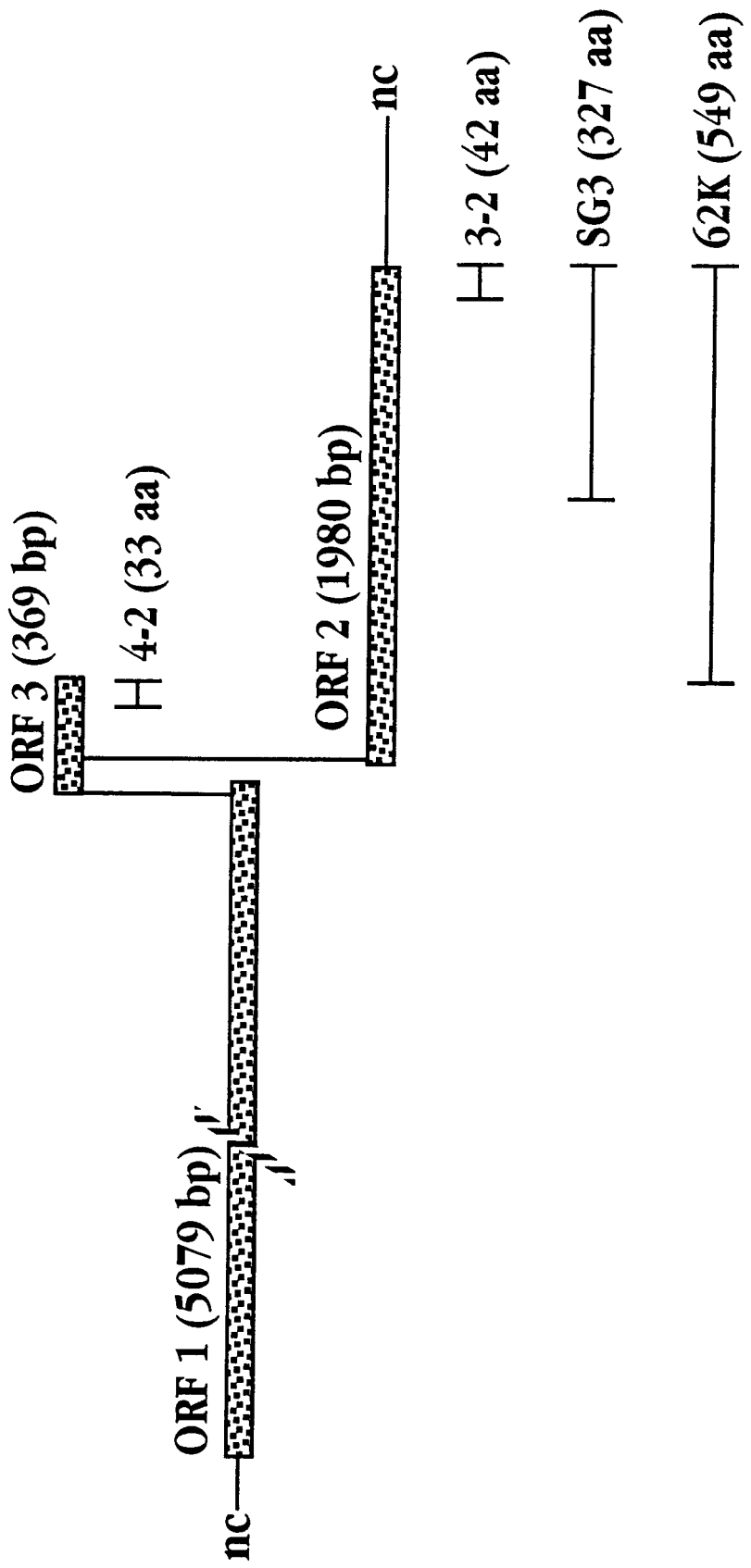
FIG. 1, presents a schematic diagram of the genomic organization of HEV, showing the HEV genome, the arrangement of open reading frames in the genome, and the approximate coding regions for HEV antigens 406.3-2, 406.4-2, SG3, and 62K.

The terms defined below have the following meaning herein:

A. "Enterically transmitted non-A/non-B hepatitis viral agent", "hepatitis E virus", or "HEV" means a virus, virus type, or virus class which (i) causes water-borne, infectious hepatitis, (ii) is transmissible in cynomolgus monkeys, (iii) is serologically distinct from hepatitis A virus (HAV), hepatitis B virus (HBV), hepatitis C virus (HCV), and hepatitis D virus, and (iv) includes a genomic region which is homologous to the 1.33 kb cDNA insert in plasmid pTZKF1 (ET1.1) carried in E. coli strain BB4 identified by ATCC deposit number 67717.

B. "HEV variants" are defined as viral isolates that have at least about 40%, preferably 50%, or more preferably 70% global sequence homology, that is, sequence identity over a length of the viral genome polynucleotide sequence (e.g., ORF2) to known HEV polynucleotide sequences disclosed herein (e.g., SEQ ID NO:1 or SEQ ID NO:2).

"Sequence homology" is determined essentially as follows. Two polynucleotide sequences of the same length (preferably, the entire viral genome) are considered to be homologous to one another, if, when they are aligned using the ALIGN program, over 40%, preferably 50%, or more preferably 70% of the nucleic acids in the highest scoring alignment are identically aligned using a ktup of 1, the default parameters and the default PAM matrix.

The ALIGN program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

In determining whether two viruses are "highly homologous" to each other, the complete sequence of all the viral proteins for one virus are optimally, globally aligned with the viral proteins or polyprotein of the other virus using the ALIGN program of the above suite using a ktup of 1, the default parameters and the default PAM matrix. Regions of dissimilarity or similarity are not excluded from the analysis. Differences in lengths between the two sequences are considered as mismatches. Alternatively, viral structural protein regions are typically used to determine relatedness between viral isolates. Highly homologous viruses have over 40%, or preferably 50%, or more preferably 70% global polypeptide sequence identity.

C. Two nucleic acid fragments are considered to be "selectively hybridizable" to an HEV polynucleotide, if they are capable of (1) specifically hybridizing to HEV or a variant thereof or (2) specifically priming a polymerase chain reaction: (i) under typical hybridization and wash conditions, as described, for example, in Maniatis, et al., pages 320–328, and 382–389, (ii) using reduced stringency wash conditions that allow at most about 25–30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (for example, in Saiki, R. K, et al.; Mullis; Mullis, et al.), which result in specific amplification of sequences of HEV or its variants.

The degrees of homology (sequence identity) discussed above can be selected for by hybridization using wash conditions of appropriate stringency for identification of clones from gene libraries (or other sources of genetic material), as is well known in the art.

D. An "HEV polypeptide" is defined herein as any polypeptide homologous to an HEV polypeptide. "Homology," as used herein, is defined as follows. In one embodiment, a polypeptide is homologous to an HEV polypeptide if it is encoded by nucleic acid that selectively hybridizes to sequences of HEV or its variants.

In another embodiment, a polypeptide is homologous to an HEV polypeptide if it is encoded by HEV or its variants, as defined above, polypeptides of this group are typically larger than 15, preferably 25, or more preferably 35, contiguous amino acids. Further, for polypeptides longer than about 60 amino acids, sequence comparisons for the purpose of determining "polypeptide homology" are performed using the local alignment program LALIGN. The polypeptide sequence, is compared against the HEV amino acid sequence or any of its variants, as defined above, using the LALIGN program with a ktup of 1, default parameters and the default PAM.

Any polypeptide with an optimal alignment longer than 60 amino acids and greater than 40%, preferably 50%, or more preferably 70% of identically aligned amino acids is considered to be a "homologous polypeptide." The LALIGN program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

E. A polynucleotide is "derived from" HEV if it has the same or substantially the same basepair sequence as a region of an HEV genome, cDNA of HEV or complements thereof, or if it displays homology as noted under "B" or "C" above.

A polypeptide or polypeptide "fragment" is "derived from" HEV if it is (i) encoded by an open reading frame of an HEV polynucleotide, or (ii) displays homology to HEV polypeptides as noted under "B" and "D" above, or (iii) is specifically immunoreactive with HEV positive sera.

F. In the context of the present invention, the phrase "nucleic acid sequences," when referring to sequences which encode a protein, polypeptide, or peptide, is meant to include degenerative nucleic acid sequences which encode homologous protein, polypeptide or peptide sequences as well as the disclosed sequence.

G. An "epitope" is the antigenic determinant defined as the specific portion of an antigen with which the antigen binding portion of a specific antibody interacts. The terms "immunogenic region" or "epitope" are used interchangably.

H. An antigen or epitope is "specifically immunoreactive" with HEV positive sera when the epitope/antigen binds to antibodies present in the HEV infected sera but does not bind to antibodies present in the majority (greater than about 90%, preferably greater than 95%) of sera from individuals who are not or have not been infected with HEV. "Specifically immunoreactive" antigens or epitopes may also be immunoreactive with monoclonal or polyclonal antibodies generated against specific HEV epitopes or antigens.

An antibody or antibody composition (e.g., polyclonal antibodies) is "specifically immunoreactive" with HEV when the antibody or antibody composition is immunoreactive with an HEV antigen but not with unrelated hepatitis virus (e.g., HAV, HBV, HCV or HDV) antigens. Further, "specifically immunoreactive antibodies" are not immunoreactive with antigens typically present in normal sera.

I. In two or more known peptide sequences which are more than about 70% homologous in amino acid sequence, a third amino acid sequence will be "internally consistent with the known sequences" if each amino acid in the third sequence is identical to at least one of the amino acids in the known sequences.

J. The "epitope formed by" a given amino acid sequence is the epitope produced by the secondary/tertiary structure of that sequence in aqueous solution.

K. The "antigen binding site" is that region of an antibody molecule contained within the variable regions of the antibody which directly participates in binding the antigen.

L. A specified "peptide antigen containing the epitope formed by" a specified amino acid sequence includes the specified sequence itself or a portion thereof which is sufficient to define the epitope present in the specified sequence, as evidenced by immunoreactivity to an antibody contained in a human sera sample. The specified peptide antigen may include amino acid substitutions which preserve the epitope.

M. "Substantially isolated" and "purified" are used in several contexts and typically refer to at least partial purification of an HEV virus particle, component (e.g., polynucleotide or polypeptide), or related compound (e.g., anti-HEV antibodies) away from unrelated or contaminating components (e.g., serum cells, proteins, non-HEV polynucleotides and non-anti-HEV antibodies). Methods and procedures for the isolation or purification of compounds or components of interest are described below (e.g., purification of proteins and recombinant production of HEV polypeptides).

N. "62K antigen" is the generic term for a protein or mixture of proteins, where the protein or proteins are derived from the carboxy-terminal 549 amino acids encoded by HEV ORF2 (e.g., SEQ ID NO:15 or SEQ ID NO:16 or sequences homologous thereto); derived proteins may have a comparable amino terminus to the 549 amino acid protein and up to about a 24 amino acid deletion from the carboxy terminal end (e.g., SEQ ID NO:25, SEQ ID NO:26, SEQ ID NO:27 and SEQ ID NO:28).

Similar proteins from the carboxy-terminal amino acid sequence of other variants can be determined by alignment of the variants with, for example, the Burma or Mexico variants (PCT International Application US91/02368, filing date Apr. 5, 1991; PCT International Application US89/02648, filed Jun. 16, 1989, WO 89/12462; both herein incorporated by reference).

Exemplary "62K antigen" polypeptides include the following polypeptides derived from the Burma and Mexico HEV variants: SEQ ID NO:15/SEQ ID NO:16, SEQ ID NO:25/SEQ ID NO:26 and SEQ ID NO:27/SEQ ID NO:28, or a homologous sequence therewith. Further, "62K antigen" includes mixtures of such polypeptides, for example, a preparation containing the polypeptides whose sequences are given as SEQ ID NO:25 and SEQ ID NO:27.

Included within the meaning of "62K antigen" are proteins which are larger than 549 amino acids so long as they contain the just-specified carboxyl terminal sequences encoded by HEV ORF2. For example, a re-engineered 62K antigen "r62K" may optionally have an N-terminal methionine; i.e., a sequence of 550 amino acids. Alternatively, the 62K antigen may be generated as a fusion protein containing, for example, the carboxy-terminal 549 amino acid sequence of HEV ORF2 in addition to sequences encoding β-galactosidase.

II. HEV ANTIGENS

This section describes methods for preparing HEV antigens useful as diagnostic reagents and in vaccine compositions in accordance with the invention.

A. HEV GENOMIC SEQUENCES

HEV genomic clones, and sequences corresponding to the entire HEV genome for different HEV strains were obtained according to published methods (Huang 1992, Yarbough 1991) and as described in the parent applications referenced above. Briefly, RNA isolated from the bile of a cynomolgus monkey having a known HEV infection was cloned, as cDNA fragments, to form a fragment library, and the library was screened by differential hybridization to radiolabeled cDNAs from infected and non-infected bile sources.

The basepair sequence of cloned regions of the HEV fragments in identified clones was determined by standard sequencing methods. With reference to FIG. 1, HEV is a virus with an approximately 7.5 kilo base (kb) single-stranded and polyadenylated RNA genome of positive-sense polarity. Three open reading frames (ORFs) have been assigned to HEV as ORF1, encoding polypeptides with domains of the RNA-directed RNA polymerase and a helicase, ORF2, encoding the putative capsid protein of the virus, and ORF3, a second putative structural protein.

The genomic organization of HEV assigns its non-structural gene(s) at the 5' terminus with the structural gene(s) at the 3' end. Two subgenomic polyadenylated transcripts of approximately 2.0 kb and 3.7 kb in sizes are detected in infected liver and co-terminated at their 3' ends with the 7.5 kb full-length genomic transcript. The genomic organization and expression strategy of HEV suggest that it might be the prototype human pathogen for a new class of RNA virus or perhaps a separate genus within the Caliciviridae family.

The genomic and peptide sequences shown in FIG. 2 correspond to the ORF-2 and ORF-3 regions of Burma (B) (upper lines) and Mexico (M) strains (lower lines) of HEV. The bases indicated in the middle lines represent conserved nucleotides. The numbering system used in the comparison is based on the Burma sequence. The region corresponding to ORF2 has SEQ ID NO:1 and SEQ ID NO:2 for the Burma and Mexico strains, respectively. The region corresponding to the 62 kDa antigen has SEQ ID NO:3 and SEQ ID NO:4 for the Burma and Mexico strains, respectively. The region corresponding to SG3 has SEQ ID NO:5 and SEQ ID NO:6 for the Burma and Mexican strains, respectively. The region corresponding to 406.3-2 has SEQ ID NO:7 and SEQ ID NO:8 for the Burma and Mexico strains, respectively. The region corresponding to ORF3 has SEQ ID NO:9 and SEQ ID NO:10 for the Burma and Mexico strains, respectively. The region corresponding to 406.4-2 has SEQ ID NO:11 and SEQ ID NO:12 for the Burma and Mexico strains, respectively.

B. HEV ANTIGEN SEQUENCES

The amino acid sequences corresponding to the third and second open reading frames of the Burma and Mexico strains of HEV are given in FIGS. 3 and 4, respectively. The sequence listings shown are as follows:

SEQ ID NO:13 and SEQ ID NO:14 correspond to the amino acid sequences for the entire putative capsid protein encoded by the Burma and Mexico strain ORF2, respectively.

SEQ ID NO:15 and SEQ ID NO:16 correspond to the amino acid sequences for the 62K antigens from the Burma and Mexico strain ORF2, respectively.

SEQ ID NO:17 and SEQ ID NO:18 correspond to the amino acid sequences for the peptides SG3 (B) and SG3 (M), respectively. Each peptide includes the carboxyl 327 amino acids of the HEV capsid.

SEQ ID NO:19 and SEQ ID NO:20 correspond to the amino acid sequences for the 406.4-2 (B) and 406.4-2 (M), respectively (FIG. 3). These are 33 amino acid sequences encoded by the ORF3.

SEQ ID NO:21 and SEQ ID NO:22 correspond to the amino acid sequences for the entire protein encoded by ORF3 of the Burma and Mexico strains, respectively.

SEQ ID NO:23 and SEQ ID NO:24 correspond to the amino acid sequences for the peptides 406.3-2 (B) and 406.3-2 (M), respectively. Each peptide is a 42 amino acid peptide in the C-terminal end region of capsid protein encoded by the ORF2, as indicated in the ORF2 sequence (FIG. 4).

Also contemplated are sequences which are internally consistent with the above specified sequences from different strains of HEV antigens. These include SEQ ID NO:13; SEQ ID NO:14, and internally consistent variations between SEQ ID NO:13 and SEQ ID NO:14; SEQ ID NO:15; SEQ ID NO:16, and internally consistent variations between SEQ ID NO:15 and SEQ ID NO:16; SEQ ID NO:17; SEQ ID NO:18; and internally consistent variations between SEQ ID NO:17 and SEQ ID NO:18; SEQ ID NO:19; SEQ ID NO:20; and internally consistent variations between SEQ ID NO:19 and SEQ ID NO:20; SEQ ID NO:21; SEQ ID NO:22, and internally consistent variations between SEQ ID NO:21 and SEQ ID NO:22; SEQ ID NO:23; SEQ ID NO:24, and internally consistent variations between SEQ ID NO:23 and SEQ ID NO:24.

For example, the HEV 406.4-2 antigens have the sequence homology shown in FIG. 16 for the Burma (B) and Mexico (M) strains. The single dots in the sequence comparison indicate recognized high-probability or "neutral" amino acid substitutions. The blank spaces indicate a non-neutral substitution.

A sequence which is internally consistent with these two sequences would have one of the sequences presented in SEQ ID NO:31.

The ORF3 amino acid sequences, 124 amino acids in length, for the Burma and Mexico strains have an 87.1% identity in the 124 amino acids. The ORF2 amino acid sequences, having 659 amino acids of overlap, have a 93.0% identity in the 659 amino acids.

C. Preparation of HEV Antigens

To prepare the 406.3-2 (M) peptide, DNA fragments from the lambda gt11 406.3-2 described in Example 1 was subcloned into the glutathione S-transferase vector pGEX™ to express the 406.3-2(M) antigen, as detailed in Example 1, and in the Tam (1991-b) reference.

The 406.3-2(B) antigen can be prepared by PCR amplification of the Burma SEQ ID NO:5 from above by PCR amplification of the pBET1 plasmid (Tam 1991-b). This plasmid contains a 2.3 kb insert covering the ORF2 and ORF3 for Burma strain HEV sequence. The plasmid is amplified by PCR amplification, using a 5' primer containing an NcoI site and a 3' primer containing a BamHI site (Sakai). The amplified fragment is inserted into the NcoI/BamHI site of a pGEX™ vector, and expressed in an *E. coli* expression system as described in Example 1.

The SG3(B) peptide was prepared by first amplifying the SEQ ID NO:7 sequence with 5' EcoRI-NcoI and 3' BamHI linkers, using a pBET1 clone plasmid containing the entire ORF2 and ORF3 regions of HEV (B). The amplified fragment was inserted into the EcoRI/BamHI site of a Bluescript™ vector (Stratagene, La Jolla, Calif.), according to the manufacturer's instructions. After vector propagation and harvesting, the cloned insert was released by digestion with NcoI and BamHI, and gel purified. The purified fragment was inserted into the NcoI/BamHI site of a pGEX™ vector, and expressed in an *E. coli* expression system as described in Example 1. The SG3(M) peptide can be prepared similarly, using the SEQ ID NO:8 in place of the SEQ ID NO:7.

The capsid protein (B) was prepared substantially as described above by PCR amplification of the SEQ ID NO:1, from a pBET1 plasmid using a 5' primer containing an NcoI site and a 3' primer containing a BamHI site. The amplified fragment was inserted into the NcoI/BamHI site of a pGEX™ vector, and expressed in an *E. coli* expression system as described in Example 1. The capsid protein (M) is similarly prepared.

To prepare the 406.4-2(M) peptide, the lambda gt11 406.4-2 described in Example 1 was subcloned into the glutathione S-transferase vector pGEX™ to express the 406.4-2(M) antigen, as detailed in Example 1.

The 406.4-2(B) antigen can be prepared by PCR amplification of the Burma SEQ ID NO:9 from above by PCR amplification, using a 5' primer containing an NcoI site and a 3' primer containing a BamHI site. The amplified fragment is inserted into the NcoI/BamHI site of a pGEX™ vector, and expressed in an *E. coli* expression system as described in Example 1.

D. Mature Capsid Protein

HEV peptide antigens may also be obtained from purified HEV virus propagated in primary hepatocytes obtained from primate liver, preferably from human or cynomolgus monkey liver. Methods for preparing primary primate hepatocytes for culture, and culture medium conditions effective to preserve liver-specific functions for extended periods in culture are detailed for human hepatocytes in Example 2 below.

After 3 days of growth in culture, the cells are infected with a pooled inoculum of HEV-infected cynomolgus monkey stool pool (fourth passage), as detailed in Example 3. The presence and level of propagating HEV virus in the cells can be measured by indirect immunofluorescence. Where, for example, the primary cells are cynomolgus cells, the cells can be immunoreacted with human HEV anti-sera, followed by immunoreaction with rabbit anti-human IgG antibodies.

Alternatively, the HEV virus can be detected and measured by selective amplification methods involving initial cDNA formation, and PCR amplification of HEV cDNA sequences by PCR amplification, as detailed in Example 3.

Virus particles can be isolated from HEV infected human hepatocytes in culture medium by pelleting the virus through a 30% sucrose cushion by ultracentrifugation. The pelleted virus may be further purified, if desired, by zonal centrifugation through a 10–40% sucrose gradient, combining peak virus fractions.

Other methods for separating virus particles from soluble culture-medium components may be used. For example, clarified culture medium can be passed through a size-exclusion matrix, to separate soluble components by size exclusion.

Alternatively, the clarified culture medium can be passed through an ultrafiltration membrane having a 10–20 nm pore size capable of retaining virus particles, but passing solute (non-particulate) culture medium components.

The present invention allows for glycosylation and other post-translation modifications in intact HEV capsid protein. Capsid isolation from the viral particles can be carried out by standard methods, such as ion exchange and size-exclusion chromatography, and HPLC purification, after solubilization of the virus particles in a solubilizing medium, such as a solution of a non-ionic surfactant. The protein may be purified by affinity chromatography, employing, for example, antibodies purified from anti-HEV antisera. Degradative processes may be employed to obtain partial fragments and peptides from the intact capsid protein (as well as recombinantly produced proteins); e.g. proteases may be employed. Such procedures are known to those skilled in the art.

E. PRODUCTION OF CAPSID ANTIGEN, CLEAVED 62K ANTIGEN, AND RECOMBINANT 62K ANTIGEN, IN INSECT CELLS

This section describes the production of a full length ORF2 (73K), cleaved 62K species of ORF2 (c62K), and re-engineered 62K species of ORF2 (r62K), produced in insect cells.

1. EXPRESSION OF ORF2 IN INSECT CELLS.

General methods, for example, for handling and preparing baculovirus vectors and baculoviral DNA, as well as insect cell culture procedures, are outlined in *A Manual of Methods for Baculovirus Vectors and Insect Cell Culture Procedures* (Summers, M. D. et al., 1988), incorporated herein by reference. The recombinant baculovirus ORF2-*Autographica californica* Nuclear Polyhedrosis Virus (ORF2-rAcNPV) was constructed as described previously, He, J. et al., J. Clin. Microbiology, 31:2167 (1993), herein incorporated by reference. Recombinant baculovirus ORF2-rAcMNPV expressing HEV ORF2 protein was used to infect both *Spodoptera frugiperda*-9 (Sf9) suspension culture and monolayer cell cultures in accordance with the methods detailed in He (1993), and described in Example 4, below.

Infected cell lysates prepared after various times post infection were separated by centrifugation to generate both phosphate-buffered saline (PBS)-soluble and insoluble fractions. Proteins from both fractions were electrophoresed on SDS-polyacrylamide gels, which were either stained with Coomassie-blue solution (FIG. 6A) or transferred to nitrocellulose paper followed by a Western blot analysis (FIG. 6B), in accordance with Example 5.

Figure 6A:
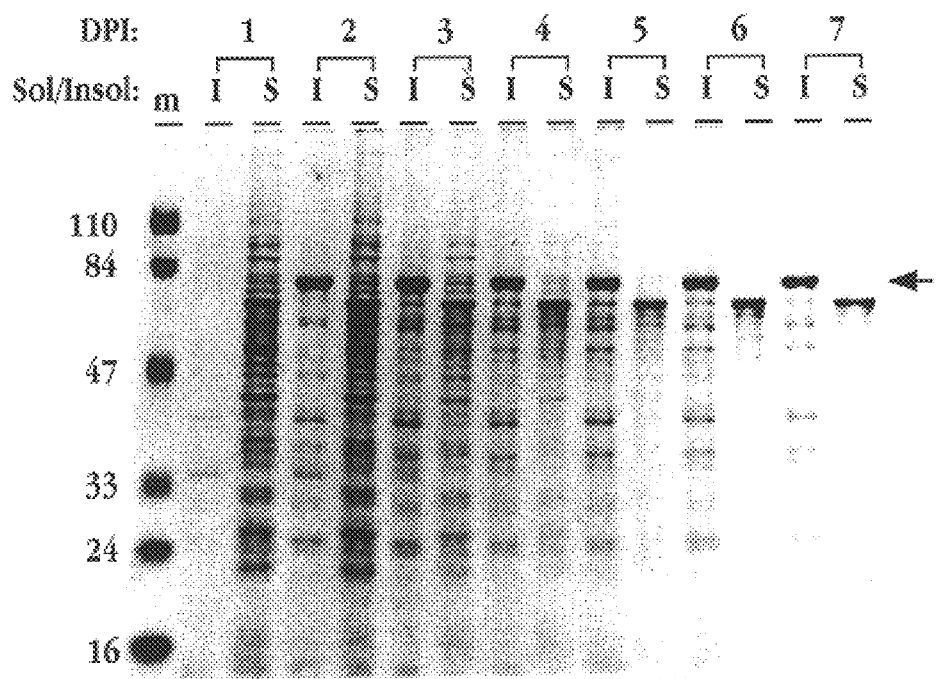
FIGS. 6a and 6b, present data concerning the generation of full length ORF2 73K protein in Sf9 suspension culture and cleavage of 73K to form the 62K species in Sf9 monolayer cells.

A prominent viral protein of approximately 73 kDa in size was observed almost exclusively in PBS-insoluble fractions of suspension culture cells from 2–7 days post infection (FIG. 6A). Migration of this protein correlates well with predicted molecular weight of full length ORF-2. A separate Western blot confirmed that this 73K protein was reactive with ORF2 specific antiserum 1L6 that recognizes the extreme C-terminus of ORF2. Although degradation of host proteins is obvious at late stages of the infection (soluble fractions from days 4–7 post infection), the 73K ORF2 protein appeared to be stable throughout the infection.

Figure 6B:
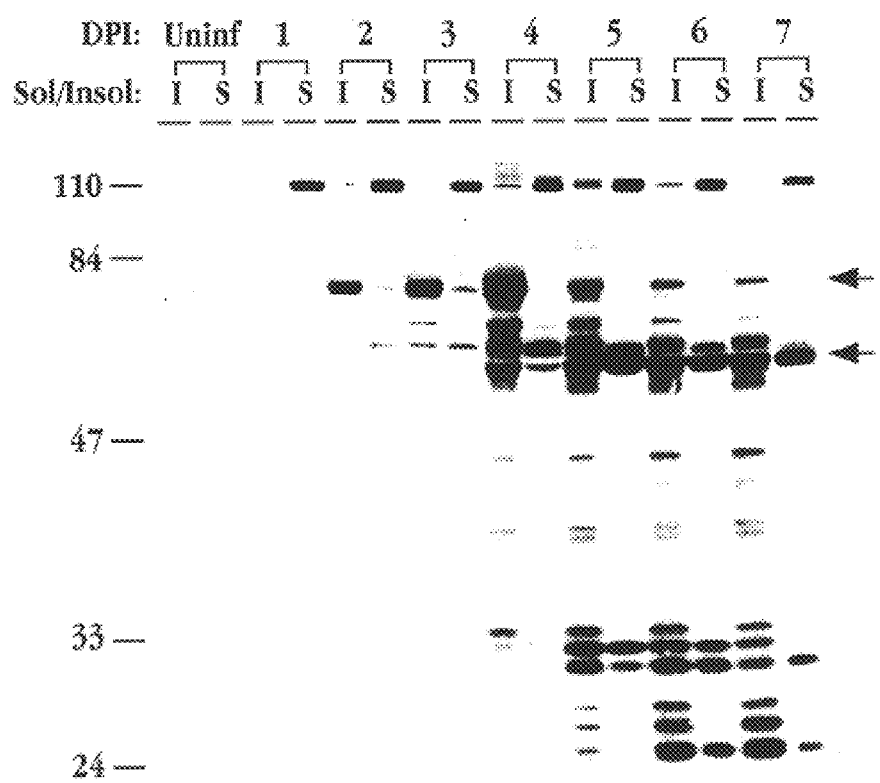

When the same recombinant virus was used to infect the Sf-9 monolayer cells, a different pattern of expression was observed (FIG. 6B). Instead of observing an insoluble 73K protein species, the ORF2 protein was converted to a soluble form banding at approximately 62 kDa in size from day 4–7 post infection. These observations suggested that the insoluble ORF-2 (73K) protein undergoes a proteolytic cleavage to generate a soluble or cleaved 62K protein, referred to as "c62K", in the monolayer cells. Several smaller species migrating around or below 30 kDa were also observed at late stage of the infection. The smaller species were degradation products of the 73K protein.

2. PROTEOLYTIC PROCESSING OF ORF2.

Figure 7:
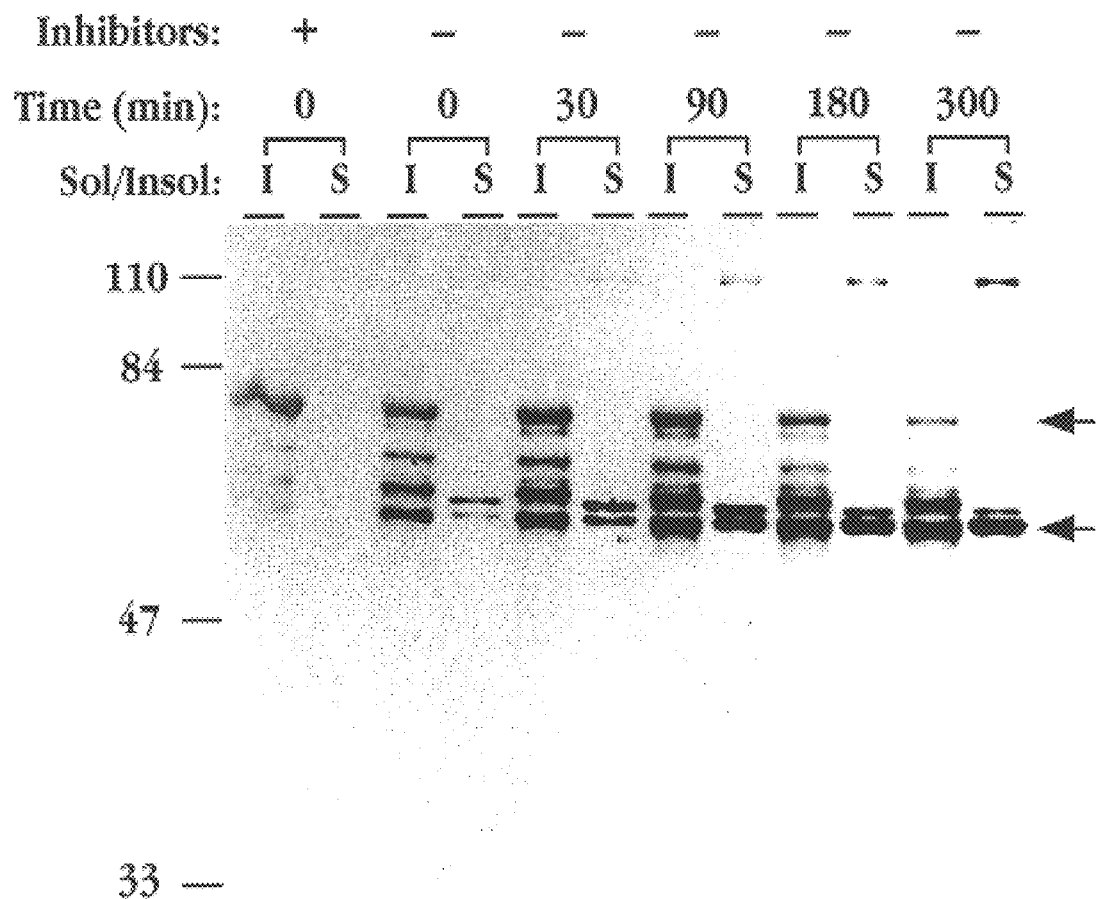
FIG. 7, "Proteolytic Cleavage Of HEV ORF2 Protein In Vitro", shows the in vitro cleavage of the 73K full length ORF2 insoluble (I) protein to the 62K soluble (S) protein at various time points. The presence (+) or absence (−) of proteinase inhibitors are indicated.

The conversion of the 73K protein to the soluble c62K species was observed to occur progressively during the course of infection. Thus, this conversion could be the result of autocatalytic cleavage, stimulating protease activity during the course of infection or at the time of cell harvest, or the combination of these events. To address this question, cell lysates were prepared at day 5 post infection, followed by incubation for various times before proteins in the lysates were denatured. The 73K to c62K conversion was monitored against incubation time as shown in FIG. 7.

When cell lysates were denatured immediately after the cell breakage (0 min. incubation time), the ORF2 protein was present mainly as a 73K insoluble polypeptide, and very little soluble c62K protein was observed. However, when the incubation time was increased between 30 to 300 minutes, the amount of c62K proteins in the soluble fractions increased proportionally. In contrast, the amount of 73K protein in the insoluble fractions decreased, indicating an important role played by proteinase after the cell breakage. The conclusion of this experiment is that the 73K protein could be cleaved to c62K by proteinase activity after cell breakage.

The c62K protein observed in vivo at late infections, as shown in FIG. 6B, could be explained by the prolonged viral infection in which a significant percentage of cells were not viable, causing release of the proteinase activity.

3. CONVERSION OF 73K TO C62K MAY BE BACULOVIRUS INFECTION SPECIFIC.

Figure 8A:
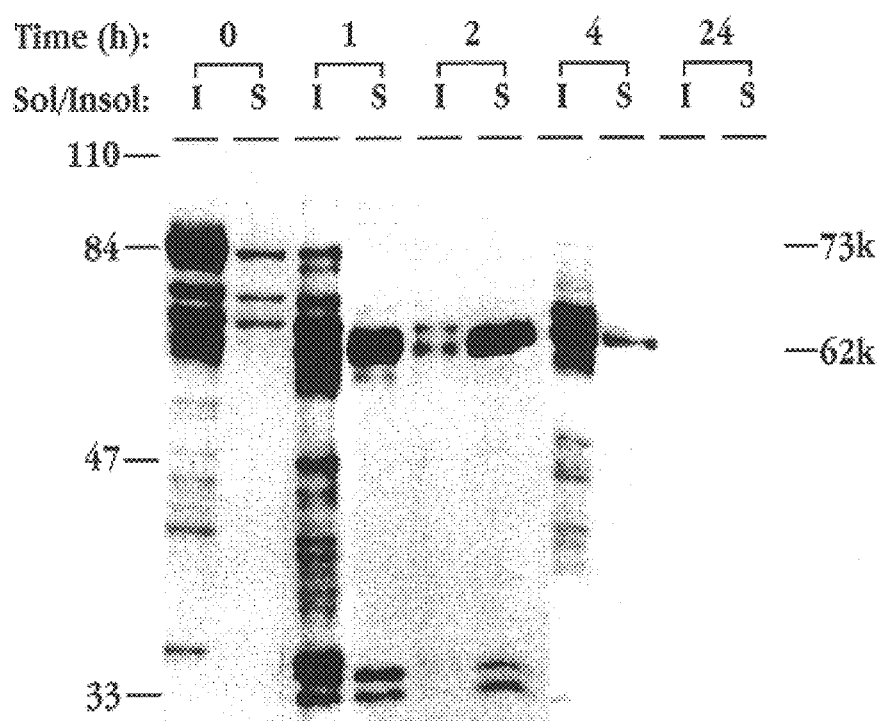
FIGS. 8A and 8B, "73–62K Conversion By Sf9 Suspension Culture Cells", is a comparison of the cleavage of 73K to 62K between the soluble extracts of wild type baculovirus-infected (top panel) or that of uninfected (bottom panel) suspension culture cells. The loading of the samples in two right-most lanes of the bottom panel was reversed.
Figure 8B:
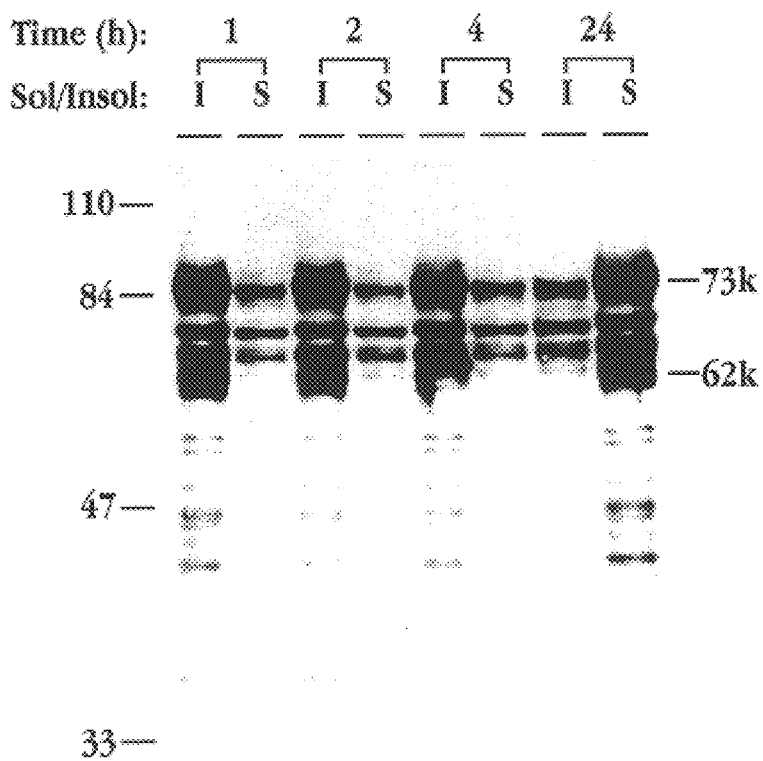

The source of the proteinase responsible for the 73K to c62K cleavage could be from Sf9 cells, baculovirus infected Sf9 cells, or both. To address this question, an extract mixing experiment was carried out to distinguish between these possibilities. An insoluble 73K preparation from Sf9 suspension culture cells was mixed with various soluble extracts and cleavage was monitored by immunoblot analysis (FIG. 8, top panel). Uninfected cell extracts, both from suspension culture and monolayer, had no effect on cleavage, suggesting that cleavage was mediated by viral infection. PBS did not show any effect as expected. Only when extract from an infected cell extract was used, was the cleavage of the 73K protein observed.

The concurrent cleavage of the 73K and accumulation of the c62K protein was further demonstrated in a second experiment in which insoluble 73K preparation was mixed with soluble extract from suspension culture cells infected by wild type baculovirus (FIG. 8, bottom panel). Although cleavage could be observed 1 hr after incubation, it did not occur for as long as 24 hr when an uninfected cell extract was substituted for the infected cell extract (FIG. 8, bottom panel).

4. PURIFICATION OF 73K AND C62K PROTEINS.

Figure 9:
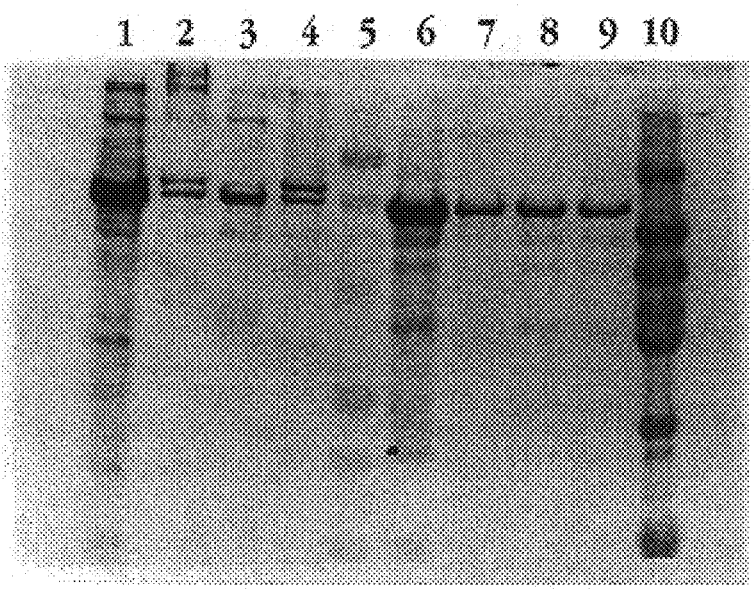
FIG. 9, "73K ORF2 Process Gel", shows various fractions taken during the 73K purification process and run on a 4–20% SDS PAGE and corresponding Western blot. Lane 1, Hyper-D-S Load; lane 2, pooled fractions pH 8.5; lane 3, flow through pH 7.5; lane 4 flow through pH 8.5; lane 5, BioRad MW standards; lane 6, Hyper-D-S Load; lane 7, pooled fractions pH 8.5; lane 8, flow through pH 7.5; lane 9, flow through pH 8.5; lane 10, Promega MW standards. MW standards (Promega mid-range) as follows (top to bottom): phosphorylase B, 97-kDa; BSA, 66-kDa; glutamic dehydrogenase, 55-kDa; ovalbumin, 43-kDa; aldolase, 40-kDa; carbonic anhydrase, 31-kDa; soybean trypsin inhibitor, 21-kDa; lysozyme, 14-kDa. Lanes 1–5, nonreducing conditions; lanes 6–10, reduced with beta mercaptoethanol in the sample preparation buffer.

To determine whether the ORF2 proteins expressed in baculovirus infected cells were forming complex protein structures, as well as determining the cleavage site within ORF2 resulting in the formation of the c62K protein, highly purified protein preparations were prepared. An SDS-PAGE analysis summarizing the purification of the 73K protein is shown in FIG. 9. Details of the purification process are described in Example 6A. The Hyper-D-S column load is shown in lanes 1 and 6 with subsequent flow through and eluted column fractions shown in lanes 2–4 and 7–9. In the lanes where beta mercaptoethanol was removed from the sample disruption buffer (lanes 2–4) it is clear that intrachain disulfide bonding is occurring within the 73K protein and that this association is readily eliminated under reducing conditions.

Recombinant proteins expressed at high levels in both prokaryotic and baculovirus expression systems can accumulate inside the cell in the form of inclusion bodies as was observed for the 73K protein. Under these conditions, it was necessary to develop a procedure for the extraction, solubilization, and refolding of the protein. Standard approaches were used to isolate and wash the inclusion bodies in a buffer to remove cellular contaminants followed by the solubilization of the pellets with 0.5% SDS as strong denaturant. The denaturant was then removed by rapid dilution and dialysis to allow the protein to refold to its native state. In order to avoid aggregation during the refolding process, polyethylene glycol (PEG) was added to the dilution buffer as a co-solvent which seemed to enhance the refolding of the 73K protein into a stable, soluble form.

Figure 10:
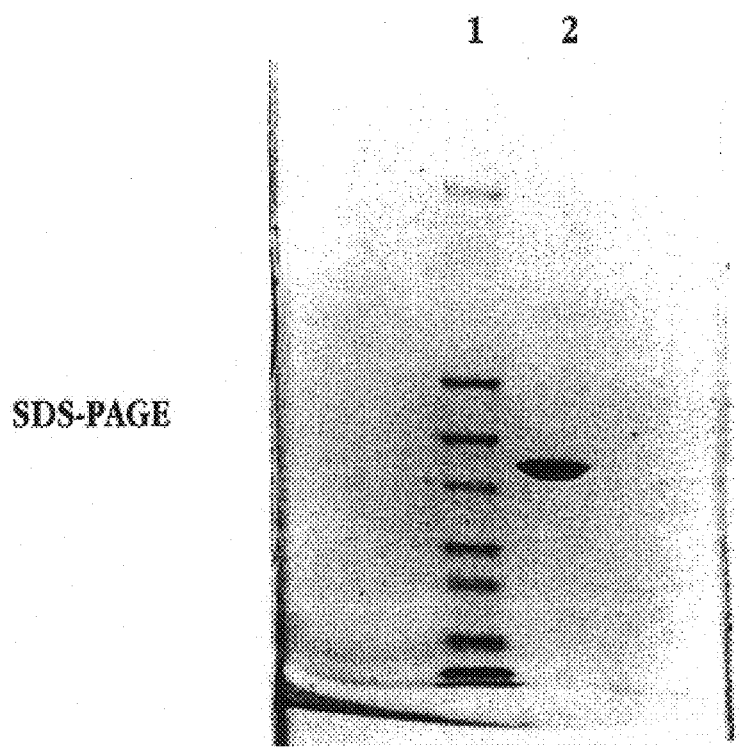
FIG. 10, "Final Purified 62K", shows purified soluble c62K protein run on a 4–20% SDS-PAGE. Lane 1, Novex "SeeBlue™" prestained MW standards; lane 2, final purified c62K protein. MW standards range as follows (top to bottom): myosin, 250-kDa; BSA, 98-kDa; glutamic dehydrogenase, 64-kDa; alcohol dehydrogenase, 50-kDa; carbonic anhydrase, 36-kDa; myoglobin, 30-kDa; lysozyme, 16-kDa; aprotinin, 6-kDa; insulin B chain, 4-kDa. The purification process for c62K is described in detail in Example 6B.

The final product of the c62K purification process in shown in FIG. 10. Details of the purification process are described in Example 6B. Briefly, the c62K/Sf9 cell lysate was spun out and the supernatant was then loaded onto an E. Merck DEAE EMD 650(S) column where the 62-kDa was captured and eluted at greater than 80% purity. The DEAE peak fractions were pooled and chromatographed on a Sephacryl S-100 column. Fractions containing c62K from the Sephacryl S-100 column were then purified and concentrated on a Poros HQ/F column. The protein band seen in lane 2 of FIG. 10 represents the final purified protein from the Poros HQ/F column.

In order to facilitate purification of the c62K protein, a reducing agent, e.g., DTT, was added to the lysis supernatant, followed by a two-step exchange of the reducing buffer to an initially lower reducing environment (50 mM DTT to 0.5 mM DTT) to a final nonreducing environment. Under these conditions potential aggregation of the c62K protein to contaminating cellular proteins is eliminated. The c62K protein is then easily recovered in a highly purified, homogenous form. Based on Coomassie blue stain, the estimated purity of both the 73K and c62K proteins to be 95 to 99 percent.

5. EVIDENCE OF VLPS-ELECTRON MICROSCOPY.

Figure 11A:
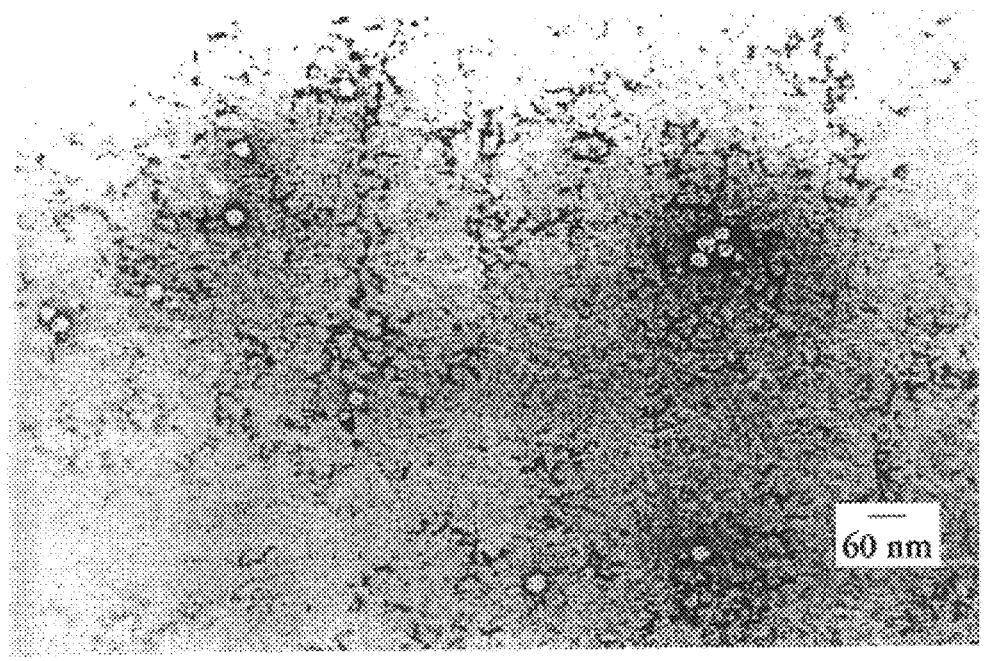
FIGS. 11a and 11b, show a comparison between electron micrographs of the purified recombinant ORF2 proteins c62K and 73K, respectively.
Figure 11B:
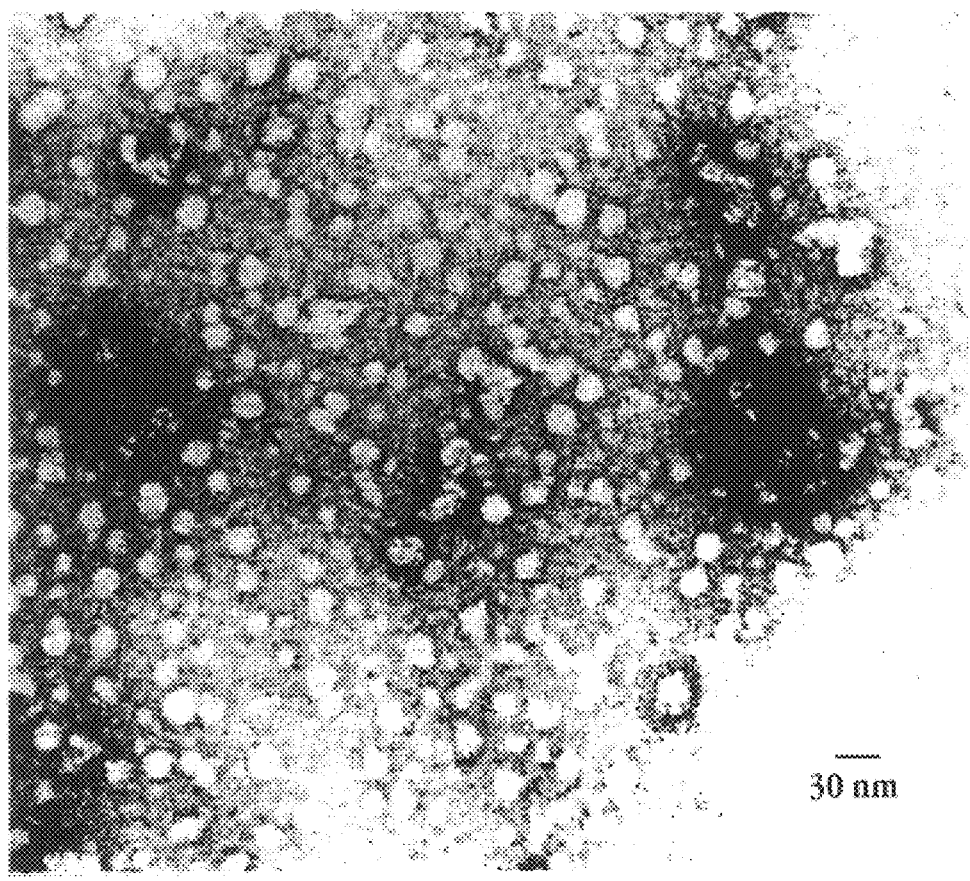

Purified recombinant 73K and c62K proteins were negative-stained and examined by direct electron microscopy (Example 7). Electron micrographs of c62K protein revealed determinant particles (FIG. 11A) approximately 30 nm in size which agrees well with published reports describing authentic virus particles (28–34 nm) found in stool and bile (Bradley, 1988; Reyes, 1993). Refolded 73K protein generated a range of pleiomorphic particles 25–40 nm in size, most of which exhibit indeterminant morphology (FIG. 11b).

6. N-TERMINAL SEQUENCE OF C62K PROTEIN.

The virus-like particle structure displayed by the purified c62K protein, as well as its solubility, suggested that this protein may exhibit a conformational structure similar to the native virion; i.e., a viral particle or virus-like particle. Accordingly, it was desirable to identify the coding sequence corresponding to the c62K protein, thus allowing subsequent expression in suspension cell culture that may permit the ability to by-pass the cleavage process for the production of this protein. For this reason, the N-terminal sequence analysis of purified c62K protein was performed.

The sequence of the first 10 amino acids sequenced was determined to be: Ala-Val-Ala-Pro-Ala-His-Asp-Thr-Pro-Pro. This sequence was perfectly homologous to amino acid residues starting at residue position 112 in ORF-2 (SEQ ID NO:13). Thus, the cleavage occurred between Thr and Ala which correspond to amino acids 111 and 112, respectively.

Thus, a c62K protein may be produced by transfecting insect cells with a baculovirus expression vector containing a nucleic acid sequence encoding the capsid protein of HEV. More generally, it will be appreciated that only the portion of the ORF2 nucleotide sequence, that encoding the c62K fragment (e.g., sequences encoding amino acids 112–660 derived from the ORF2 73K sequence; exemplary of such sequences are represented by SEQ ID NO:3 and SEQ ID NO:4), and homologous sequences therewith need be expressed as a protease will cleave the excess N-terminal amino acids to the c62K protein.

Other baculoviruses are known to those of skill in the art, for example, *Orygia pseudotsugata* is a commonly used vector. Baculoviruses have relatively narrow host ranges are generally confined to replication in Lepidopteran insect cells. Suitable Leptidopteran cell lines other than *Spodoptera frugiperda* are known to those of skill in the art, for example, *Lamantria dispar*, and *Helicos zea*.

It will also be appreciated by those skilled in the art that while the preferable expression system is a baculovirus expression system, the ORF2 sequence containing the coding region for the C-terminal 549 amino acids encoded by HEV ORF2 (relative to the Burma strain variant) may be expressed in other expression systems as well and may be cleaved by proteinases inherent in these systems, or they may be subsequently cleaved by a baculovirus infected cell extract in vitro. Further, the HEV capsid proteins may be obtained from HEV propagated in human or monkey liver in vivo or in vitro as described above, and that these capsid proteins may be cleaved with baculovirus infected insect cell lysate to form the 62K antigens as well.

Additionally, the cleavage site contained in the capsid protein may be used as an artifically inserted cleavage site for use in recombinant protein products, expression systems and industrial processes for making said products. For example, it is beneficial to construct recombinant proteins such that they are generated as fusion proteins. One benefit is that the fusion partner may be used as means for purifying the recombinant protein of interest. For example, one particularly useful fusion partner is a poly histidine fragment which is efficiently purified by means of a metal chelate affinity chromatography on NTA resin, described in U.S. Pat. No. 5,310,663, herein incorporated by reference. It is useful to have a cleavage site engineered in between the fusion partner and the recombinant protein such that the recombinant protein may be freed from the fusion partner after purification. Thus, the discovery of a novel baculovirus specific cleavage site provides an alternative to the conventional sites currently used for recombinant proteins produced in non-baculovirus systems.

The cleavage site may be advantageous for baculovirus systems as well. For example, a fusion partner useful for directing the new polypeptide to the cytoplasm may be preferentially cleaved once in the cytoplasm.

The boundaries defining the amino acids which comprise the cleavage site may be determined by techniques known to those skilled in the art. One such technique employs the use of site directed mutagenesis to alter individual amino acids flanking the cleavage site and subsequent testing of proteinase activity on the mutant peptides.

In addition, the identity of the baculovirus specific proteinase may be determined and its nucleic acid sequence cloned and expressed by techniques known to those skilled in the art. This will enable use of the specific proteinase in a purified form rather than baculovirus infected cell lysate.

7. RECOMBINANT PRODUCTION AND PURIFICATION OF A RE-ENGINEERED R62K HEV ANTIGEN.

Figure 5:
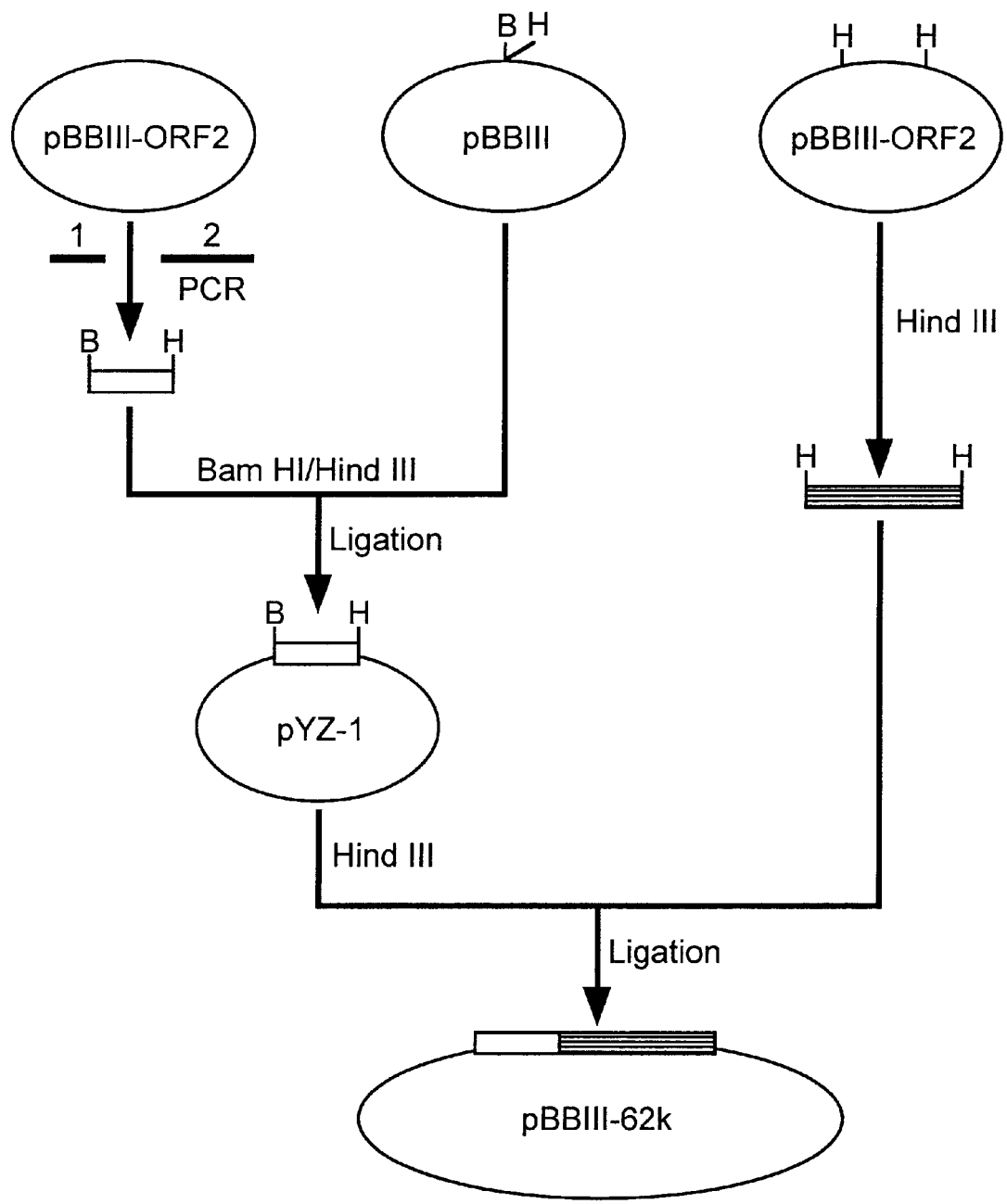
FIG. 5, presents a schematic diagram of the construction of a plasmid for expression of the re-engineered r62K antigen in baculovirus, showing a flow chart of the construction of pBBIII-62K. The bars represent the DNA fragments encoding r62K.

The question remained as to whether or not a "re-engineered" 62K protein species, referred to herein as r62K, would result in the formation of a stable protein with similar biochemical and structural properties to the processed form of c62K. Therefore, the DNA sequence from amino acid 112 to the last amino acid of the 3' end of ORF2 (Burma strain) was cloned into baculovirus expression vector pBluBacIII as shown in FIG. 5 and described in Example 4. A methionine codon was incorporated at 5' end to ensure proper translation initiation.

Figure 12:
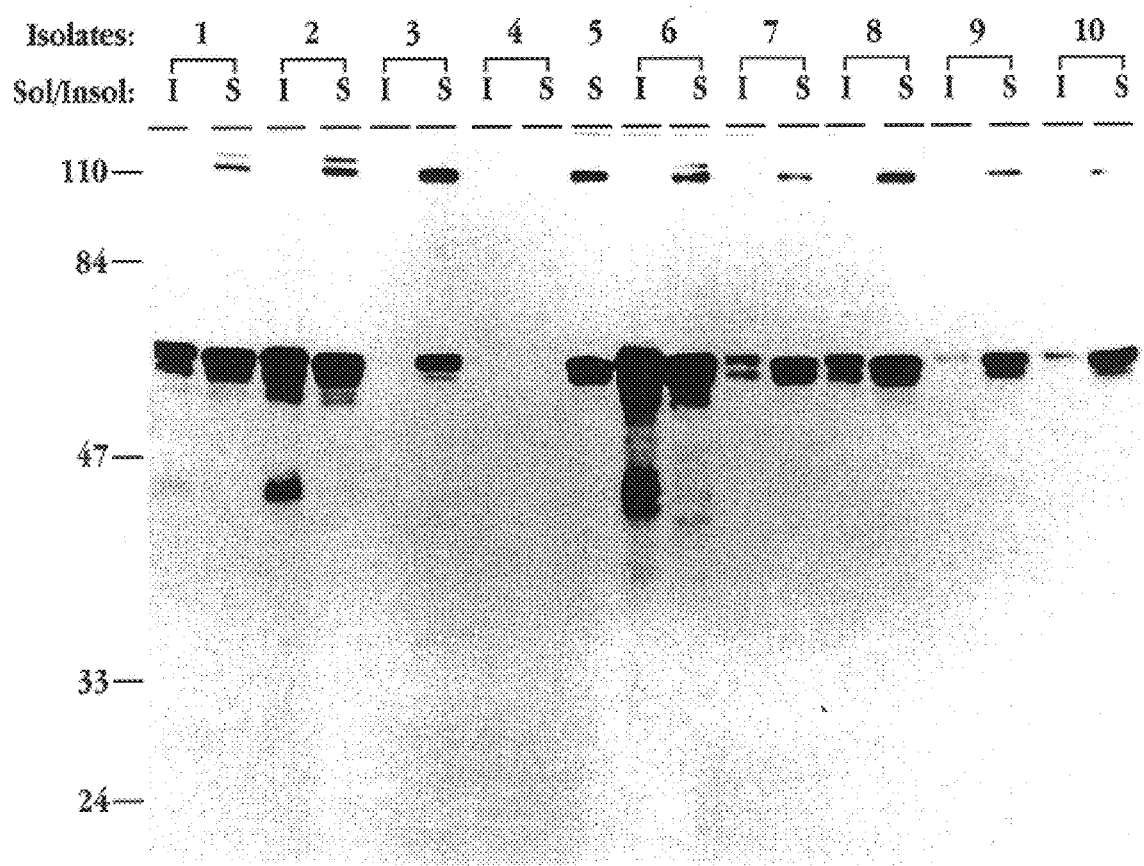
FIG. 12, "Expression Of ORF2-62K In Baculovirus", shows the expression of multiple isolates of BBIII-62K in suspension culture cells.

After transfection and 4 rounds of plaque purifications, viral stocks and cell lysates were prepared from 10 individual plaque isolates. Western blot analysis was performed to screen for the viral isolates which produced soluble r62K protein at the highest level (FIG. 12). Nearly all the viral isolates produced soluble r62K. The solubility of r62K ranged from approximately 60–70% of total extract. One isolate was chosen for amplification for further studies.

The r62K was found to be completely soluble in the lysis buffer with quantitative recovery of the molecule in the cell lysis supernatant. The lysis supernatant was subsequently processed through three chromatography steps to obtain purified r62K protein, according to Example 6b. The initial chromatography step was performed on an E. Merck DEAE EMD 650(S) column. It was found that the use of the EMD DEAE derivative enhanced recovery of the r62K relative to other similar weak anion exchange resins (Toyopearl 650 (S), DEAE Sepharose Fast Flow, etc.). The enhanced recovery was attributed to the "tentacle arm" structure of the E. Merck derivatized resin.

Further purification was achieved using a Sephacryl S-100 column which was used primarily for buffer exchange with some minor purification. The final material was obtained from peak fractions purified on a Poros HQ/F strong anion exchange resin.

The final material obtained by this procedure was determined to be greater than 95% pure and essentially endotoxin free by limulus amebocyte lysate assay. For purposes of Western blotting, the corresponding gel samples were diluted 1:10 prior to SDS-PAGE and transfer to PVDF membrane. The r62K band appears as a doublet which suggests the existence of a modified form of the r62K. N-terminal sequence analysis, peptide mapping, and mass spectroscopy data support the existence of a single primary amino acid sequence for the re-engineered 62K.

Further biochemical characterization of the purified 62-kDa protein was undertaken using a variety of methods (Example 9). Transfer of the recombinant 62-kDa sequence to PVDF and subsequent amino acid sequence analysis indicated that the amino terminus of the 62-kDa protein was intact with the exception that the N-terminal methionine introduced to ensure correct initiation of translation, had been removed. The overall yields in each of the first five cycles during sequencing were low, indicating that a significant portion of the 62-kDa was probably blocked at the amino terminus.

Tryptic peptide analysis revealed as many as 143 peaks by reverse phase HPLC. Eight peaks were selected for LDMS to determine structural integrity and potential post translational modifications (Example 9). Of these eight peaks, four gave rise to single species peptides. Three of these peptides matched various internal regions of the 62-kDa protein as determined by Edman degradation sequencing. One peak, peak 65, did not yield a sequence by Edman degradation. However, the molecular mass agreed very well with the predicted mass for the amino terminal tryptic peptide taking into account the removal of the N-terminal methionine by a cellular aminopeptidase followed by the acylation of the adjacent alanine residue. The results suggest that the amino terminus of the 62K antigen polypeptides are blocked— probably acetylated.

Post-source decay analysis by laser desorption mass spectrometry indicated that peak 65 was the amino terminal tryptic peptide (Example 9). The other four tryptic digest HPLC peaks which gave rise to multiple peptide species were also sequenced and provided further confirmation that the authentic HEV sequenced was preserved.

LC-MS data (Example 9) established the true molecular masses of the components of the 62-kDa doublet that was observed by Western blotting. With the elucidation of the of amino terminus in previous experiments, it was possible from ES-MS data to predict the putative carboxyl terminal processing steps that gave rise to the bimodally distributed '62-kDa' species.

The predicted molecular mass of the 62-kDa protein using the coding sequence of residue 112 to residue 660 of the ORF-2 region is 59.1-kDa. The protein was not found to be glycosylated both by periodate oxidation and GC-MS analysis. The data presented in Example 9 suggested that a deletion occurred in the molecule and that the deletion was likely at the amino or carboxyl terminus.

In combination with the confirmation of the amino terminus, the ES-MS data suggested that the carboxyl terminus may be clipped between residues 539–540 and residues 536–537 (relative to the predicted 62-kda protein sequence). Automated carboxyl terminal sequencing validated the carboxyl terminal processing of the protein and firmly established residues 539–540 (a 9 amino acid carboxy terminal deletion; e.g., SEQ ID NO:25 and SEQ ID NO:26) and 524–525 (a 23 amino acid carboxy terminal deletion; e.g., SEQ ID NO:27 and SEQ ID NO:28) as the carboxy termini of the 58.1-kDa and 56.5-kDa proteins respectively. Accordingly, the original 62K antigen isolated from insect cells is composed of these two related polypeptide species.

Thus the intended protein was expressed at high levels and purified to greater than 95% purity, although the apparent carboxy terminal processing was not anticipated. This processing did not appear to interfere with the ability of the protein to serve as an effective antigen, for example, the results presented in Table 1 (Example 9). In fact, the 62K antigen represents an improved antigen in comparison to bacterial expressed proteins in HEV diagnostic assays.

The excellent immunogenic properties of this antigen were also apparent from the ability of the 62K antigen preparation to elicit protective immune responses in primates after heterologous challenge with HEV (see Section IV below). These observations suggest that the baculovirus expressed protein may contain an immunologic structure that closely resembles the native virus capsid protein.

8. SIZE DETERMINATION OF 62K SUBUNIT VLPs.

Gel filtration is an attractive technique for the purification and analytical characterization of viral particles as it is much less time consuming than density gradient ultracentrifugation and permits chromatographic resolution and removal of particles larger or smaller than the desired viral particle. Sephacryl S-1000 Superfine has very high porosity which makes the resin suitable for applications involving the separation of viral particles, subcellular particles, and microsomal vesicles such as Percoll. The exclusion limits of S-1000 Superfine correspond to particles approximately 300–400 nm in diameter.

Figures 13, 16:
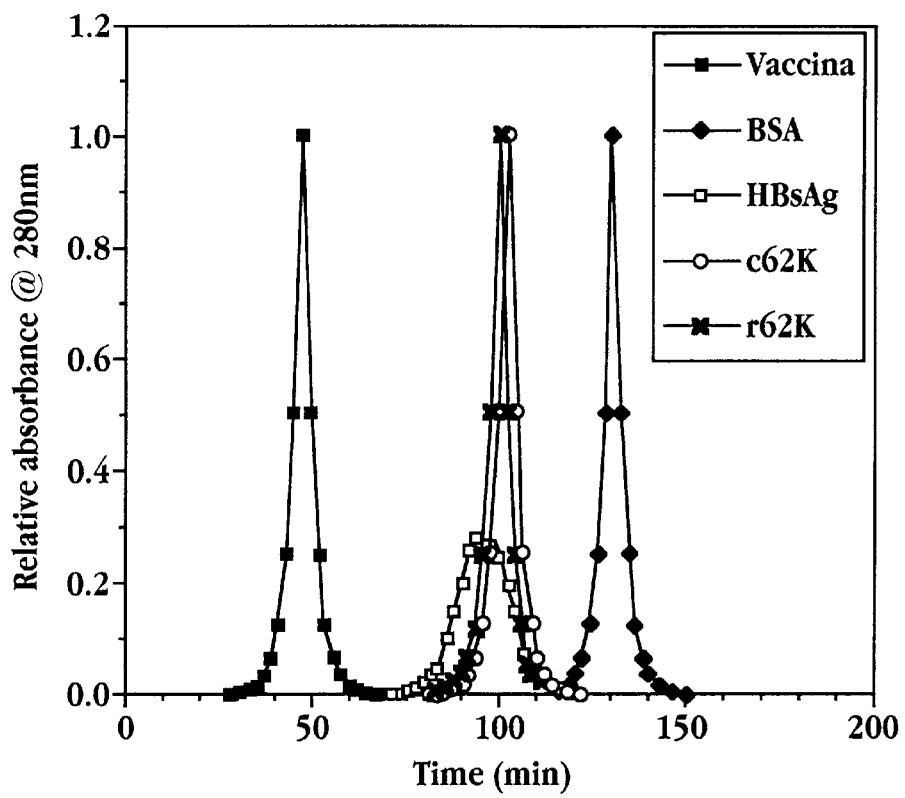
FIG. 13, "S-1000 Chromatography", shows the determination of re-engineered r62K and cleaved c62K viral particle size by Sephacryl S-1000 size exclusion chromatography. Virus particle standards (vaccinia virus and hepatitis B surface antigen, HBsAg), bovine serum albumin (BSA), and purified c62K and r62K preparations were chromatographed on a Waters AP-2 2×60 cm AP-2 column packed with Sephacryl S-1000 Superfine resin at a superficial linear velocity of 120 cm/hr. Retention times (minutes) and relative absorbance (280 nm) are indicated for the individual samples.
FIG. 16 shows a homology comparison between Burma (B) and Mexico (M) strains for the 406.4-2 antigen.

The absorbance profile of the Sephacryl S-1000 Superfine chromatography of the purified c62K and r62K virus particles is shown in FIG. 13. Elution of the c62K and r62K particles corresponded to the peaks having a retention times of 95–105 minutes. This corresponded to a particulate size of approximately 20–30 nm in diameter. The S-1000 column was also calibrated with three standards; two particulate, and one monomeric in structure. Vaccinia virus (250 nm) was found to have a retention time of approximately 48 minutes. Hepatitis B plasma derived surface antigen (HBsAg) particles (22 nm) were found to have a retention time of 95 minutes while bovine serum albumin (monomeric protein standard) had a retention time of 132 minutes.

The 62K antigens of the present invention (including the C-terminal 549 amino acids encoded by HEV ORF2 relative to the Burma strain variant and homologous sequences therewith) can similarly be prepared in other types of expression systems, preferably eucaryotic systems (e.g., mammalian and yeast), using the HEV genomic-insert plasmids above, with amplification of the desired sequences and cloning into a suitable expression vector. The coding sequences used in producing the re-engineered peptides can be derived from the cloning vectors described above and detailed elsewhere (Tam 1991-a), or from synthetic nucleotide synthesis using PCR splicing methods to join oligonucleotide fragments, according to known methods, in building up nucleotide sequences. Such modifications can be easily made by those of ordinary skill in the art.

62K antigens produced in this manner may be screened for antigenicity by the method described in Example 8. Briefly, the antigens are purified according to the method detailed in Example 6b, and plated onto wells of microtitre dishes. The polypeptides are washed with blocking solution and then reacted with sera known to contain anti-HEV antibodies. The unbound antibodies are washed away and a second antibody conjugated to a reporter molecule is then reacted with the peptide-antibody complexes. Results may be obtained, after washing away unbound second antibody, by detection of the reporter molecule.

62K antigens produced in this manner in accordance with the invention, are those that show substantially similar immunoreactivity to HEV positive sera as does a 62K antigen having the sequence of SEQ ID NO:15 produced in insect cells. Immunoreactivity is substantial similar when the percentage of sera samples that are reactive with both antigens is, preferably, greater than 80%, more preferably greater than 90%, and even more preferably greater than 95%.

F. Preparation of Antigenic Polypeptides and Antibodies

As described herein, the 62K antigen comprises mixtures of proteins (e.g., the 58.1-kDa and 56.5-kDa species, Examples 6 and 9) or individual polypeptides (e.g., SEQ ID NO:15, SEQ ID NO:16, SEQ ID NO:25, SEQ ID NO:26, SEQ ID NO:27 and SEQ ID NO:28) derived from the carboxy terminal 549 amino acids of ORF2 of HEV. One embodiment of the present invention, includes production of a 62K antigen containing two polypeptides obtained by expression of a coding sequence in insect cells (Examples 4 and 6). These two polypeptides contain carboxy terminal deletions relative to the carboxy terminal 549 amino acids of ORF2. Other expression systems can be used to produce the individual polypeptides or mixtures of polypeptides of the present invention.

For example, polynucleotide sequences encoding an antigen or antigens of the present invention can be cloned in the plasmid p-GEX or various derivatives thereof. The plasmid pGEX (Smith, et al., 1988) and its derivatives express the polypeptide sequences of a cloned insert fused in-frame to the protein glutathione-S-transferase (sj26). In one vector construction, plasmid pGEX-hisB, an amino acid sequence of 6 histidines is introduced at the carboxy terminus of the fusion protein.

The various recombinant pGEX plasmids can be transformed into appropriate strains of *E. coli* and fusion protein production can be induced by the addition of IPTG (isopropyl-thio galactopyranoside). Solubilized recombinant fusion protein may then be purified from cell lysates of the induced cultures using glutathione agarose affinity chromatography.

In the case of β-galactosidase fusion proteins (such as those produced by lambda gt11 clones) the fused protein may be isolated readily by affinity chromatography or by passing cell lysis material over a solid support having surface-bound anti-β-galactosidase antibody.

Also included in the invention is an expression vector, such as the lambda gt11 or pGEX vectors described above, containing sequences encoding the polypeptides of the present invention (e.g., SEQ ID NO:15/SEQ ID NO:16, SEQ ID NO:25/SEQ ID NO:26 and SEQ ID NO:27/SEQ ID NO:28, or a homologous sequence therewith) and expression control elements which allow expression of the coding regions in a suitable host. The control elements generally include a promoter, translation initiation codon, and translation and transcription termination sequences, and an insertion site for introducing the insert into the vector.

The DNA encoding the desired antigenic polypeptide can be cloned into any number of commercially available vectors to generate expression of the polypeptide in the appropriate host system. These systems include, but are not limited to, the following: baculovirus expression (Reilly, et al.; Beames, et al.; Pharmingen; Clontech, Palo Alto, Calif.), vaccinia expression (Earl, 1991; Moss, et al.), expression in bacteria (Ausubel, et al.; Clontech), expression in yeast (Gellissen, 1992; Romanos, 1992; Goeddel; Guthrie and Fink), expression in mammalian cells (Clontech; Gibco-BRL, Ground Island, N.Y.), e.g., Chinese hamster ovary (CHO) cell lines (Haynes, 1983, Lau, 1984, Kaufman, 1990). These recombinant polypeptide antigens can be expressed directly or as fusion proteins.

Expression in yeast systems has the advantage of commercial production. Recombinant protein production by vaccinia and CHO cell line have the advantage of being mammalian expression systems. Further, vaccinia virus expression has several advantages including the following: (i) its wide host range; (ii) faithful post-transcriptional modification, processing, folding, transport, secretion, and assembly of recombinant proteins; (iii) high level expression of relatively soluble recombinant proteins; and (iv) a large capacity to accommodate foreign DNA.

The recombinant expressed polypeptide antigens are typically isolated from lysed cells or culture media. Purification can be carried out by methods described herein.

Antigens obtained by any of these methods can be used for antibody generation, diagnostic tests and vaccine development.

In another aspect, the invention includes specific antibodies (polyclonal or monoclonal) directed against the polypeptide antigens of the present invention. For example, purified antigen or fused antigen protein may be used for producing monoclonal antibodies. Here the spleen or lymphocytes from an immunized animal are removed and immortalized or used to prepare hybridomas by methods known to those skilled in the art (Harlow, et al.). To produce a human-derived hybridoma, a human lymphocyte donor is selected. A donor vaccinated with the polypeptides of the present invention may serve as a suitable lymphocyte donor. Lymphocytes can be isolated from a peripheral blood sample. Epstein-Barr virus (EBV) can be used to immortalize human lymphocytes or a suitable fusion partner can be used to produce human-derived hybridomas. Primary in vitro sensitization with viral specific polypeptides can be used in the generation of human monoclonal antibodies.

Antibodies secreted by the immortalized cells are screened to determine the clones that secrete antibodies of the desired specificity, for example, by using the ELISA or Western blot methods.

In another aspect, the present invention includes nucleic acid molecules (e.g., DNA or RNA) that encode the polypeptide antigens of the present invention.

G. SYNTHETIC PRODUCTION OF HEV PEPTIDES

In addition to the procedures for producing the peptides described above, peptides of up to about fifty amino acids in length may be produced by conventional solid phase synthesis methods. Such methods are known to those skilled in the art. Peptides produced in this manner may be covalently linked to other peptides or protein conjugates or moieties, as would be formed, for example, recombinantly in a fusion protein.

III. DIAGNOSTIC METHOD

In a related aspect, the invention is directed to a method of diagnosing individuals with HEV infections wherein HEV derived peptide antigens are used to examine an individual's serum for the presence of anti-HEV antibodies.

A. IMMUNOREACTIVITY OF HEV ANTIGENS

Following production of HEV antigens, in accordance with the invention, serum samples from individuals known to be infected with HEV are tested for their ability to bind to such antigens. Assays for antibody-antigen binding are well known in the art (Harlow, 1988). Solid-phase assays, such as enzyme-linked immunosorbent assay (ELISA) binding assays are particularly suitable for measuring antibody-peptide antigen binding. Such assays may be carried out in direct or competitive binding assay format. In the direct method, the test peptide is adsorbed to a solid phase. Test anti-HEV antisera is added to the peptide, and binding of human antibody to the peptide is measured, for example, as in the method of Example 8.

Alternatively, when peptides are expressed as fusion proteins of sufficient size to be retained by an SDS-PAGE, western blots may be used to determine binding of the peptide portion of the fusion protein to a serum sample.

Clones 406.3-2(M) and 406.4-2(M) were shown to encode immunoreactive peptides in co-owned U.S. patent application, Ser. No. 07/505,888, incorporated herein by reference. In continuing studies with these peptides and their analogs from the Burma strain, with HEV-positive human sera (from five different epidemics), peptide 406.3-2(M) was immunoreactive with eight of eleven samples tested, peptide 406.4-2(M) was immunoreactive with nine of eleven samples tested, and peptides 406.3-2(B) and 406.4-2 were both immunoreactive with all six of six samples tested Yarbough 1991, herein incorporated by reference. A description of experiments leading to the above results may be found in Example 1. Peptide antigen SG3 was shown to be highly immunoreactive with infected sera in co-owned U.S. patent application, Ser. No. 08/240,049, filed May 9, 1994.

In the present invention, to evaluate the antigenicity of a purified c62K protein preparation, immunoassays were performed using a panel of human acute phase and convalescent phase sera taken during various hepatitis E epidemics. Sera were tested by ELISA for IgG and IgM antibodies to HEV according to the method of Example 8. Three antigens derived from the putative capsid protein of HEV were used: (1) SG3, 327 amino acids of ORF2 (SEQ ID NO:17) expressed in *E. coli*; (2) 73K, 660 amino acids of ORF2 (SEQ ID NO:13) expressed in baculovirus; and (3) c62K, 549 amino acids of ORF2 (SEQ ID NO:15) processed by a baculovirus proteinase(s).

Serum samples were from confirmed and suspected hepatitis E cases in endemic regions. As shown in Table 1 below, the c62K protein expressed in baculovirus detected measurable antibody to HEV in several pedigreed specimens from acute hepatitis E cases that would have gone undetected when using SG3, the best HEV antigen expressed in *E. coli* (Yarbough 1994). Specimens that tested positive to only the c62K antigen are denoted by an asterisk. For IgG anti-HEV, 3/18 serum samples (17%) scored as antibody positive uniquely with the c62K protein. For IgM anti-HEV, 7/18 serum samples (39%) scored as antibody positive uniquely with the c62K protein. In most cases, the O.D. values suggested that the anti-HEV detected by the SG3 protein or the 73K protein were just below the threshold of credible detection.

TABLE 1

COMPARATIVE ANTIGENICITY STUDIES
*E. coli* and Baculovirus Expressed Proteins

|  | SG3 | c62K | 73K |
| --- | --- | --- | --- |
| ELISA FOR ANTI-HEV IgG |  |  |  |
| Borneo S89 | 0.895 | 2.579 | 1.077 |
| FVH 3 | 0.338 | 1.298 | 0.374 |
| FVH 11 | 1.237 | 2.416 | 1.247 |
| FVH 26 | 0.397 | 1.353 | 0.571 |
| FVH 29 | 0.515 | 1.051 | 0.540 |
| FVH 31 | 0.401 | 2.474 | 0.494 |
| MB0283 | 2.602 | 2.771 | 2.558 |
| MB0288 | 2.088 | 2.506 | 2.311 |
| Som 002 | 1.357 | 2.616 | 1.301 |
| Som 010 | 2.489 | 2.617 | 2.588 |
| Som 032 | 2.456 | 2.503 | 2.351 |
| Som 055 | 1.930 | 2.386 | 1.539 |
| *Som 428 | 0.284 | 1.687 | 0.312 |
| *Som 443 | 0.246 | 0.727 | 0.337 |
| *Som 458 | 0.206 | 2.441 | 0.257 |
| Som Pool #3 | 2.305 | 2.474 | 2.235 |
| Sudan 54 | 2.159 | 2.717 | 2.310 |
| Sudan 60 | 2.264 | 2.541 | 2.402 |
| ELISA FOR ANTI-HEV IgM |  |  |  |
| *Boreno S89 | 0.237 | 2.527 | 0.356 |
| FVH 3 | 0.064 | 0.164 | 0.061 |
| *FVH 11 | 0.091 | 0.405 | 0.115 |
| *FVH 26 | 0.077 | 0.319 | 0.069 |
| *FVH 29 | 0.149 | 0.493 | 0.115 |
| FVH 31 | 0.080 | 0.223 | 0.061 |
| *MB0283 | 0.123 | 0.892 | 0.147 |
| *MB0288 | 0.083 | 0.335 | 0.090 |
| Som 002 | 0.508 | 2.598 | 0.681 |
| Som 010 | 0.534 | 2.526 | 0.939 |
| Som 032 | 0.722 | 2.861 | 0.877 |
| Som 055 | 1.342 | 2.560 | 1.283 |
| Som 428 | 1.165 | 2.463 | 0.863 |
| Som 443 | 0.411 | 1.106 | 0.392 |
| *Som 458 | 0.279 | 1.525 | 0.248 |
| Som Pool #3 | 0.942 | 2.397 | 1.428 |
| Sudan 54 | 0.532 | 2.652 | 0.754 |
| Sudan 60 | 0.396 | 0.529 | 0.414 |

Altogether the results demonstrated that the sensitivity and specificity of the assay was significantly improved using c62K as an antigen source. This observation suggests that structural determinants present on c62K recognized by anti-HEV antibodies engendered during a natural infection more closely resemble the native virion as opposed to the baculovirus 73K and *E. coli* expressed recombinant proteins. Taken collectively, the 62K antigen is a significant advancement for detecting low levels of antibody directed to the hepatitis E virus.

B. COMPARISON OF IMMUNOREACTIVITY BETWEEN C62K AND R62K

Comparative ELISA assays were performed to measure the antigenic similarities between these two proteins and further support the correspondence of the r62K and c62K protein preparations. In accordance with the method of Example 8, equivalent amounts of c62K and r62K proteins were used to measure the antigenic similarities between these two protein preparations. IgG anti-HEV detection with miscellaneous serum samples showed that cleaved (c) and re-engineered (r) 62K protein species were comparable in their specificity and sensitivity to detect anti-HEV (Table 3, below).

TABLE 2

COMPARATIVE ANTIGENICITY STUDIES
Endpoint Titrations for *E. coli* and
Baculovirus Expressed Proteins ELISA FOR ANTI-HEV IgG

|  | SG3 | r62K | 73K |
| --- | --- | --- | --- |
| Cyno 9004 | 1:1000 | 1:5000 | 1:500 |
| Chimp Rusten | 1:500 | 1:5000 | 1:200 |
| K. Sa | 1:1000 | 1:5000 | 1:500 |
| A. Za | 1:200 | 1:5000 | nd |
| Mex 387 | 1:2500 | 1:10000 | 1:1000 |
| Sudan 60 | 1:1000 | 1:5000 | 1:500 |
| ABTD 80 | 1:1000 | 1:25000 | 1:200 |
| Som Pool | 1:1000 | 1:25000 | 1:200 |

ELISA FOR ANTI-HEV IgM

|  | SG3 | 62K | 73k |
| --- | --- | --- | --- |
| Cyno 9004 | nd | nd | nd |
| Chimp Rusten | nd | 1:1000 | nd |
| K. Sa | nd | 1:200 | nd |
| A. Za | 1:100 | 1:2000 | nd |
| Mex 387 | nd | 1:200 | nd |
| Sudan 60 | nd | nd | nd |
| ABTD 80 | 1:200 | 1:5000 | nd |
| Som Pool | 1:100 | 1:5000 | nd |

C. SENSITIVITY OF THE R62K ANTIGEN

A small subset of human and non-human primate sera was diluted and assayed for anti-HEV IgG and IgM to define the sensitivity of the r62K protein preparation (Table 2, above). Diluted sera were tested with each of the *E. coli* and baculovirus expressed antigens. The ELISA endpoint was defined as the greatest dilution of sera that still permitted a positive result in the assay. Endpoint titration data established that the r62K protein has a limit of detection for anti-HEV IgG that minimally exceeds 5-fold that of the currently used *E. coli* expressed SG3 antigen. The detection of anti-HEV IgM was consequentially increased 25-fold by using the r62K protein preparation as the antigen of choice. The 62K antigen is a significant advancement for detecting low levels of antibody directed to the hepatitis E virus.

TABLE 3

COMPARATIVE ANTIGENICITY STUDIES
Cleaved and Re-engineered Baculovirus Expressed Proteins
ELISA for anti-HEV IgG

|  | c62K | r62K | 73K |
| --- | --- | --- | --- |
| Confirmed cases in endemic regions |  |  |  |
| ABTD 80 | 2.212 | 2.229 | 0.344 |
| ABTD 86 | 1.689 | 2.399 | 0.309 |
| MB 2/88 | 2.083 | 1.961 | 0.724 |
| Mex F387 | 2.664 | 2.635 | 1.069 |
| Som Pool | 1.679 | 2.264 | 0.342 |
| Sudan 60 | 2.493 | 2.298 | 1.024 |
| Travellers to endemic regions |  |  |  |
| A. Za (1/100) | 1.598 | 1.887 | 0.138 |
| A. Za (1/500) | 0.807 | 1.060 | 0.045 |
| K. Sa (1/100) | 1.983 | 1.905 | 0.800 |
| K. Sa (1/500) | 1.226 | 1.314 | 0.219 |
| B. Ka (1/100) | 0.097 | 0.080 | 0.105 |
| B. Ka (1/500) | 0.058 | 0.050 | 0.054 |
| S. Ha (1/100) | 0.116 | 0.122 | 0.122 |
| S. Ha (1/500) | 0.088 | 0.062 | 0.047 |
| Sporadic cases-acute hepatitis |  |  |  |
| HEP 31 | 0.071 | 0.075 | 0.078 |
| HEP 35 | 0.541 | 0.542 | 0.157 |
| HEP 69 | 0.085 | 0.090 | 0.086 |
| HEP 28 | 0.087 | 0.083 | 0.090 |

IV. THERAPEUTIC APPLICATIONS

The in vivo immunogenic efficacy of the ORF2 62K antigen to confer protection against a heterologous challenge was investigated (Example 11). The r62K antigen (Examples 4, 6 and 9) was used to inoculate cynomolgus macaques that were subsequently challenged with the heterologous HEV Mexico strain. The results indicate that this candidate antigen may be useful in developing a vaccine to prevent acute hepatitis E in developing countries and to provide protection for travellers to disease-endemic regions.

Immunization of cynos with the ORF2 r62K protein protected against subsequent heterologous wildtype HEV infection and disease. Accepted criteria for evidence of HEV infection and virus replication include: (1) detection of HEV antigen in the liver, (2) detection of HEV RNA in the feces or serum, (3) seroconversion to HEV antibody positive. Hepatitis E disease is defined as HEV infection and (1) a rise in ALT levels greater than two standard deviations above baseline and (2) histopathology compatible with viral hepatitis.

Experiments performed in support of the present invention demonstrate that animals immunized with a recombinant capsid protein derived from the HEV Burma strain are protected from challenge with wild-type virus of the divergent HEV Mexico strain. There were no significant elevations in liver enzymes and no histopathologic evidence for hepatocellular damage in any of the three immunized animals. Vaccination thus conferred protection against disease in all the cynos immunized with r62K.

For two of the three vaccinated animals, full protection against HEV infection was substantiated by the absence of measurable viral antigen in the liver or viral RNA in the stool. Further, in these two animals neutralizing antibodies were demonstrated to be present (Example 11, FIG. 15). The partial protection against infection in one cyno, as evidenced by the delayed and transient presence of viral RNA in the stool, may be related to the relatively low levels of measurable anti-HEV antibodies. Nevertheless, in the absence of necro-inflammatory changes, it appears that hepatitis was prevented by immunization with the r62K vaccine, although complete protection from infection was not acheived in this one animal.

When required, levels of neutralizing antibodies may be increased by use of higher doses of antigen and/or repeated inoculations prior to challenge with infectuous virus. Such repeated inoculations are currently used for vaccination against, for example, hepatitis A virus (HAV) and hepatitis B virus (HBV).

Both the results, in the vaccinated animals and in the animals used to titrate the challenge inoculum virus, support that the development of HEV infection and associated disease are dependent on a threshold effect related to the amount of the inoculum and the presence and characteristics of a pre-existing specific immune response. In the titration study using HEV infected animals, the extent of hepatitis was related and the timing to onset of ALT elevations was inversely related to the amount of inoculum received.

In the vaccine portion of the study, the results with cyno 9330 suggest that although HEV infection was not prevented, the presence of HEV specific immunity at the time of challenge resulted in a limited infection characterized by a delayed latency to onset of detectable virus replication, a shortened duration of detectable viral replication and the absence of characteristic features of HEV induced disease.

In a previous study (Purdy et. al., 1993), immunization with a truncated version of HEV Burma ORF2, trpE-C2, expressed in E. coli afforded variable degrees of protection for HEV infection and disease. One cyno was reported to be fully protected against virus infection and hepatitis after homologous strain wild-type challenge. However, animals challenged with the heterologous HEV Mexico strain were only partially protected. Although one immunized cyno appeared to be protected from hepatitis, the animal had evidence of viral antigen in the liver and viral RNA in the stool after heterologous wild-type challenge.

The data described in the present specification definitively establishes for the first time the feasibility of developing an effective vaccine for hepatitis E capable of providing cross-protection for the most divergent HEV strains isolated and characterized to date. Within the 549 amino acids expressed in a "62K" ORF2 vaccine candidate, there are 31 amino acids changes between the Burma and Mexico strains (Tam, et al., 1991; Huang, et al., 1992) and no more than 4 amino acid changes between the more closely related Burma, China, and Pakistan strains (Tsarev, et al., 1992).

V. HEV SPECIFIC PEPTIDE ANTIGENS FOR HEV ASSAYS

This section describes the peptide antigens which are employed in the assay kit and assay method described in Section VI below.

In accordance with the invention, HEV antigens, characterized as useful for diagnosis of HEV herein, include the 62K (B) or (M) antigen consisting of, for example, an amino acid sequence selected from the group consisting of SEQ ID NO:15/SEQ ID NO:16, SEQ ID NO:25/SEQ ID NO:26 and SEQ ID NO:27/SEQ ID NO:28, or a homologous sequence therewith. The 62K antigen may be produced by cleavage of either native or recombinant ORF2 derived proteins with a protease, preferably a baculovirus protease. Alternatively the 62K antigen may be re-engineered and expressed in a recombinant expression system. Re-engineered 62K antigen or "r62K" preferably contains a methionine at the N-terminus and is preferably produced by a baculovirus expression vector in an insect cell.

The 62K antigens are derived from the carboxyl-terminal 549 residues of the capsid protein which is encoded by open reading frame-2 (relative to Burma strain). These peptide antigens can be prepared as described in Section II above and in Example 4 which follows.

Studies conducted in support of the present invention, discussed above, demonstrate that the 62K antigen is specific for HEV; i.e., 62K immunoreacts with antibodies present in the serum of HEV infected individuals. The antigen may not detect all HEV positive sera, and may pick up some false positives; i.e., non-infected individuals. The 62K antigen derived from the Mexico strain (or other variant strains) of HEV can be expected to be specifically immunoreactive with HEV positive sera.

Several peptide antigens have been previously characterized in co-owned U.S. patent applications "Enterically Transmitted Non-A/Non-B Hepatitis Viral Agent and Characteristic Epitopes Thereof", Ser. No. 07/420,921, filed Apr. 5, 1990, now abandoned, and "HEV Peptides and Methods", Ser. No. 08/240,049 both of which are incorporated herein by reference. These peptides form part of the present invention when used in assays in combination with the 62K antigens.

A first antigen in the group of previously characterized HEV peptide antigens contains the epitope formed by the 406.4-2(B) peptide (SEQ ID NO:19), or the 406.4-2(M) peptide (SEQ ID NO:20). Also contemplated are peptide antigens containing the epitope formed by an amino acid sequence homologous with or an internally consistent variation between SEQ ID NO:19 and SEQ ID NO:20. This first peptide antigen is derived from the carboxyl terminus of the protein encoded by open reading frame-3. A second peptide antigen contains the epitope formed by the 406.3-2(B) peptide (SEQ ID NO:23) or the 406.3-2(M) peptide (SEQ ID NO:24). Also contemplated as a second peptide antigen are peptide antigens containing the epitope formed by an amino acid sequence homologous with or an internally consistent variation between SEQ ID NO:11 and SEQ ID NO:12. A third peptide antigen contains the epitope formed by the SG3(B) peptide (SEQ ID NO:17) or the SG3(M) peptide (SEQ ID NO:18). Also contemplated as a third peptide antigen are peptide antigens containing the epitope formed by an amino acid sequence homologous with or an internally consistent variation between SEQ ID NO:17 and SEQ ID NO:18. These second and third peptide antigens are derived from the carboxyl terminus of the capsid protein encoded by open reading frame-2. FIG. 3 shows the sequence of the 406.4-2(B) and (M) peptides and FIG. 4 shows the sequence of the 406.3-2(B) and (M) and SG3(B) and SG3(M) peptides. Methods for obtaining the confirmatory peptides are described above and detailed in the following Examples.

In accordance with the present invention, reactivity of antibodies in a serum sample taken from an individual suspected of being infected with a causative agent of hepatitis to a 62K antigen is a reliable method for diagnosing the causative agent as HEV. Also forming part of the present invention, reactivity to the known peptides used in conjunction with a 62K antigen may enhance the sensitivity and reliability of the diagnostic method described below.

VI. Utility

This section describes uses of the antigenic peptides and proteins of the invention as diagnostic reagents for diagnosing hepatitis E viral infection and in vaccine compositions for protecting an individual from infection with HEV.

A. Diagnostic Methods and Kits

Three basic types of diagnostic applications of the antigens will be described. The first is based on inhibition of complement-mediated, antibody-dependent cytolysis by the antigen. In this method, serum from a test individual is reacted with HEV-infected cultured human hepatocytes in the presence of complement. The presence of anti-HEV antibody is evidenced by cell lysis, as judged, for example, by trypan blue dye exclusion. Where cell lysis is observed, the specificity of the anti-HEV antibody for the HEV antigen is demonstrated by first reacting the serum with excess antigen, then mixing the serum with the cells in the presence of complement. Antibody specificity is indicated by a substantial decrease in cell lysis. The method can also be used to quantitate the antibody titre in the analyte serum, by titrating the serum with increasing amounts of antigen concentration where a noticeable effect on the extent of cell lysis is first observed.

The second general assay type is a solid-phase immunoassay. In this method, a solid phase reagent having surface-bound antigen is reacted with analyte serum, under conditions which allow antibody binding to the antigen on the reagent. After washing the reagent to remove unbound serum components, the reagent is reacted with reporter-labeled anti-human antibody to bind reporter to the reagent in proportion to the amount of bound anti-HEV antibody on the solid support. The reagent is again washed to remove unbound labeled antibody, and the amount of reporter associated with the reagent is determined. Typically, as in the system described in Example 1, the reporter is an enzyme which is detected by incubating the solid reagent in the presence of a suitable fluorometric or calorimetric substrate. However, radiolabel and other reporters may be used.

After reacting the analyte serum with the solid-phase bound antigen and washing to remove the unbound serum components, one may alternatively use the antigen itself bound to reporter as a detection reagent instead of using an anti-human antibody as a reporter mediator. The competitive assay takes advantage of antibody bivalency. The same reporters may be used in this embodiment of the solid-phase assay as was described above.

Multiple antigens may be used in conjunction or in tandem in each of the assays described above. In addition, reaction to each antigen may be distinguished. For example, in the solid-phase assay described above, two or more different antigens may be bound to solid phase in separate locations so that reaction to each antigen may be quantitated separately. Alternatively, antigens labeled with distinguishable reporters may be used to detect antigens which are interspersed on the solid support.

The solid surface reagent in the above assay is prepared by known techniques for attaching protein material to solid support material, such as polymeric beads, dip sticks, or filter material. These attachment methods generally include non-specific adsorption of the protein to the support or covalent attachment of the protein, typically through a free amine group to a chemically reactive group on the solid support, such as an activated carboxyl, hydroxyl, or aldehyde group.

The third general assay type is a homogeneous assay, in which antibody binding to a solid support produces some change in the reaction medium. Known general types of homogeneous assays proposed heretofore include: (a) spin-labeled reporters, where antibody binding to the antigen is detected by a change in reporter mobility (broadening of the spin splitting peaks); (b) fluorescent reporters, where binding is detected by a change in fluorescence efficiency; (c) enzyme reporters, where antibody binding effects enzyme/substrate interactions; and (d) liposome-bound reporters, where binding leads to liposome lysis and release of encapsulated reporter. The adaption of these methods to the antigens of the present invention follows conventional methods for preparation of homogeneous assay reagents.

In each of the three general assays described above, the assay method involves reacting the serum from a test individual with the antigen, and examining the antigen for the presence of bound antibody. In the first assay, the examining is done by observing the decrease in antibody-mediated cytolysis, when the antibody is bound to the antigen. In the solid-phase assay, the examining involves attaching a labeled anti-human antibody (or labeled antigen) to the antibody being examined, and measuring the amount of reporter bound to the solid support. And in the third assay type, the examining is done by observing the effect of antibody binding on a homogeneous assay reagent.

B. VACCINE COMPOSITIONS AND METHODS

1. PREPARATION OF VACCINE COMPOSITIONS.

The recombinant or cleaved 62K antigens described above are incorporated into a vaccine composition, according to known procedures, to enhance the antigenicity of the injected antigens.

In one composition, the HEV antigen is covalently coupled to a carrier protein, such as keyhole limpet hemocyanin, and injected either in solution form or in combination with an adjuvant. Alternatively, where the HEV antigen is prepared as part of a fusion protein, the non-HEV moiety of the protein may serve as the carrier protein.
The derivatized or fusion protein is carried in a pharmaceutically acceptable carrier, such as in solution or in an adjuvant, such as converted alum.

Alternatively, the free antigen itself, e.g., the HEV 62K antigen, may be formulated in alum or used without adjuvant. A suitable adjuvanted vaccine has a preferred antigen concentration of about 1 mg antigen/mg alum, and not to exceed 80 mg of alum per injection.

2. ANTIGEN VACCINE METHOD.

In a related aspect, the invention is directed to a method of inhibiting infection of an individual by hepatitis E virus, by administering to the subject, by parenteral injection, e.g., intramuscular or intravenous injection, the vaccine composition of the invention.

Preferred vaccine compositions, for use in the method are those in which the HEV antigen includes the sequence in the peptides identified by: SEQ ID NO:15; SEQ ID NO:16, SEQ ID NO:25, SEQ ID NO:26, SEQ ID NO:27 and SEQ ID NO:28 with or without an amino terminal methionine and homologous sequences therewith. The antigen vaccine composition is preferably administered intramuscularly in a series of inoculations, for example, two to three injections each given at four week intervals.

Individual dosages of the vaccine composition are administered in a therapeutically effective amount. Such dosages are determined by physicians, for example, based on clinical trial data. Exemplary dosage ranges for the vaccine composition are about 0.05 $\mu$g to 1 mg, preferably about 0.1 $\mu$g to 30 $\mu$g. Individual dosages may contain a single 62K antigen polypeptide or multiple polypeptides derived from the 549 amino acid carboxy terminal region of HEV ORF2. In addition, such 62K antigens may be combined with other known HEV antigenic polypeptides for vaccine formulations.

The 62K antigen preparation of the present invention may be useful to (i) prevent epidemics and sporadic cases of hepatitis E in developing countries, (ii) protect pregnant women at risk in disease endemic regions, and (iii) provide protection to travellers to those regions. The in vitro and in vivo experiments described herein can be used to determine the optimal immunization regime with the 62K antigen preparation.

As discussed above, the 62K antigens of the present invention can be used in vaccine preparation. Further, antibodies generated against the polypeptide antigens of the present invention can be used for passive immunotherapy or passive immunoprophylaxis. Antibodies directed against the antigens of the present invention can be administered in amounts similar to those used for other therapeutic administrations of antibody. For example, pooled gamma globulin is administered at 0.02–0.1 ml/lb body weight during the early incubation of other viral diseases such as rabies, measles and hepatitis B to interfere with establishment of infection. Thus, antibodies reactive with the 62K antigens can be passively administered alone or in conjunction with another anti-viral agent to a host infected with HEV to enhance the ability of the host to deal with the infection.

The usefulness and efficacy of the above described therapeutic methods can be evaluated in vitro, using the cell systems described above, and in vivo, using the animal model systems described above.

The following examples, which illustrate various methods and compositions in the invention, are intended to illustrate, but not limit the scope of the invention.

MATERIALS

Enzymes: DNAse I and alkaline phosphatase were obtained from Boehringer Mannheim Biochemicals (BMB, Indianapolis, Ind.); EcoRI, EcoRI methylase, DNA ligase, and DNA Polymerase I, from New England Biolabs (NEB, Beverly Mass.); and RNase A was obtained from Sigma (St. Louis, Mo.).

Other reagents: EcoRI linkers were obtained from NEB; and nitro blue tetrazolium (NBT), 5-bromo-4-chloro-3-indolyl phosphate (BCIP), 5-bromo-4-chloro-3-indolyl-B-D-galactopyranoside (Xgal), p-Nitrophenyl phosphate, and isopropyl B-D-thiogalactopyranoside (IPTG) were obtained from Sigma. cDNA synthesis kit and random priming labeling kits are available from Boehringer-Mannheim Biochemical (BMB, Indianapolis, Ind.).

Cloning and Expression vectors such as pBluescript™ (pBS), can be obtained from Stratagene Cloning Systems (La Jolla, Calif.), the pGEX™ expression vector can be obtained from Pharmacia (Piscataway, N.J.), and the pBlu-BacIII can be obtained from Invitrogen (San Diego, Calif.).

Immunodiagnostic Test Kits for Hepatitis A Virus (HAV), Hepatitis B Virus (HBV), Hepatitis C Virus (HCV), are available from Abbott Diagnostics (Abbott Park, Ill., USA). Immunodiagnostic Test Kits for Hepatitis E Virus (HEV) are available from Genelabs Diagnostics USA (Redwood City, Calif.).

DEAE EMD 650(S) was obtained from E. Merck Separations (Darmstadt, Germany). Sephacryl S-100 and S-1000 were obtained from Pharmacia Biotech (Piscataway, N.J.). Poros Q/F and HQ/F chromatography columns were obtained from PerSeptive Biosystems (Cambridge, Mass.). Buffer ingredients were obtained from AMRESCO (Solon, Ohio) and proteins were purified on a Waters 650E chromatography workstation (Milford, Mass.) with data management provided by Millennium 2010 software (Milford, Mass.).

EXAMPLE 1

Preparation of 406.3-2, 406.4-2, and SG3 Antigens

A. PRODUCTION OF RANDOM HEV DNA FRAGMENTS.

A pBET1 plasmid (Tam, et al., 1991a) was digested with EcoRI to release the insert which was purified from the linearized plasmid by gel electrophoresis. The purified fragment was suspended in a standard digest buffer (0.5M Tris HCl, pH 7.5; 1 mg/ml BSA; 10 mM MnC12) to a concentration of about 1 mg/ml and digested with DNAse I at room temperature for about 5 minutes. These reaction conditions were determined from a prior calibration study, in which the incubation time required to produce predominantly 100–300 basepair fragments was determined. The material was extracted with phenol/chloroform before ethanol precipitation.

The fragments in the digest mixture were blunt-ended and ligated with EcoRI linkers. The resultant fragments were analyzed by electrophoresis (5–10V/cm) on 1.2% agarose gel, using PhiX174/HaeIII and lambda/HindIII size markers. The 100–300 bp fraction was eluted onto NA45 strips (Schleicher and Schuell, Keene, N.H.), which were then placed into 1.5 ml microtubes with eluting solution (1 M NaCl, 50 mM arginine, pH 9.0), and incubated at 67° C. for 30–60 minutes. The eluted DNA was phenol/chloroform extracted and then precipitated with two volumes of ethanol. The pellet was resuspended in 20 ml TE (0.01 M Tris HCl, pH 7.5, 0.001 M EDTA).

B. CLONING IN AN EXPRESSION VECTOR.

Lambda gt11 phage vector (Huynh) was obtained from Promega Biotec (Madison, Wis.). This cloning vector has a unique EcoRI cloning site 53 base pairs upstream from the beta-galactosidase translation termination codon. The genomic fragments from above, provided either directly from coding sequences or after amplification of cDNA, were introduced into the EcoRI site by mixing 0.5–1.0 ug EcoRI-cleaved gt11, 0.3–3 ul of the above sized fragments, 0.5 ul 10× ligation buffer (above), 0.5 ul ligase (200 units), and distilled water to 5 ul. The mixture was incubated overnight at 14° C., followed by in vitro packaging, according to standard methods (Maniatis, 1982, pp. 256–268).

The packaged phage were used to infect E. coli strain KM392, obtained from Dr. Kevin Moore, DNAX (Palo Alto, Calif.). Alternatively, E. Coli strain Y1090, available from the American Type Culture Collection (ATCC #37197), can be used. The infected bacteria were plated and the resultant colonies were checked for loss of beta-galactosidase activity-(clear plaques) in the presence of X-gal using a standard X-gal substrate plaque assay method (Maniatis). About 50% of the phage plaques showed loss of beta-galactosidase enzyme activity (recombinants).

C. SCREENING FOR HEV RECOMBINANT PROTEINS.

HEV convalescent antiserum was obtained from patients infected during documented HEV outbreaks in Mexico, Borneo, Pakistan, Somalia, and Burma. The sera were immunoreactive with VLPs in stool specimens from each of several other patients with ETNANB hepatitis.

A lawn of E. coli KM392 cells infected with about $10^4$ pfu of the phage stock from above was prepared on a 150 mm plate and incubated, inverted, for 15–18 hours at 37° C. The lawn was overlaid with a nitrocellulose sheet, causing transfer of expressed HEV recombinant protein from the plaques to the paper. The plate and filter were indexed for matching corresponding plate and filter positions.

The filter was washed twice in TBST buffer (10 mM Tris, pH 8.0, 150 mM NaCl, 0.05% Tween 20), blocked with AIB (TBST buffer with 1% gelatin), washed again in TBST, and incubated overnight after addition of antiserum (diluted to 1:50 in AIB, 12–15 ml/plate). The sheet was washed twice in TBST and then contacted with enzyme-labeled anti-human antibody to attach the labeled antibody at filter sites containing prptides recognized by the antiserum. After a final washing, the filter was developed in a substrate medium containing 33 ml NBT (50 mg/ml stock solution maintained at 4° C.) mixed with 16 ml BCIP (50 mg/ml stock solution maintained at 4° C.) in 5 ml of alkaline phosphatase buffer (100 mM Tris, 9.5, 100 mM NaCl, 5 mM MgC12). Purple color appeared at points of peptide production, as recognized by the antiserum.

D. SCREENING PLATING.

The areas of peptide production determined in the previous step were replated at about 100–200 pfu on an 82 mm plate. The above steps, beginning with a 15–18 hour incubation, through NBT-BCIP development, were repeated in order to plaque purify phage secreting an antigen capable of reacting with the HEV antibody. The identified plaques were picked and eluted in phage buffer (Maniatis, p. 443).

Two subclones which were selected are the 406.3-2 and 406.4-2 clones whose sequences are set forth above. These sequences were isolated from an amplified cDNA library derived from a human Mexico HEV stool specimen. Using the techniques described in this section, polypeptides expressed by these clones have been tested for immunoreactivity against a number of different human HEV-positive sera obtained from sources around the world.

As shown in Table 4 below, 9 sera immunoreacted with the polypeptide expressed by the 406.4-2, and 8 sera immunoreacted with polypeptide expressed by the 406.3-2 clone.

For comparison, the Table also shows reactivity of the various human sera with the non structural peptide Y2. Only one of the sera reacted with the polypeptide expressed by this clone. No immunoreactivity was seen for normal expression products of the gt11 vector.

TABLE 4

Immunoreactivity of HEV Recombinant Proteins: Human Sera

| Sera | Source | Stage | 406.4-2(M) | 406.3-2(M) | 406.4-2(B) | 406.3-2(B) | Y2 | lgt 11 |
|---|---|---|---|---|---|---|---|---|
| FVH-21 | Burma | A | – | – | NT | NT | – | – |
| FVH-8 | Burma | A | + | – | NT | NT | + | – |
| B-IgG | Burma | C | + | + | + | + | NT | – |
| SOM-19 | Somalia | A | + | + | + | + | – | – |
| SOM-20 | Somalia | A | + | + | + | + | – | – |
| IM-35 | Borneo | A | + | + | NT | NT | – | – |
| IM-36 | Borneo | A | – | – | NT | NT | – | – |
| PAK-1 | Pakistan | A | + | + | NT | NT | – | – |
| FFI-4 | Mexico | A | + | + | + | + | – | – |
| FFI-125 | Mexico | A | + | + | + | + | – | – |
| F387-C | Mexico | C | + | + | + | + | NT | – |
| Normal | U.S. | | – | – | – | – | – | – |

Y2 represents an amino acid sequence encoded by a 157 basepair nucleic acid sequence from the first open reading frame of the HEV genome.
Acute-phase sera are collected between 1 and 12 days after the onset of HEV-related symptoms.
Convalescent-phase sera are collected between 30 and 90 days after the onset of jaundice.
+, reaction; –, no reaction; NT, not tested; A, acute; C, convalescent.

E. PRODUCING THE 406.3-2(M) ANTIGEN.

The 406.3-2 gt11 plasmid from above was digested with EcoRI and the released HEV fragment was amplified by PCR in the presence of linkers which added an NcoI site at the 5' fragment end, and a BamHI site at the 3' fragment end. The amplified material was digested with NcoI and BamHI and inserted into the NcoI/BamHI site of the glutathione S-transferase vector pGEX™ expression vector, according to the manufacturer's instructions.

The pGEX™ plasmid was used to transform E. coli host cells, and cells which are successfully transformed with the pGEX™ vector are identified by immunofluorescence, using anti-HEV human antisera.

F. PRODUCING THE 406.4-2 ANTIGEN.

The 406.4-2 gt11 plasmid from above was digested with EcoRI and the released HEV fragment was amplified by PCR, and the amplified fragment was inserted into the NcoI/BamHI site of the pGEX™ expression vector, as above. Peptide expression of the 406.4-2 peptide was similar to that described for the 406.3-2 fusion peptide.

G. PRODUCING THE SG3 ANTIGEN.

The SG3 peptide was prepared by first amplifying the SEQ ID NO:7 sequence with 5' EcoRI-NcoI and 3' BamHI primer-linkers, using a gt10 phage BET1 clone plasmid containing the entire ORF2 and ORF3 regions of HEV (B). The amplified fragment was inserted into the EcoRI/BamHI site of a pBluescript™ vector (Stratagene, La Jolla, Calif.), according to the manufacturer's instructions. After vector propagation and harvesting, the cloned insert was released by digestion with NcoI and BamHI, and gel purified. The purified fragment was inserted into the NcoI/BamHI site of a pGEXTM vector, and expressed in an E. coli expression system. Peptide expression of the SG3 peptide was similar to that described for the 406.3-2 fusion peptide.

H. PRODUCING THE CAPSID PROTEIN.

The capsid protein (B) was prepared substantially as described above by PCR amplification of the SEQ ID NO:1, from a pBET1 plasmid using a 5' primer containing an NcoI site and a 3' primer containing a BamHI site. The amplified fragment was inserted into the NcoI/BamHI site of a pGEX™ vector, and expressed in an E. coli expression system. The capsid protein (M) was similarly prepared.

I. PEPTIDE PURIFICATION.

HEV peptide antigens which were soluble, such as 406.4-2 and 406.3-2, were purified by polyacrylamide gel electrophoresis of bacterially expressed whole cell lysates. Crude lysate preparations were loaded on 7.5% SDS-PAGE gels and run until size markers corresponding to the predicted size of each protein have nearly run off each gel. The gel running buffer was replaced with fresh buffer and the gel allowed to continue to run for 5 minute intervals. The gel running buffer was collected after each interval and replaced with fresh buffer. The fractions were dialyzed and concentrated, and each fraction tested for immunoreactivity to a pGEX™ fusion partner, glutathione S-transferase, specific monoclonal antibody. Highly reactive fractions were pooled.

Alternatively, the peptides when expressed as GST fusions (pGEX™) were purified by column chromatography using Gluathione Sepharose, 4B (Pharmacia, Piscataway, N.J.). Briefly, non-GST fusion proteins were washed away from the column and bound protein was then eluted with 10mM glutathione in 50 mM Tris HCl pH 8.0.

Insoluble HEV peptides, such as SG3, were purified as follows. Cells induced to express the pGEX™ fusion protein were lysed with two passes through a french-press. The lysate was layered on a 40% solution of glycerol and spun at 3500 rpm in a J-20 rotor in a Beckman J221 centrifuge for 5 minutes. The pellet was resuspended in PBS then repelleted. The pellet was then resuspended in 6 M urea, 6 M guanadine in PBS pH 8.0 with homogenization for 5 minutes and repelleted. The suspension was filtered through a 0.22 um filter (Nalgene, Kent, U.K.) and loaded on an IMAC column (Pharmacia) containing Fast Flow Chelating Sepharose™ (Pharmacia) loaded with 3 column volumes of a $CoCl_2$ solution according to the manufacturer's instructions.

The bound protein was eluted with a 2 column gradient of 6 M urea, 6 M guanidine, and between 0–1 M imidazole in PBS with a pH range of 8.0 to 6.0. The column was stripped with 0.1 M EDTA in PBS and the fractions analyzed; e.g., by the ELISA protocol detailed in Examples 6, 8 or 10.

EXAMPLE 2

Human Primary Hepatocytes in Culture

A. ISOLATION OF HEPATOCYTES.

Hepatocytes were isolated from human liver obtained from Stanford University Medical Center. The liver was either perfused in situ or excised as a wedge for perfusion in laboratory. The initial perfusion was performed for 10 minutes at 60 ml/min using $Ca^{++}$-, $Mg^{++}$-free Hanks' balanced salt solution supplemented with 10 mM HEPES (pH7.4) and 0.5 mM [ethylene bis(oxyethylenenitrillo]-tetraacetic acid. Perfusion was continued for additional 20 minutes using Williams' medium E (WME) supplemented with 10 mM HEPES (pH7.4) and 100 U/ml collagenase (type I, Sigma Chemical Co., St. Louis, Mo.).

After perfusion the liver capsule was removed using fine forceps, and hepatocytes were dislodged by gentle shaking in collagenase solution. The hepatocyte suspension was filtered through several layers of gauze and mixed with an equal volume of WMW containing 10% fetal bovine serum (FBS). Hepatocytes were sedimented by centrifugation at 50×g for 5 minutes and resuspended in WME containing 5% FBS. Hepatocytes were sedimented and resuspended in the manner for 2 additional times. The final cell preparation was further filtered through several layers of gauze before examining for viability using trypan blue. The cells were plated at a density of $2\times10^6$ cells per 60-mm Primaria plates (Falcon/Becton Dickinson, Franklin Lakes, N.J.) pre-coated with collagen (Collaborative Research, Bedford, Mass.).

Cultures were incubated at 37° C. in 5% $CO_2$ for 3 hours to allow attachment and the medium was changed to a serum-free formulation and every 48 hrs thereafter. The serum-free formulation was a WME-based medium supplemented with growth factors, hormones, 10 mM HEPES (pH7.4), 100 ug/ml gentamicin, as has been described (Lanford, 1989).

B. DETECTION OF LIVER-SPECIFIC PROTEINS.

Human hepatocyte cultures were maintained in serum-free medium for various periods of time and labeled with [$^{35}$S]-methionine for 24 hrs. The medium was adjusted to contain 1 mM PMSF, 1 mM EDTA, and 1% NP40. Antibodies specific for the different plasma proteins were bound to protein A-agarose beads, the beads were washed with PBS, and aliquots of the labeled medium were incubated for 16 hrs at 4° C. with the antibody-bead complexes. The beads were washed 3 times with a buffer containing 1% NP40, and immunoprecipitated proteins were eluted with gel electrophoresis sample buffer containing 2% SDS and 2% 2-mercaptoethanol. Samples were analyzed by gradient SDS-PAGE (4 to 15%) and autoradiography.

EXAMPLE 3

In Vitro HEV Infection of Primary Human Hepatocytes

A. HEV INFECTION OF HUMAN HEPATOCYTES.

The HEV-infected cynomolgus monkey #73 stool pool (fourth passage) was used as an inoculum for infections of primary human hepatocytes. Various amounts of inoculum was diluted in 1 ml of serum-free medium (SFM) and applied to the culture during a 3 hr incubation period. This solution was then supplemented with 2 ml of fresh SFM and the entire mixture was incubated overnight. The next day, cell monolayers were washed with WME (10 mM HEPES, pH7.4) for three times and changed to fresh SFM, which was changed at two day intervals thereafter.

B. IMMUNOFLUORESCENCE STAINING ASSAY.

Primary cynomolgus monkey hepatocytes were isolated and plated in tissue culture plates with collagen-coated coverslips as described. Cells on coverslips were infected with either the HEV-infected cynomolgus monkey #73 stool pool or an NIH normal human serum three days after initial plating. The infections were allowed to proceed for 2 weeks.

Cells on coverslips were fixed in 90% acetone at room temperature for 1 minute. The coverslips were then air-dried. The coverslips were blocked in 1% goat serum in PBS for 1 hour, washed with PBS three times, and incubated with a mixture of rabbit antisera against HEV recombinant proteins 406.3-2(B), 406.4-2(M), and 406.4-2(B) at room temperature for 3 hours. The coverslips were again washed with PBS 3 times and reacted with fluorescein isothiocyanate-conjugated (FITC) goat anti-rabbit IgG(H+L) (Zymed) diluted in PBS-1% goat serum for 30 minutes. After the coverslips were washed with PBS for 3 times and air-dried, they were mounted with FITC glycerol solution and examined under a fluorescent microscope.

C. REVERSE TRANSCRIPTION/POLYMERASE CHAIN REACTION (RT/PCR).

HEV infection of primary cynomolgus macaque hepatocytes was evaluated by RT/PCR assays. The primers for cDNA synthesis and PCR were based on the nucleotide sequences of the full-length HEV cDNA (Tam, et al., 1991a, 1991b). Primers HEV3.2SF1 (nt 6578–6597) and HEV3.2SF2 (nt 6650–6668) are of sense polarity from the ORF2 region of the viral genome and HEV3.2SR1 (nt 7108–7127) and HEV3.2SR2 (nt 7078–7097) are antisense primers within the region. Following extraction of total cellular RNA from HEV-infected cells using one-step guanidinium procedure or HEV-infected supernatants according to the method of Chomczynski, et al. (Chomzynski, 1987), aliquots of RNA samples were heat-denatured at 95° C. for 5 minutes and subjected to reverse transcription at room temperature for 5 minutes and 42° C. for 60 minutes using 200 units per reaction of MMLV-reverse transcriptase (BRL) in a 20 ul reaction volume containing 20 units of RNasin (Promega), 1×PCR buffer (Perkin-Elmer Cetus, Norwalk, Conn.), with a concentration of 1 mM each deoxyribonucleotide (Perkin-Elmer Cetus), and 2.5 uM of HEV3.2SR1 primer. The reaction mixture was then heat-treated at 95° C. for 5 minutes to denature the MMLV-reverse transcriptase.

Ten microliters of the cDNA synthesis product was used for PCR in a final volume of 50 ul with 0.5 uM HEV3.2SF1 primer, 1.25 units Taq DNA polymerase (AmpliTaq, Perkin-Elmer Cetus), and 1×PCR buffer, overlayed with 50 ul of mineral oil, and subjected to 40 cycles of PCR in a Perkin-Elmer thermocycler (95° C.×1 minute; 52° C.×2 minutes; 72° C.×30 seconds). Ten microliters of the first-round PCR product then underwent another 40 cycles of nested PCR (95° C.×1 minute; 55° C.×2 minutes; 72° C.×30 seconds) in a total volume of 50 ul containing the internal PCR primers HEV3.2SF2 and HEV3.2SR2.

First- and second-round PCR products were subjected to agarose electrophoresis, ethidium bromide stained and photographed under UV light. Southern transfer was performed and filters were hybridized with [$^{32}$P-dCTP]-labeled internal probe HEVORF2–7 exclusive of the primers (nt 6782–6997), and autoradiography performed.

EXAMPLE 4

Preparation of a 62 kDa HEV Antigen

The 62K antigens were produced by a baculovirus expression system in insect cells as follows.

A. CONSTRUCTION OF RECOMBINANT BACULOVIRUSES.

Recombinant baculovirus ORF-2-rAcNPV expressing the entire ORF-2 of Burma strain of hepatitis E virus was constructed as described previously, He, J., et al., J. Clin. Microbiology, 31:2167 (1993), herein incorporated by reference.

Construction of recombinant baculovirus pBBIII-62K expressing the C-terminal 549 amino acids of ORF2 is described as follows below and summarized in FIG. 5. In brief, a 204 base-pair (bp) DNA fragment containing nucleotides 5480 to 5684 of ORF-2 from the Burma strain of HEV (FIG. 2) was synthesized using polymerase chain reaction (PCR) and a HEV cDNA plasmid template pBBIII-ORF2, together with two primers (5' primer, SEQ ID NO:29 and 3' primer, SEQ ID NO:30). The 5' primer contained a BamHI site and the 3' primer has a HindIII site to facilitate plasmid construction. The PCR product was digested with BamHI/HindIII and ligated to a baculovirus expression vector pBluBacIII (Invitrogen, San Diego) which has been previously digested with the same restriction endonucleases to form plasmid pYZ1 (FIG. 1).

A 1.5 kilobase-pair (kbp) HindIII DNA fragment, corresponding to 3' portion of HEV ORF-2, is excised from a previously constructed plasmid pBBIII-OF2 and inserted into the plasmid pYZ1 at the HindIII site to form the final baculovirus transfer vector pBBIII-62K, which is subsequently used in recombinant virus construction. The nucleotide sequence derived from PCR is confirmed by DNA sequencing and the correct orientation of the HindIII/HindIII insert in pBBIII-62K is verified by restriction digestion analysis. Transfection, plaque purification, and virus amplification of recombinant baculovirus BBIII-62K is carried out according to protocols described (Invitrogen, San Diego).

B. CELL CULTURE AND EXPRESSION CONDITIONS.

*Spodoptera frugiperda* (Sf9) Cells in suspension culture flasks were maintained at 27° C. in Grace's insect medium supplemented with 5% fetal bovine serum (v/v), 50 ug/mL gentamycin, and 0.1% Pluronic F-68. All culture ingredients were obtained from Gibco/BRL (Gaithersburg, Md.) and cells were cultured according to protocols described by the manufacturer (Invitrogen, La Jolla, Calif.). Viable cells with a density of $2 \times 10^6$/mL were pelleted by centrifugation. The cell pellet was resuspended in 1/10 of the original volume of medium containing the recombinant virus, BBIII-62K, at a multiplicity of infection of 2 plaque forming units (PFU) per cell. Infection was carried out for one hour without stirring. The infected cells were diluted to the original density with fresh medium and maintained at 27° C. for 2–7 days with agitation (75–95 rpm).

Procedures for infection of monolayer cells are described in protocols supplied by Invitrogen, Inc.

EXAMPLE 5

SDS PAGE and Immunoblot of ORF2 Produced in Sf-9 Suspension Culture and Monolayer Cells Infected cell lysates from Example 5, above, prepared after various times post infection were separated by centrifugation to generate both phosphate-buffered saline (PBS)-soluble and insoluble fractions. Proteins from both fractions were electrophoresed on SDS-polyacrylamide gels, which were either stained with Coomassie-blue solution (FIG. 6a) or transferred to nitrocellulose paper followed by a Western blot analysis (FIG. 6b), as follows.

A. ANTI-HEV ANTISERUM.

Two rabbit polyclonal antisera, anti-SG3 and anti-1L6, were generated to the 3' portion of ORF-2, 327 and 42 amino acids in length sharing the same C-terminus of ORF-2 from the Burma strain of HEV as described previously (Yarbough 1991, 1994), herein incorporated by reference.

B. SDS-PAGE AND IMMUNOBLOT.

To prepare protein samples for SDS-PAGE, approximately $2 \times 10^6$ baculovirus-infected Sf9 cells were pelleted in mircrocentrifuge and resuspended in 150 ul of phosphate-buffered saline. Cells are lysed by sonication. The lysate was subjected to centrifugation in a microcentrifuge at 4° C. for 15 min. The supernatant and pellet were separated and denatured in protein denaturation buffer containing 20 mM Tris (pH 6.8), 10% 2-mercaptoethanol, 2% SDS, 30% (vol/vol) glycerol, and 0.1 mg/ml bromophenol blue. Protein samples were electrophoresed on 4–20% polyacrylamide-SDS gels which were then transferred to a PVDF membrane. Immunoblot was carried out using rabbit polyclonal antisera described above and a chemiluminescence detection assay (ECL kit of Amersham).

EXAMPLE 6

Purification of 73K, c62K and r62K ORF2 Products

A. PURIFICATION OF FULL-LENGTH ORF2 (73K).

Recombinant baculovirus ORF2-rAcNPV infected cell pellets were resuspended in phosphate buffered saline (PBS) containing 1 mM EDTA, 1 ug/mL aprotinin, 10 ug/mL leupeptin, 0.5 mg/mL Pefabloc SC, and 10 ug/mL pepstatin at a cell density of 20% (w/v). The suspension was lysed by three passages through a Microfluidics microfluidizer M-110S at a liquid pressure of 14,000 PSI followed by centrifugation of the lysate at $10,000 \times g$ for 30 minutes at 5° C.

The supernatant was decanted and the insoluble pellet resuspended in 25 mM BICINE at pH 8.5. The suspension was re-centrifuged under the same conditions and the washed pellet extracted in 25 mM BICINE containing 0.5% SDS (w/v) for 30 minutes at ambient temperature. The extracted material was centrifuged for 30 minutes at $10,000 \times g$ at ambient temperature with the resultant supernatant separated and diluted 1:5 in 25 mM BICINE pH 8.5 in 8M urea.

This material was chromatographed on a Hyper-D-S (BioSepra, Framingham, Mass.) strong cation exchange column in the same buffer at a superficial linear velocity of 3000 cm/hr. Following loading and washing of the column, the 73K protein was eluted in a linear gradient of 0 to 400 mM NaCl in the same buffer.

The 73K protein containing fractions from the Hyper-D-S column were dialyzed against a 500 volume excess of water overnight followed by centrifugation of the dialyzate at $10,000 \times g$ at 4° C. The supernatant was discarded and the pellet extracted with 0.5% SDS in 25 mM Tris pH 8.5. Solid Cleland's Reagent (DTT) was added to a concentration of 50 mM and the solution heated to 100° C. for three minutes followed by immediate dilution into a 100 fold volumetric excess solution containing 50 mM glycine pH 10.5, 10% glycerol, 5 mM glutathione (reduced), 0.5 mM glutathione (oxidized), and 1 g/L PEG 3500. The solution was allowed to air oxidize overnight. Following oxidation, the solution was concentrated and diafiltered by tangential cross flow filtration to 25 mM Tris pH 8.5. The material was further concentrated by centrifical ultrafiltration.

B. PREPARATION OF CELL LYSATE AND PURIFICATION OF RECOMBINANT 62K ANTIGEN.

Frozen Sf9 cells infected with recombinant baculovirus BBIII-62K were resuspended in phosphate buffered saline (PBS) containing 1 ug/mL aprotinin, 1 mM EDTA, 10 ug/mL leupeptin (Boehringer Mannheim, Indianapolis, Ind.), 0.5 mg/mL Pefabloc SC (Boehringer Mannheim), 10 ug/mL pestatin (Boehringer Mannheim) at a concentration of 20% (w/v). The cellular suspension was lysed in a Microfluidics microfluidizer M110S (Newton, Mass.) by two passages at 14,000 PSI. Lysed cells were centrifuged (15,000×g, 4° C., 30 minutes). The cellular supernatant was then pre-treated by addition of solid dithiothreitol (DTT) (Cleland, 1964) to a concentration of 50 mM and dialyzed initially against 100 volumes of 10 mM Tris pH 8.5, 50 mM NaCl, and 0.5 mM DTT for 8 hours at 4° C.

Dialysis was continued for another 8 hours against fresh buffer minus DTT. Using this two step dialysis procedure aggregation of the 62-kDa protein with contaminating cellular proteins was virtually eliminated. The r62-kDa protein was found to be completely soluble in the lysis buffer with quantitative recovery of the molecule in the cell lysis supernatant.

The dialysate was prefiltered through a Millipore 0.22 micron filter and then loaded directly onto a DEAE EMD 650(S) column (E. Merck) equilibrated in 10 mM Tris pH 8.6 50 mM NaCl. The r62-kDa protein was eluted in a linear gradient of 50–500 mM NaCl over 15 column volumes at a superficial linear velocity of 100 cm/hr. The 62-kDa protein eluted early in the gradient.

The presence of ORF-2 related 62-kDa was confirmed by Western blotting of column fractions with rabbit polyclonal antibody, 1L6 (Yarbough, et al., 1991), an antibody raised against the carboxyl terminal region of the parent ORF-2 protein.

The r62K containing fractions from the DEAE column were pooled, concentrated by centrifugal ultrafiltration (Amicon, Beverly, Mass.). The r62-kDa protein was further purified and buffer exchanged on a 60 cm Sephacryl S-100 column (Pharmacia, Piscataway, N.J.) equilibrated in 25 mM Tris, pH 7.2, (5×100 cm) at a superficial linear velocity of 30 cm/hr. Fractions containing 62-kDa were pooled and concentrated by centrifugal ultrafiltration. This step in the procedure was utilized primarily as a buffer exchange step.

The 62-kDa containing pool from the S-100 column was applied to the strong anion exchange column Poros Q/F column (4.6×10 mm) (Perseptive Biosystems, Cambridge Mass.) equilibrated with buffer B (25 mM Tris, pH 7.2) at a superficial linear velocity of 3000 cm/hr. The column was washed with 5 column volumes of buffer B. The 62-kDa was eluted with a linear gradient of 0 to 1 M NaCl (total 10 column volumes) in buffer B. The 62-kDa protein eluted at approximately 300 mM NaCl. If necessary, the r62-kDa was buffer exchanged by tangential cross flow diafiltration using a spiral wound cartridge (Millipore Prep TFF; Millipore, Bedford, Mass.). At this stage, the 62-kDa protein was nearly homogeneous based upon SDS-PAGE and Western blotting.

In the purification steps described above, buffer conductivities and pH's were monitored with a Radiometer Copenhagen CDM 83 conductivity meter (Westlake, Ohio) and a PHM reference standard pH meter, respectively. All buffer constituents were either biotechnology or USP grade and determined to be essentially pyrogen free by limulus amebocyte lysate assay.

Further, for the quantitation of recovery of 62K antigen from insect cell lysates the following double antibody sandwich (ELISA) technique was utilized. Anti-1L6 antibody, a polyclonal rabbit antibody directed against the carboxyl terminal portion of the ORF-2 protein, was purified by Protein G Sepharose affinity chromatography and coated onto microtiter plates at a concentration of 1.6 ug/mL per well in carbonate/bicarbonate buffer. After washing and blocking, purified 62-kDa antigen (quantitated by amino acid analysis) or process samples were added to the plate and diluted in series of two fold dilutions. After incubation of the antigen and washing, a second antibody, anti-SG3 conjugated to biotin was added to the plate and incubated. The SG3 antigen corresponds to the carboxyl terminal 328 amino acids of the 62-kDa protein (Yarbough, et al., 1994). This incubation was followed by a final incubation with streptavidin conjugated horse radish peroxidase. After final washing, substrate was added and the plates were read at an absorbance of 490 nm.

Protein concentrations of samples were established using the Bradford assay (Pierce, Rockford, Ill.).

EXAMPLE 7

Electron Microscopy

Protein samples were applied to Formvar-coated carbon grids and stained with 2% uranyl acetate or 2% phosphotungstic acid, pH 6.5, before they were viewed on a electron microscope. When fixation was required, protein samples were fixed in PBS containing 2% glutaraldehyde for 30 min. Buffer exchange was then carried out by centrifugation in Centricon-30 (Amicon, Beverly Mass.) to change the sample buffer to PBS.

EXAMPLE 8

ELISA Assays

ELISA was used to compare the antigenicity of HEV protein products expressed in E. coli and baculovirus. Small scale paneling of coded sera was used to define the sensitivity and specificity of a diagnostic incorporating baculovirus expressed proteins.

A. Human Sera.

Human sera were from stored panels previously collected during various epidemics of hepatitis E at various geographical locations. Sera from non-human primates were from cynos and chimps experimentally infected with the hepatitis E virus at the Center for Disease Control, Atlanta, Ga.

B. ELISA.

The proteins used for immunodiagnosis include: (1) SG3 encoding 327 amino acids of ORF2 expressed as a fusion protein in *E. coli* (SEQ ID NO:17), (2) 73K encoding 660 amino acids of ORF2 expressed in baculovirus, and (3) 62K encoding 549 amino acids of ORF2 expressed in baculovirus. Antigens were coated individually onto the wells of polystyrene microtiter plates (Yarbough, et al., 1994). Each well was incubated overnight at 4° C. with 200 ng of each protein in 100 ul 0.05 M sodium carbonate pH 9.5 (1.59 g $Na_2CO_3$, 2.93 g $NaHCO_3$, 0.02% sodium azide, pH 9.5, bring to 1000 ul) buffer. After washing in PBS-0.05% polyaxyethylene (20) monolaurate "Tween 20™" (Sigma) and blocking with 200 ul of 1% bovine serum albumin (BSA) in PBS for 1.5 hours at room temperature, serum samples were diluted 1:100 in antibody diluent (1000 ml Tris buffered saline (40 mM Tris pH 7.5, 1 M NaCl), 30 ml goat serum, 10 g bovine serum albumin, fraction V, 10 g non fat milk (Carnation), 1 g gelatin (EIA) grade, and 0.2 g thimersol (preservative), see Antibody Diluent Production, following) and incubated for 30 minutes at 37° C. After removal of the primary antibody and washing to remove any unbound 1st antibody, the wells were incubated for 30 minutes at 37° C. with secondary antibody, HRP conjugated goat anti-human IgG (gamma chain specific) or goat anti-human IgM (mu chain specific).

After final washing, substrate was added and the plates were read at an absorbance of 490 nm. Sera producing an O.D. value of 0.300 or greater were scored positive for HEV antibodies. This concurs with a P/N ration of greater than 3.0 and a minimum of 5 standard deviations above the mean of the normal sera.

C. ANTIBODY DILUENT PRODUCTION.

Antibody Diluent was made as follows: 200 ml of TBS was heated to 60° C. and 1 g gelatin melted therein. The volume was brought to 1000 ml with TBS. 10 g BSA was added when the temperature had cooled to 40° C. The mixture was stirred at room temperature until the BSA was in solution. 30 ul of goat serum was then added follwed by the addition of thimerosol to 0.02%. The reagent could be stored for two weeks at 4° C. Prior to use, milk was stirred in to 1% at room temperature for 30 minutes.

EXAMPLE 9

Further Characterization of the 62K Antigen

A. CHARACTERIZATION OF RECOMBINANT 62-kDA PROTEIN BY SDS-POLYACRYLAMIDE GEL ELECTROPHORESIS AND WESTERN BLOTTING.

Processed fractions of the 62-kDa protein (Examples 4 and 6B) were denatured and analyzed by SDS-polyacrylamide gel electrophoresis. Briefly, sodium dodecyl sulfate polyacrylamide gel electrophoresis was performed according to the tricine SDS-PAGE procedure (Schagger and von Jagow, 1987). Western blotting was performed as previously described (Yarbough, et al., 1994). A rabbit polyclonal antibody directed to the carboxyl-terminal regions of ORF-2, 1L6, was used to evaluate purified protein (Example 5). The tricine buffer system was used in order to obtain higher resolution and minimize interference with Edman reagents in solid phase sequencing from PVDF (polyvinylidene difluoride) membranes.

Figure 14A:
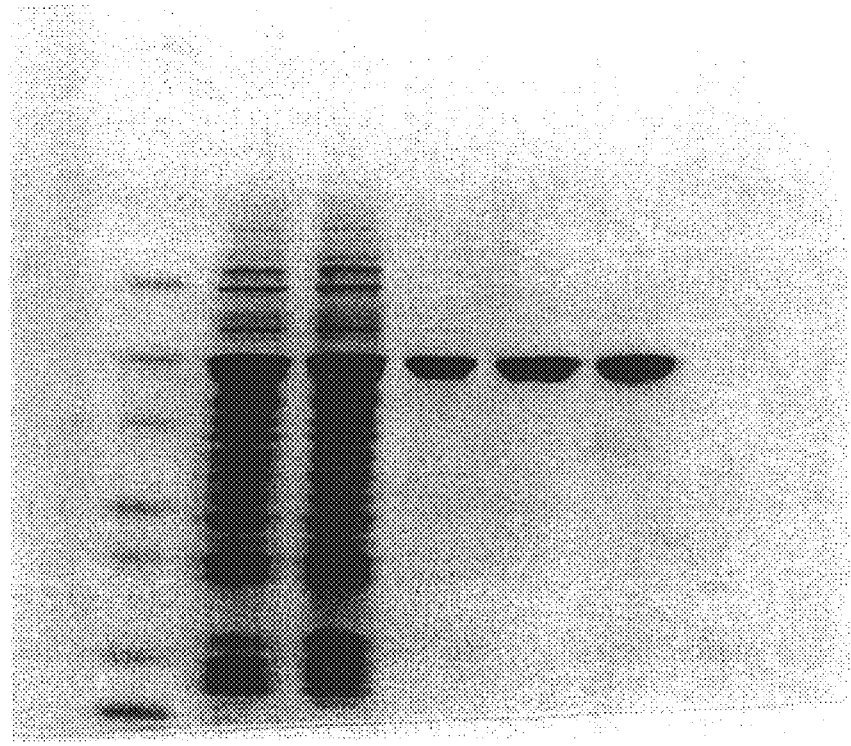
FIGS. 14A and 14B present the results of an analysis of the r62-K purification process using 4–20% SDS-polyacrylamide gel electrophoresis (14A) and a corresponding western blot (14B).
Figure 14B:
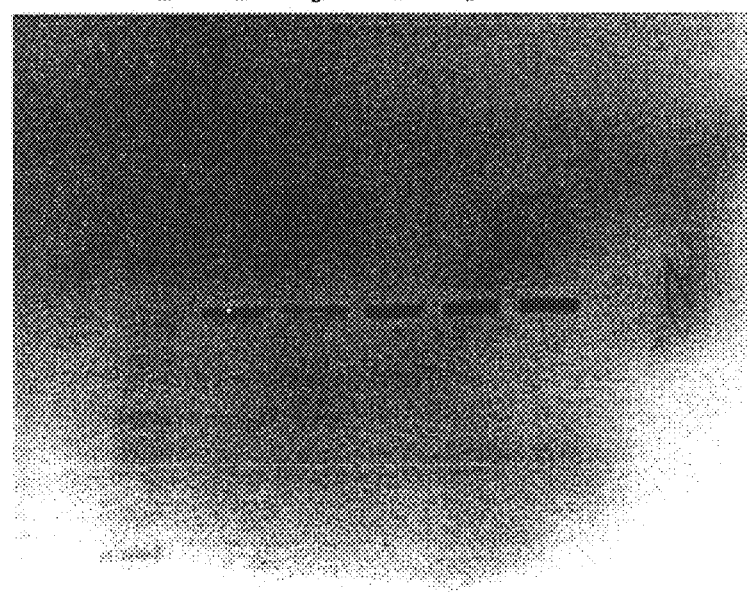

The results of an analysis of the r62-K purification process using 4–20% SDS-polyacrylamide gel electrophoresis and corresponding western blot are presented in FIGS. 14A and 14B. In FIG. 14A: lane 1, Molecular weight markers; lane 2, cell lysate; lane 3, cell lysate supernatant; lane 4 DEAE peak pool; lane 5, Sephacryl s-100 peak pool; lane 6, Poros HQ/F peak pool. Molecular mass markers are Novex SeeBlue Pre-Stained Standards (San Diego, Calif.) and range as follows (from top to bottom): Myosin, 250-kDa; BSA, 98-kDa; Glutamic dehydrogenase, 64-kDa; Alcohol dehydrogenase, 50-kDa; Carbonic anhydrase, 36-kDa; Myoglobin, 30-kDa; Lysozyme, 16-kDa; Aprotinin, 6-kDa; Insulin B chain, 4-kDa. FIG. 14B presents a Western blot of lanes 1–6 from above. Samples were diluted 15 fold prior to SDS-PAGE and transfer. 1L6 antibody was used as the initial antibody.

Analysis of the initial cell lysate (FIG. 14A, lane 2) indicated that the 62-kDa protein was adequately expressed in the baculovirus expression system and suitable for further processing. The cell lysis supernatant (FIG. 14A, lane 3) appeared to yield essentially quantitative recovery of the 62-kDa protein as a soluble product. The DEAE pool (FIG. 14A, lane 4) yielded a significant purification of the 62-kDa from the previous lysate supernatant pool with the Sephacryl S-100 and Poros HQ/F chromatography steps resulting in further purification of the 62-kDa protein (FIG. 14A, lanes 5 and 6).

One curious aspect of the gel electrophoresis profiles was the apparent purification of the 62-kDa band as a doublet. The Western blot illustrated in FIG. 14B contains a 15 fold dilution of the samples run on SDS-PAGE in parallel. In the Western blot, the protein was visualized as a doublet with the lower band appearing to accumulate over the course of purification. However, proteolysis appeared to be minimal. This result suggested that the protein may exists as a heterogenous species through potential side chain modifications such as glycosylation, N-terminal, or C-terminal modification. The following experiments were carried out to determine the source of the heterogeneity.

B. AMINO TERMINAL SEQUENCE AND AMINO ACID COMPOSITION.

The 62-kDa protein was resolved by SDS-polyacrylamide gels and transferred to PVDF (Biorad, Richmond, Calif.) membranes. The amino acid composition and amino-terminal sequences were determined for the protein.

Amino acid composition analysis was carried out on a Beckman Model 6300 (Fullerton, Calif.) ion-exchange instrument following a 16 hour hydrolysis at 115° C. in 100 ul of 6N HCl, 0.02% phenol plus 2 nmol norleucine. Following hydrolysis, the samples were dried on a Speedvac and the resulting amino acids dissolved in 100 ul of sample buffer (Beckman, Fullerton, Calif.) containing 2 nmol homoserine with the homoserine acting as a second internal standard to independently monitor transfer of the sample onto the analyzer (Rosenfeld, et al., 1992). The instrument was calibrated with a 2 nmol mixture of amino acids and was operated according to the manufacturers specifications. Amino acid composition analysis was used to accurately quantitate protein concentrations in samples.

Amino-terminal sequencing was carried out on either an Applied Biosystem 470A or 477 (Foster City, Calif.) that was equipped with on-line HPLC's for the identification of the resulting phenylthiohydantoin (Pth) amino acid derivatives. Prior to sample application 25 pmol of a 16 residue internal sequencing standard peptide with the formula: [norleucine-(succinyl-lysine)$_4$]$_3$-norleucine was first spotted onto the sequencing filter (Elliott, et al., 1993). The 470A and 477 instruments were operated based upon manufacturer's recommendations and 3 pmol Pth standards were routinely used. All sequences were searched via the BLAST Network Service operated by the National Center for Biotechnology Information.

The levels of amino acids present in the first five cycles were approximately 10-fold lower than expected suggesting that a major portion of the 62-kDa molecule was blocked at the N-terminus. The sequence obtained appeared to be identical to the processed form of the 62-kDa originally produced in Sf9 cells expressing the full length ORF-2. Presumably a methionine aminopeptidase present in baculovirus infected Sf9 cells cleaved the N-terminal methionine introduced into the coding sequence of the recombinant protein to ensure correct initiation of translation.

C. TRYPTIC PEPTIDE ANALYSIS.

One hundred and two pmoles of the 62-kDa protein were digested in situ with trypsin in an excised polyacrylamide gel slice. A blank gel slice and a gel slice containing 50 pmoles of transferrin were also digested and analyzed in parallel as controls. The resulting peptides were resolved by reverse phase HPLC.

In gel enzymatic digestion was carried out according to Williams and Stone (Williams and Stone, 1995), using perfusion in an approximately 1:5 (enzyme weight:substrate weight) ratio of modified trypsin (Promega, Madison, Wis.) and digestion for 24 hours at 37° C. The resulting peptides were reduced/carboxylmethylated, extracted with 0.1% TFA, 60% $CH_3CN$ and then subjected to hydrolysis/amino acid analysis so that the amount and density (ug protein/$mm^3$) could be determined, with both of the parameters serving as valuable criteria to judge the probability of success of the impending digest. Amino acid composition analysis was carried out as described above.

Reverse phase HPLC was carried out on a Hewlett Packard 1090 HPLC system (Palo Alto, Calif.) equipped with an ISCO Model 2150 Peak Separator and a 25 cm Vydac C-18 (5 micron, 300 Angstrom) column (Hesperin, Calif.) equilibrated with 98% buffer A (0.06% Trifluoroacetic acid; TFA) and 2% buffer B (0.052% TFA, 80% acetonitrile) as described in Williams and Stone (1995). Peptides were then eluted with the following gradient program: 0–60 min (2–37% buffer B), 60–90 min (37–75% buffer B) and 90–105 min (75–98% buffer B) and were detected by their absorbance at 210 nm. Aliquots of digests in the 25–250 pmol range were fractionated on 2.1 mm internal diameter (ID) column eluted at 0.15 ml/min. Fractions were collected in capless Eppendorf tubes.

Out of a possible total of 38 tryptic peptides and 143 potential peaks detected by reverse phase HPLC analysis of the digested 62-kDa protein, 8 peaks were selected for laser desorption mass spectroscopy since the HPLC profile suggested that these peaks appeared to contain only one major species.

D. LASER DESORPTION MASS SPECTROSCOPY (LDMS).

Peaks 45, 50, 62, 65, 73, 82, 101, and 116 were further evaluated by LDMS. LDMS was used to resolve several issues:
(i) whether the peak was an artifact peak or was in fact a peptide? The analysis confirmed that none of the peaks were artifactual;
(ii) whether the peak contained more than one peptide? The analysis demonstrated that, in a few cases the peaks represented mixtures of peptides; and
(iii) whether the LDMS calculated mass was comparable to the predicted mass which was derived from the predicted amino acid sequence encoded by the viral RNA? In all cases the mass of the peptide was equivalent to the predicted mass, with the exception of peak 65 which appeared to be blocked.

Also, this analysis allows the ready determination of any post translational modifications.

To perform LDMS, 3 ul aliquots of peptides isolated via reverse phase HPLC were added on top of 1 ul of an alpha cyano-4-hydroxy cinnamic acid (alpha CHCA) matrix solution that was spotted onto a new target. Mixing of the matrix was accomplished by repeatedly pulling the sample into and expelling it from a micropipette. The samples were then allowed to air dry at room temperature. To avoid cross contamination, all targets were used only once. The alpha CHCA matrix solution was prepared at a concentration of 10–20 mg/mL in 40% $CH_3CN$/0.1% TFA (trifluoroacetic acid) and was used after vortexing and standing for a few minutes. Matrix solutions were stored for a maximum of 2 days at −20° C. The calibrants used for external calibration of peptides were gramicidin S (m/z=1142.5) and insulin (m/z=5734.5). Both calibrants were stored at −20° C. as 10 pmol/ul stocks in either 50% $CH_3CN$, 0.1% TFA, or 0.1% TFA. LDMS was carried out on a VG/Fisons TofSpec mass spectrometer (VG Organics, Manchester, U.K.) that was operated in the +ve linear ion mode at an accelerating voltage of 25 kV and was equipped with a nitrogen laser (337 nm) and a 0.65 m linear flight tube.

Routinely, 30 shots were averaged for each spectrum with 3–6 spectra acquired for each sample. The predicted masses were based upon the average isotypic, singly protonated mass and the expected mass accuracy was about ±0.25%.

Post-source decay sequencing was done in the reflectron mode with the ladder sequencing calibrated to a 2 pmole sequence of adrenocorticotropic hormone fragment ACTH clip fragment 18–39.

Peaks 65, 73, 101, and 116 appeared to be suitable for direct sequencing as the LDMS results indicated the presence of only one major species. Peaks 45, 50, 62, and 82 were also sequenced. Although the peaks appeared to be mixtures that would optimally require HPLC repurification prior to individual sequencing, it was decided to directly sequence these mixtures in view of the known mass information and predicted amino acid sequence.

E. SEQUENCE ANALYSIS OF LDMS PEPTIDES.

Peptide 65 did not yield an interpretable sequence. Upon further examination, the mass observed by LDMS was consistent with the N-terminal residues of the 62-kDa protein with addition of an N-terminal acetyl group (predicted 1786.9 Daltons versus 1785.5 Daltons observed; corresponding to a 0.03% error). Evaluation of a tryptic peptide data base using the predicted sequence of the 62-kDa protein revealed only one other peptide that was similar in molecular weight (residues 408–423). Post source decay analysis revealed that Peak 65 was indeed the predicted amino terminal tryptic peptide.

Sequence analysis of the peptides corresponding to peaks Peaks 45, 50, 62, 73, 82, 101, and 116 confirmed that the internal sequence of the predicted 62K protein was intact. Briefly, Peak 73 matched residues 327–355 of the known sequence. Peak 101 matched residues 123–139 of the known sequence. Peak 116 matched residues 424–431 of the known sequence. Peak 45 matched residues 412–423 of the ORF-2 sequence with a predicted mass of 1396.49 Daltons. Peak 50 matched residues 334–348 of the ORF-2 sequence. Peak 62 contained a short 6 peptide residue with a predicted mass of 749.84 Daltons which matched residues 513–518 of the ORF-2 sequence. Peak 82 was a mixture of three peptides that were matched to residues 424–437 (primary sequence), residues 438–466 (secondary sequence), and residues 555–578 (tertiary sequence). Taken together these results indicate that the internal sequences of the predicted 62K polypeptide appeared to be intact and colinear with the predicted sequence.

F. LC-MS AND CARBOXYL TERMINAL SEQUENCE ANALYSIS.

In order to evaluate the nature of the 62-kDa protein doublet observed by SDS-PAGE, the purified 62-kDa protein was chromatographed on a Vydac C18 reverse phase capillary column (Hesperin, Calif.) with the eluting peak being evaluated by electrospray mass spectrometry (ES-MS). Purified 62-kDa protein was chromatographed on a fused capillary Vydac C18 reverse phase column using ABI Model 410 syringe pumps at a flow rate of 50 ml per minute. The protein was chromatographed in a solvent system of 0.1% TFA in water (v/v) to 0.1% TFA in acetonitrile. An in line flow splitter was used to divert peaks at a flow rate of 10 ml per minute to a VG BioQ triple quadrupole mass spectrometer (VG Organics, Manchester, U.K.) operating in the positive ion electrospray ionization mode. The 62-kDa protein resolved into two primary peaks by ES-MS corresponding to 56.1 and 58.6-kDa.

The predicted molecular mass of the 62-kDa protein using the coding sequence of residue 112 to residue 660 of the ORF-2 region is 59.1-kDa. These data suggested that a deletion occurred in the molecule and that the deletion was most likely at the amino or carboxyl terminus. The protein was not found to be glycosylated both by periodate oxidation and GC-MS analysis.

Molecular mass determination by ES-MS is typically 0.01% (Scoble, et al., 1993). With the confirmation of the amino terminus, the ES-MS data suggests that the carboxyl terminus may be clipped between residues 551–552 and residues 536–537. Automated carboxyl terminal sequencing was performed using intact 62-kDa to confirm the putative carboxyl terminal processing.

For automated C-terminal sequence analysis, protein samples were applied to Zitex membranes (Norton Performance Plastics, Wayne N.J.) pre-treated with isopropanol and inserted into inert Kel-F columns (Norton Performance Plastics, Wayne N.J.). The sequencer column was installed into a Hewlett Packard G1009A sequencer (Palo Alto, Calif.) for chemical coupling and cyclization. The coupled peptidylthiohydantoin and cyclyzed product was cleaved to the C-terminal thiohydantoin-amino acid residue and the shortened peptide using an alkali salt of trimethylsilanolate (KOTMS). The derivatized sample was analyzed by an Hewlett Packard 1090 liquid chromatograph (Palo Alto, Calif.) with filter photometric detection at 269 nm using a Hewlett Packard specialty (2.1 mm×25 cm) reversed phase PTH analytical HPLC column.

A 39 minute binary gradient (Solvent A: phosphate buffers pH 2.9; Solvent B: acetonitrile) utilizing alkyl sulfonate as an ion pairing agent was developed. Thiohydantoin-amino acid standards at 100 pmole were used to standardize the analysis. The initial sequencing cycle gave rise to two very strong peaks corresponding to glutamine and lysine neither of which are located at the predicted carboxyl terminus of the 62-kDa protein.

The second cycle revealed a very strong (>200 pmole) leucine peak indicating the presence of more than one leucine in the polypeptide mixture. The third cycle was somewhat ambiguous due to increasing background. However, arginine was clearly present in the third cycle along with either a glutamic acid or glycine residue. The carboxyl sequencing data supports the existence of a heterogenous, truncated protein.

EXAMPLE 10

62 kDa HEV Antigen Vaccine Confers Full Protection Against Heterologous Wild-Type HEV in Animals

A. TITRATION OF THE CHALLENGE STOCK.

A 10% stool suspension (Mex #14) from a person infected during an HEV epidemic in Telixtac, Mexico (Velazquez, et al., 1990) has previously been reported to cause hepatitis E in experimentally infected cynos (Purdy, et al., 1993). For titration of the challenge stock, four pairs of cynos were injected I.V. with dilutions of a Mexico 14 10% stool suspension prepared in phosphate buffered saline (PBS). Each group of two received 1 ml of either $10^{-2}$, $10^{-5}$, $10^{-6}$, or $10^{-7}$ dilutions.

Animals were monitored for evidence of infection by: 1) serum levels of ALT and SICD, 2) development of antibody to HEV, 3) shedding of HEV in the feces, 4) detection of HEV antigen in the liver, and 5) histopathologic changes (Table 5).

The data in Table 5 demonstrate titration of the Mexico 14 HEV inoculum. Anti-HEV was assayed by ELISA. HEV antigen in liver was detected by immunofluorescent assay of liver biopsy specimens. Liver biopsies were examined under code for necroinflammatory changes. ALT levels were assayed by standard methods (Purdy, et al., 1993).

TABLE 5

TITRATION OF HEV INOCULUM-MEXICO STRAIN

| Cyno No. | Inoculum Dilution | ALT Elevation (days) Range | ALT Elevation (days) Peak (value)[1] | Histo-path. | HEV Ag in liver | Anti-HEV (day of sero-conversion) |
|---|---|---|---|---|---|---|
| 9218 | $10^{-2}$ | 23–65 | 37(5.4) | + | + days 13–28 | + day 20 |
| 9219 | $10^{-2}$ | 16–58 | 30(7.8) | + | + days 13–27 | + day 20 |
| 9214 | $10^{-5}$ | no ALT elevation | | – | – | – |
| 9220 | $10^{-5}$ | 30–37 | 34(4.6) | + | + days 20, 27 | + day 35 |
| 9213 | $10^{-6}$ | 37–52 | 52(1.1) | –/+ | – | + day 35 |
| 9215 | $10^{-6}$ | 49–52 | 49(1.3) | – | – | + day 49 |
| 9212 | $10^{-7}$ | elevated values from day 3 | | – | – | – |
| 9217 | $10^{-7}$ | no ALT elevation | | – | – | – |

[1]peak value/negative cutoff (99% confidence level)

Weekly serum specimens were tested for alanine aminotransferase (ALT) and for anti-HEV antibodies by ELISA. Both animals (cynos #9218, 9219) inoculated with a $10^{-2}$ dilution had elevated ALTs and seroconverted for anti-HEV within three weeks post infection. Only one of the two (50%) cynos inoculated with the $10^{-5}$ dilution had elevated ALTs. This animal, cyno #9220 seroconverted on day 35 post infection. While both animals inoculated with $10^{-6}$ dilution displayed only transient and minimal ALT elevations, these monkeys (cynos #9213 and 9215) did however seroconvert at day 35 and 49. There were no ALT rises or antibody seroconversion in either of the animals inoculated with $10^{-7}$ dilution. Weekly liver biopsy specimens were evaluated histopathologically and by immunofluorescent analysis for the prescence of HEV antigen. Findings of HEV antigen in the liver and histopathologic changes were concordant with the elevation of ALT and observed only in cynos #9218, 9219, and 9220. HEV RNA in cyno stools was assayed by RT-PCR.

The titer of the stock ($CID_{50}$) was defined as the concentration of HEV shown to be infectious in 50% of the cynos tested. The $CID_{50}$ titer of the Mex #14 inoculum was estimated at $10^{-5}$/ml based on biochemical and histologic evidence of hepatitis in one of two cynos inoculated with a $10^{-5}$ dilution of the 10% w/v human stool suspension. A suspension diluted to contain 1000 cynomolgus infectious doses ($CID_{50}$) was used for I.V. challenge of the vaccinated and control cynos.

B. INFECTION OF CONTROL AND VACCINATED TEST ANIMALS.

1. IMMUNIZATION AND CHALLENGE OF ANIMALS.

Fourteen cynomolgus macaques (cynos) were used in the present study. Eight cynos were injected I.V. with dilutions of a 10% stool suspension of the Mexico 14 suspension of HEV for titration of the challenge stock (see above). Six cynos, three vaccinated and three not vaccinated, were used to test for in vivo efficacy of the r62K antigen (Examples 4 and 6B). The monkeys were housed under BSL-2 biohazard containment at the Center for Disease Control and Prevention (Atlanta, Ga.) for the duration of the study.

Animals were quarantined for six weeks and serum specimens were collected weekly for the following six weeks to establish baseline volumes for ALT and SICD. Prior to virus inoculation and vaccination all cyno sera were tested for the presence of antibodies reactive with HEV ORF2 and ORF3 proteins by ELISA (Examples 1 and 8). All animals were HEV antibody negative prior to inoculation.

The r62K (purified as described above, Examples 4 and 6) was precipitated with alum following standard protocols. The protein-alum complex was stored at 4° C. prior to the immunization. Three cynomolgus monkeys (Cynos #9338, 9339, 9340) served as control animals. Each of the animals received I.M. injections of alum on day 0 and day 31. Three cynomolgus monkeys (Cynos #9327, 9330, 9331) were immunized by I.M. injection with 20 ug alum-precipitated r62K protein in 0.5 ml of buffer on day 0 and day 31.

All six of the animals were challenged with a $10^{-2}$ dilution of a 10% human stool suspension containing 1000 $CID_{50}$ of wild-type Mexico HEV (Mex #14) at day 74, 6 weeks after the final immunization.

2. SPECIMEN COLLECTION.

For the eight animals used for titration of the Mexico 14 challenge stock, 1.5 ml blood samples were taken twice weekly. For the six animals used for the vaccine phase of the study, 1.5 ml blood samples were taken weekly. Blood collections continued for at least 120 days. Each specimen was tested for alanine aminotransferase (ALT), serum isocitrate dehydrogenase (SICD), and anti-HEV IgG antibody. A baseline and 99% confidence limit for ALT and SICD activity was established for each animal using pre-inoculation values.

Needle biopsy specimens of liver were collected weekly. Specimens were divided for histopathology and identification of antigen. Biopsies were taken for at least 30 days after liver enzymes return to baseline.

Stool specimens were collected daily, for at least 90 days after challenge, and stored at −70° C. until analysis of viral RNA content.

C. EVALUATION OF COLLECTED SPECIMENS.

1. ELISA FOR ANTI-HEV.

The anti-HEV ELISA was a modification of a previously described EIA protocol (Example 8). Proteins coated to polystyrene ELISA plates as antigens included: ORF2 SG3 (Yarbough, et. al., 1994), ORF3 4–2M (Yarbough, et. al., 1991), and ORF2 r62K. Test sera were incubated in antigen coated wells, followed by gamma chain specific HRP-conjugated goat anti-human IgG (Zymed, South San Francisco, Calif.). The signal to noise value (S/N) for each post-inoculation specimen was calculated as the absorbance at 490 nm divided by the absorbance at 490 nm for the pre-inoculation sera for the same animal. Baseline anti-HEV values were established for each of the monkeys with their five weekly pre-inoculation serum specimens.

The cutoff for anti-HEV reactivity was defined as 0.200 $OD_{490}$ which correlated with a S/N value of 3.39 and greater than 30 standard deviations above the mean of the pre-inoculation O.D. value. Antibody titers were determined by serial 2-fold dilutions with endpoint titers calculated as the greatest serum dilution in a 2-fold dilution sample that still yielded an O.D. of at least 0.200 $OD_{490}$.

2. POLYMERASE CHAIN REACTION (PCR).

A reverse transcriptase-polymerase chain reaction (RT-PCR) method (Kawasaki, et al.; Wang, et al., 1990) was used to assay for HEV RNA in cyno stools. Assays were performed using HEV specific primers derived from published HEV sequences (Tam, et al., 1991a, 1991b; McCaustland, et al., 1991).

3. IMMUNOFLUORESCENT ASSAY.

Immunofluorescent assays for hepatitis E virus antigen in liver biopsy tissue were performed according to Krawczynski and Bradley (1989).

D. HEPATITIS E IN NON-IMMUNIZED ANIMALS.

Biochemical and histologic evidence of hepatitis was observed in two cynos (cynos #9218, 9219) inoculated with a $10^{-2}$ dilution of the challenge stock in the titration study. ALT elevations were observed at two to three weeks post inoculation. Necroinflammatory changes coincided with biochemical evidence of hepatocellular damage. HEV antigen was detected in the livers of the monkeys at two to three weeks post-inoculation. Virus shedding in the stool was observed by RT-PCR.

Antibody to ORF2 of HEV was measurable by day 20. By day 65 ALT levels had began to decline followed by clearing of the virus and resolution of disease.

Biochemical and histologic evidence of hepatitis was observed in three control animals (cynos 9338, 9339, 9340) inoculated with a $10^{-2}$ dilution of the challenge stock in the in vivo efficacy study with r62K (Table 6).

The data presented in Table 6 show the course of Hepatitis E in non-immunized and immunized cynos. Three cynos were immunized by I.M. injection with 0.5 ml of 20 ug alum-precipitated r62K protein on day 0 and day 31. Six cynos were challenged with 1000 $CID_{50}$ of wild-type Mexico HEV (Mex #14) at day 74. Anti-HEV was assayed by ELISA. HEV antigen in liver was detected by immunofluorescent assay of liver biopsy specimens. Liver biopsies were examined under code for necroinflammatory changes. ALT levels were assayed by standard methods. HEV RNA was detected by RT-PCR (Purdy, et al., 1993; Kawasaki, et al.; Wang, et al., 1990).

TABLE 6

HEV VACCINE EXPERIMENT: CHALLENGE WITH HEV MEXICO

| Animal No. | Immunization (62K antigen) | Anti-HEV at Challenge | Elevated Alt (u/l) Range (days) | Elevated Alt (u/l) Peak Day | S/CO |
|---|---|---|---|---|---|
| CY9327 | 2 × 20 ug | positive | 24–87[1] | 83 | 1.3 |
| CY9330 | 2 × 20 ug | positive | 14–104[1] | 41 | 1.5 |
| CY9331 | 2 × 20 ug | positive | single | 97 | 1.5 |
| CY9338 | Alum (× 2) | negative | 11–14 | 20 | 4.5 |
| CY9339 | Alum (× 2) | negative | 20–34 | 27 | 4.7 |
| CY9340 | Alum (× 2) | negative | 27–31 | 27 | 2.5 |

| Animal No. | Histopathology (necro-inflammatory changes) | HEV Ag in liver (days) | HEV RNA in stools (day) |
|---|---|---|---|
| CY9327 | 0 | negative | negative |
| CY9330 | 0 | negative | 30, 24 |
| CY9331 | 0 | negative | negative |
| CY9338 | positive | 14 | nd[2] |
| CY9339 | positive | 14, 20 | 8–20 |
| CY9340 | positive | 14, 20 | nd |

[1]single day, isolated elevations
[2]not determined

ALT elevations with peaks in excess of 2.5 signal/cutoff ratios were exhibited at two to three weeks post challenge for each of the control monkeys. Necroinflammatory changes coincided with biochemical evidence of hepatocellular damage.

HEV antigen was detected in the livers of the three animals within two weeks post challenge. Virus shedding in the stool was observed by RT-PCR as early as one week after challenge in the three control animals. Viral shedding was sustained for as long as three weeks. ALT levels returned to baseline by day 38 post challenge for each of the unvaccinated animals. Antibody to ORF2 of HEV was measurable within three weeks post wild-type challenge for each of the control animals. One animal, cyno #9340, also mounted a coincident ORF3 antibody response.

Concomitant with resolution of disease, antibody to ORF2 of HEV peaked by day 36–41 and persisted for at least 12 weeks after challenge. Antibody to ORF3 was short lived with antibody levels declining by week 12 post challenge. One control animal, cyno #9340, expired between weeks 15–16 post-challenge. The cause of death was essentially unrelated to the HEV infection. The remaining two animals, cyno #9338 and 9339, had declining but still measurable anti-HEV antibody after 21 weeks post-challenge.

E. COMPLETE PROTECTION AGAINST HEPATITIS E IN VACCINATED CYNOS.

Three cynos (# 9327, 9331, and 9330) were immunized twice with 20 ug doses of alum-precipitated r62K ORF2 (Table 6). Anti-HEV antibody directed to ORF2 was initially detected 1–2 weeks following the initial immunization. An anti-HEV ORF2 antibody titer as high as 1:2000 was achieved in all the immunized cynos. Anti-HEV titers continued to rise after the boost immunization for cyno 9327 and 9331. Anti-HEV was still measurable in cyno #9330 but the antibody levels had dropped during the 6 week period between the final boost and the wild-type challenge. Cyno 9327 and 9331 had estimated titers of 1:5000; cyno 9330 had a lower titer of 1:2500 (Table 7).

TABLE 7

SERUM ANTI-HEV INVERSE TITERS: VACCINATED ANIMALS

| Cyno Specimen | Antigen Reactivity | | |
|---|---|---|---|
| | anti-62K | anti-SG3 | anti-4-2 |
| day of challenge | 5,000 | 1,000 | <100 |
| six weeks post-challenge | 2,500 | 500 | <100 |
| day of challenge | 2,500 | 400 | <100 |
| six weeks post-challenge | 20,000 | 2,500 | 1,000 |
| day of challenge | 5,000 | 1,000 | <100 |
| six weeks post-challenge | 2,500 | 500 | <100 |

After challenge with 1000 $CID_{50}$ of the heterologous wild-type HEV, the levels of measurable antibody directed to ORF2 were stable in cyno 9327 and 9331. However, for cyno 9330, there was an apparent anamnestic response observed at six weeks post challenge; endpoint titers rose nearly 10-fold to 1:20,000 (Table 7). Concomitant with the rise in anti-HEV ORF2, cyno 9330 showed an antibody response directed to ORF3.

Although antibody levels continued to rise for the next four weeks, this was abruptly followed by a continuous decrease in antibody to HEV. By 12 weeks after challenge the anti-HEV titers had dropped significantly in cyno 9330; anti-HEV titers remained constant for cyno 9327 and 9331. One vaccinated animal, cyno #9331, died between weeks 16–21 post-challenge. The cause of death was essentially unrelated to the HEV infection. At 21 weeks post challenge, cyno #9327 showed slowly declining antibody directed to ORF2; endpoint titers have only varied 2-fold. At 21 weeks post challenge, #9330 had no measurable antibody to ORF3 and the the antibody titer to ORF2 had dropped more than 20-fold.

For all of the vaccinated animals, ALT levels were near baseline for the duration of the study. There was no detection of antigen in the liver, nor were there any observed necro-inflammatory changes (Table 6). In two of the immunized cynos, virus was not detected by RT-PCR in the feces; in one of the immunized cynos, viral shedding was delayed and in short duration. As there was no biochemical or histopathologic evidence for hepatocellular damage in any of the three immunized animals, vaccination seems to have conferred protection against disease in all the cynos immunized with r62K.

F. EVIDENCE FOR "BREAKTHROUGH" HEPATITIS E INFECTION WITHOUT DISEASE.

The appearance of antibody directed to the ORF3 of HEV in cyno #9330, at six weeks post challenge, suggested that the animal was indeed infected with the challenge virus. This observation was substantiated by the amnestic antibody response to ORF2. Viral shedding in the stool of cyno 9330 was detected by RT-PCR but was delayed in appearance and was of shorter duration relative to control animals (Table 6). Overall, these findings are consistent with breakthrough infection: limited and delayed viral replication in the absence of disease.

The partial protection against infection in cyno 9330 may be accounted for by the fact that the animal had lower levels of anti-HEV prior to challenge. Nevertheless, in the absence of necro-inflammatory changes or biochemical evidence of hepatitis, it appears that hepatocellular damage and hepatitis were prevented by immunization.

EXAMPLE 11

In Vitro HEV Infection and Neutralization

A. CELL CULTURE AND ANTIBODY PREPARATION.

Sera from unvaccinated and vaccinated cynos (described in Example 10) were tested for potential neutralizing antibody using in vitro neutralization assays (see below). Weekly sera samples collected for 5 weeks prior to vaccination were combined to make a pre-bleed sera pool. Sera samples were collected on the day of challenge prior to inoculation of the animals with HEV.

Sera from the control group of three animals (cyno #9338, 9339, 9340) were pooled prior to affinity purification of total immunoglobins (Igs) by protein G column chromatography (Perseptive Biosystems, Cambridge Mass.). Sera from vaccinated animals #9327 and 9330 were individually purified for Igs.

Purified IgG samples were concentrated by speed-vac centrifugation prior to use in the in vitro neutralization assay. Equivalent amounts of ORF2 reactive antibody from each Ig pool were approximated by normalizing according to ELISA end-point titer against the ORF2 SG3 protein.

Normal primary cyno hepatocytes were isolated from liver wedge biopsy. Hepatocytes were plated at a density of $1 \times 10^6$ cells per ml in each well of collagen-coated 6-well plates. In vitro culture of hepatocytes in a serum free medium (SFM) formulation supplemented with growth factors and hormones was as described (Example 2). Plated liver cells were inoculated six days post isolation with either a known infectious HEV inoculum or a pre-incubated mixture of test antibodies and virus stock.

The inoculum used for HEV challenge of the hepatocytes was infectious bile obtained from cyno 11708. This animal had been experimentally infected with a 10% stool suspension from third passage stool, cyno #73 (HEV Burma strain, Bradley, et al., 1987, Purdy, et al., 1993).

Igs from each pre-bleed pool and challenge pool were incubated separately with the virus inoculum for 1 hr at 37° C. with gentle shaking. Warm serum free media (SFM) was added to the antibody-virus mixture and used to inoculate the cultured hepatocytes. Complete medium changes were performed after 24 hours and at 48 hour intervals. Duplicate wells of hepatocyte cultures were used to examine the potential neutralizing activity of each antibody preparation throughout the experiment.

RNA prepared from media and tissue culture cells was analyzed for the presence of positive and negative strand HEV RNA by the use of a strand-specific RT-PCR assay.

B. IN VITRO NEUTRALIZATION OF HEPATITIS E VIRUS BY SERUM ANTIBODIES FROM VACCINATED ANIMALS.

Total IgGs purified from unvaccinated and vaccinated cynos were examined for the presence of potentially neutralizing antibodies to HEV as just described. The data presented in FIG. 15 show the in vitro neutralization of Hepatitis E Virus by serum antibodies from vaccinated animals.

Sera from the control group of unvaccinated animals were pooled. RNA prepared from media and tissue culture cells harvested on day 14 post infection was analyzed for the presence of positive and negative strand HEV RNA by the use of a strand-specific RT-PCR assay.

Figure 15:
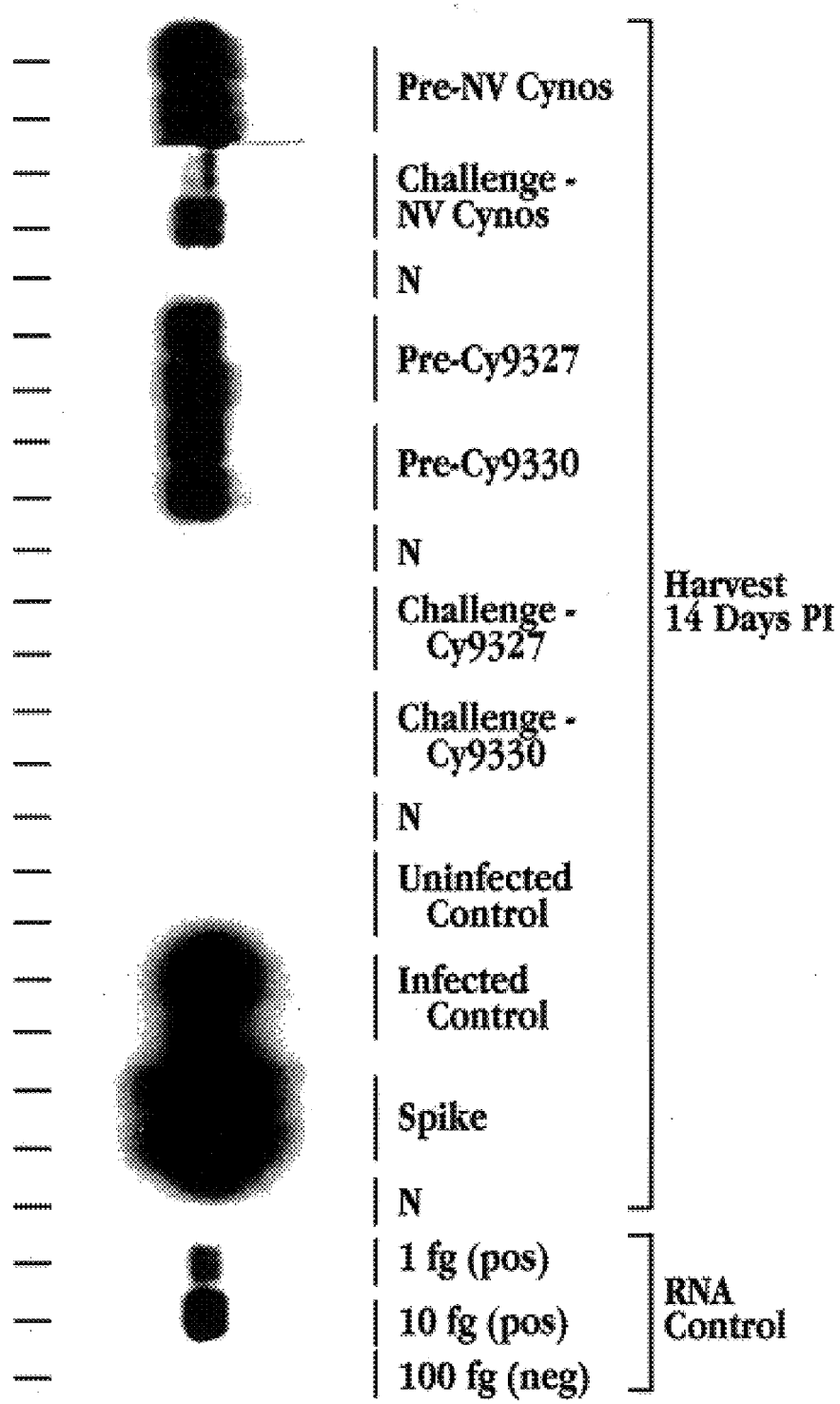
FIG. 15 presents results demonstrating the presence of neutralizing antibodies in r62K HEV antigen vaccinated cyno monkeys.

IgGs (pre-bleed) obtained prior to vaccination for all cynos were incapable of blocking in vitro HEV infection (FIG. 15, "pre-NV (non-vaccinated) cynos", "pre-CY9327" and "pre-CY-9330") as determined by positive strand PCR assay. The observed PCR product correlated with the amount of product observed for infected culture controls that were carried out in the absence of any IgGs.

Pooled IgGs from unvaccinated cynos (9338, 9339, 9340) at the time of challenge did not block the in vitro infection of the cultured hepatocytes (FIG. 15, "challenge NV cynos"). Once again, the observed PCR products correlated with the amount of product observed for infected culture controls that were carried out in the absence of any IgGs.

IgGs taken at the time of challenge from two of the vaccinated cynos (cyno 9327, 9330) appeared to have mounted a neutralizing immune response capable of completely blocking virus infection in vitro (FIG. 15, "challenge CY9327" and "challenge CY9330"). By the positive strand RT-PCR readout, there were no detectable products thereby verifying the absence of HEV viral RNA and validating the neutralizing activity of these cyno antibodies.

In FIG. 15: lanes designated "N" contained no sample; two hepatocyte control lanes are shown, one from an "uninfected control" cell culture and the other from an "infected control" cell culture; the lane designated "spike" is a positive control to show the maximum possible signal that could be obtained from the inoculum itself; and the "RNA control" lanes were used for quantitation and evaluation of the RT-PCR reactions—1 fg positive strand RNA, 10 fg positive strand RNA and 100 fg negative strand RNA.

These observations strengthen the biochemical and histopathologic evidence that antibodies mounted in response to vaccination with the 62K antigen preparation neutralize the HEV virus and confers protection against infection and subsequent disease.

While the invention has been described with reference to particular embodiments, methods, construction and use, it will be apparent to those skilled in the art that various changes and modifications can be made without departing from the invention. For example, short peptides spanning only the immunoreactive region(s) contained in the larger peptides described herein can be substituted for the larger peptides in the methods and kits described and claimed.

What is claimed is:

1. A purified polypeptide from the open reading frame 2 (ORF2) of Hepatitis E Virus having a sequence selected from the group consisting of SEQ ID NO:27 and SEQ ID NO:28, and having an N-terminal methionine.

* * * * *

```
                       SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
        (A) LENGTH: 2049 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
         (C) INDIVIDUAL ISOLATE: Hepatitis E Virus (Burma strain)
             ORF-2

(xi) SEQUENCE DESCRIPTION: SEQ ID NO:1:

ATGCGCCCTC GGCCTATTTT GTTGCTGCTC CTCATGTTTT TGCCTATGCT GCCCGCGCCA      60

CCGCCCGGTC AGCCGTCTGG CCGCCGTCGT GGGCGGCGCA GCGGCGGTTC CGGCGGTGGT     120

TTCTGGGGTG ACCGGGTTGA TTCTCAGCCC TTCGCAATCC CCTATATTCA TCCAACCAAC     180

CCCTTCGCCC CCGATGTCAC CGCTGCGGCC GGGGCTGGAC CTCGTGTTCG CCAACCCGCC     240

CGACCACTCG GCTCCGCTTG GCGTGACCAG GCCCAGCGCC CCGCCGTTGC CTCACGTCGT     300

AGACCTACCA CAGCTGGGGC CGCGCCGCTA ACCGCGGTCG CTCCGGCCCA TGACACCCCG     360

CCAGTGCCTG ATGTCGACTC CCGCGGCGCC ATCTTGCGCC GGCAGTATAA CCTATCAACA     420

TCTCCCCTTA CCTCTTCCGT GGCCACCGGC ACTAACCTGG TTCTTTATGC CGCCCCTCTT     480
```

-continued

| | |
|---|---|
| AGTCCGCTTT TACCCCTTCA GGACGGCACC AATACCCATA TAATGGCCAC GGAAGCTTCT | 540 |
| AATTATGCCC AGTACCGGGT TGCCCGTGCC ACAATCCGTT ACCGCCCGCT GGTCCCCAAT | 600 |
| GCTGTCGGCG GTTACGCCAT CTCCATCTCA TTCTGGCCAC AGACCACCAC CACCCCGACG | 660 |
| TCCGTTGATA TGAATTCAAT AACCTCGACG GATGTTCGTA TTTTAGTCCA GCCCGGCATA | 720 |
| GCCTCTGAGC TTGTGATCCC AAGTGAGCGC CTACACTATC GTAACCAAGG CTGGCGCTCC | 780 |
| GTCGAGACCT CTGGGGTGGC TGAGGAGGAG GCTACCTCTG GTCTTGTTAT GCTTTGCATA | 840 |
| CATGGCTCAC TCGTAAATTC CTATACTAAT ACACCCTATA CCGGTGCCCT CGGGCTGTTG | 900 |
| GACTTTGCCC TTGAGCTTGA GTTTCGCAAC CTTACCCCCG GTAACACCAA TACGCGGGTC | 960 |
| TCCCGTTATT CCAGCACTGC TCGCCACCGC CTTCGTCGCG GTGCGGACGG GACTGCCGAG | 1020 |
| CTCACCACCA CGGCTGCTAC CCGCTTTATG AAGGACCTCT ATTTTACTAG TACTAATGGT | 1080 |
| GTCGGTGAGA TCGCCGCGG GATAGCCCTC ACCCTGTTCA ACCTTGCTGA CACTCTGCTT | 1140 |
| GGCGGCCTGC CGACAGAATT GATTTCGTCG GCTGGTGGCC AGCTGTTCTA CTCCCGTCCC | 1200 |
| GTTGTCTCAG CCAATGGCGA GCCGACTGTT AAGTTGTATA CATCTGTAGA GAATGCTCAG | 1260 |
| CAGGATAAGG GTATTGCAAT CCCGCATGAC ATTGACCTCG GAGAATCTCG TGTGGTTATT | 1320 |
| CAGGATTATG ATAACCAACA TGAACAAGAT CGGCCGACGC CTTCTCCAGC CCATCGCGC | 1380 |
| CCTTTCTCTG TCCTTCGAGC TAATGATGTG CTTTGGCTCT CTCTCACCGC TGCCGAGTAT | 1440 |
| GACCAGTCCA CTTATGGCTC TTCGACTGGC CCAGTTTATG TTTCTGACTC TGTGACCTTG | 1500 |
| GTTAATGTTG CGACCGGCGC GCAGGCCGTT GCCCGGTCGC TCGATTGGAC CAAGGTCACA | 1560 |
| CTTGACGGTC GCCCCCTCTC CACCATCCAG CAGTACTCGA AGACCTTCTT TGTCCTGCCG | 1620 |
| CTCCGCGGTA AGCTCTCTTT CTGGGAGGCA GGCACAACTA AAGCCGGGTA CCCTTATAAT | 1680 |
| TATAACACCA CTGCTAGCGA CCAACTGCTT GTCGAGAATG CCGCCGGGCA CCGGGTCGCT | 1740 |
| ATTTCCACTT ACACCACTAG CCTGGGTGCT GGTCCCGTCT CCATTTCTGC GGTTGCCGTT | 1800 |
| TTAGCCCCCC ACTCTGCGCT AGCATTGCTT GAGGATACCT TGGACTACCC TGCCCGCGCC | 1860 |
| CATACTTTTG ATGATTTCTG CCCAGAGTGC CGCCCCCTTG GCCTTCAGGG CTGCGCTTTC | 1920 |
| CAGTCTACTG TCGCTGAGCT TCAGCGCCTT AAGATGAAGG TGGGTAAAAC TCGGGAGTTG | 1980 |
| TAGTTTATTT GCTTGTGCCC CCCTTCTTTC TGTTGCTTAT TTCTCATTTC TGCGTTCCGC | 2040 |
| GCTCCCTGA | 2049 |

(2) INFORMATION FOR SEQ ID NO:2:

(i) SEQUENCE CHARACTERISTICS:
        (A) LENGTH: 2058 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Hepatitis E Virus (Mexico Strain)
            ORF-2 region (xi) SEQUENCE DESCRIPTION: SEQ ID NO:2:

```
ATGCGCCCTA GGCCTCTTTT GCTGTTGTTC CTCTTGTTTC TGCCTATGTT GCCCGCGCCA     60

CCGACCGGTC AGCCGTCTGG CCGCCGTCGT GGGCGGCGCA GCGGCGGTAC CGGCGGTGGT    120

TTCTGGGGTG ACCGGGTTGA TTCTCAGCCC TTCGCAATCC CCTATATTCA TCCAACCAAC    180
```

-continued

```
CCCTTTGCCC CAGACGTTGC CGCTGCGTCC GGGTCTGGAC CTCGCCTTCG CCAACCAGCC      240

CGGCCACTTG GCTCCACTTG GCGAGATCAG GCCCAGCGCC CCTCCGCTGC CTCCCGTCGC      300

CGACCTGCCA CAGCCGGGGC TGCGGCGCTG ACGGCTGTGG CGCCTGCCCA TGACACCTCA      360

CCCGTCCCGG ACGTTGATTC TCGCGGTGCA ATTCTACGCC GCCAGTATAA TTTGTCTACT      420

TCACCCCTGA CATCCTCTGT GGCCTCTGGC ACTAATTTAG TCCTGTATGC AGCCCCCCTT      480

AATCCGCCTC TGCCGCTGCA GGACGGTACT AATACTCACA TTATGGCCAC AGAGGCCTCC      540

AATTATGCAC AGTACCGGGT TGCCCGCGCT ACTATCCGTT ACCGGCCCCT AGTGCCTAAT      600

GCAGTTGGAG CTATGCTAT ATCCATTTCT TTCTGGCCTC AAACAACCAC AACCCCTACA       660

TCTGTTGACA TGAATTCCAT TACTTCCACT GATGTCAGGA TTCTTGTTCA ACCTGGCATA      720

GCATCTGAAT TGGTCATCCC AAGCGAGCGC CTTCACTACC GCAATCAAGG TTGGCGCTCG      780

GTTGAGACAT CTGGTGTTGC TGAGGAGGAA GCCACCTCCG GTCTTGTCAT GTTATGCATA      840

CATGGCTCTC CAGTTAACTC CTATACCAAT ACCCCTTATA CCGGTGCCCT TGGCTTACTG      900

GACTTTGCCT TAGAGCTTGA GTTTCGCAAT CTCACCACCT GTAACACCAA TACACGTGTG      960

TCCCGTTACT CCAGCACGGC CCGTCACCGG CTCCGCCGAG GGGCCGACGG GACTGCGGAG     1020

CTGACCACAA CTGCAGCCAC CAGGTTCATG AAAGATCTCC ACTTTACCGG CCTTAATGGG     1080

GTAGGTGAAG TCGGCCGCGG GATAGCTCTA ACATTACTTA ACCTTGCTGA CACGCTCCTC     1140

GGCGGGCTCC CGACAGAATT AATTTCGTCG GCTGGCGGGC AACTGTTTTA TTCCCGCCCG     1200

GTTGTCTCAG CCAATGGCGA GCCAACCGTG AAGCTCTATA CATCAGTGGA GAATGCTCAG     1260

CAGGATAAGG GTGTTGCTAT CCCCCACGAT ATCGATCTTG GTGATTCGCG TGTGGTCATT     1320

CAGGATTATG ACAACCAGCA TGAGCAGGAT CGGCCCACCC CGTCGCCTGC GCCATCTCGG     1380

CCTTTTTCTG TTCTCCGAGC AAATGATGTA CTTTGGCTGT CCCTCACTGC AGCCGAGTAT     1440

GACCAGTCCA CTTACGGGTC GTCAACTGGC CCGGTTTATA TCTCGGACAG CGTGACTTTG     1500

GTGAATGTTG CGACTGGCGC GCAGGCCGTA GCCCGATCGC TTGACTGGTC CAAAGTCACC     1560

CTCGACGGGC GGCCCCTCCC GACTGTTGAG CAATATTCCA AGACATTCTT TGTGCTCCCC     1620

CTTCGTGGCA AGCTCTCCTT TTGGGAGGCC GGCACAACAA AAGCAGGTTA TCCTTATAAT     1680

TATAATACTA CTGCTAGTGA CCAGATTCTG ATTGAAAATG CTGCCGGCCA TCGGGTCGCC     1740

ATTTCAACCT ATACCACCAG GCTTGGGGCC GGTCCGGTCG CCATTTCTGC GGCCGCGGTT     1800

TTGGCTCCAC GCTCCGCCCT GGCTCTGCTG GAGGATACTT TGATTATCC GGGGCGGGCG      1860

CACACATTTG ATGACTTCTG CCCTGAATGC CGCGCTTTAG GCCTCCAGGG TTGTGCTTTC     1920

CAGTCAACTG TCGCTGAGCT CCAGCGCCTT AAAGTTAAGG TGGGTAAAAC TCGGGAGTTG     1980

TAGTTTATTT GGCTGTGCCC ACCTACTTAT ATCTGCTGAT TTCCTTTATT TCCTTTTTCT     2040

CGGTCCCGCG CTCCCTGA                                                   2058
```

(2) INFORMATION FOR SEQ ID NO:3:

(i) SEQUENCE CHARACTERISTICS:
        (A) LENGTH: 1647 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Hepatitis E virus (Burma) r62kDa, -continued

FIGURE 2

(xi) SEQUENCE DESCRIPTION: SEQ ID NO:3:

```
GCGGTCGCTC CGGCCCATGA CACCCCGCCA GTGCCTGATG TCGACTCCCG CGGCGCCATC     60
TTGCGCCGGC AGTATAACCT ATCAACATCT CCCCTTACCT CTTCCGTGGC CACCGGCACT    120
AACCTGGTTC TTTATGCCGC CCCTCTTAGT CCGCTTTTAC CCCTTCAGGA CGGCACCAAT    180
ACCCATATAA TGGCCACGGA AGCTTCTAAT TATGCCCAGT ACCGGGTTGC CCGTGCCACA    240
ATCCGTTACC GCCCGCTGGT CCCCAATGCT GTCGGCGGTT ACGCCATCTC CATCTCATTC    300
TGGCCACAGA CCACCACCAC CCCGACGTCC GTTGATATGA ATTCAATAAC CTCGACGGAT    360
GTTCGTATTT TAGTCCAGCC CGGCATAGCC TCTGAGCTTG TGATCCCAAG TGAGCGCCTA    420
CACTATCGTA ACCAAGGCTG GCGCTCCGTC GAGACCTCTG GGGTGGCTGA GGAGGAGGCT    480
ACCTCTGGTC TTGTTATGCT TTGCATACAT GGCTCACTCG TAAATTCCTA TACTAATACA    540
CCCTATACCG GTGCCCTCGG GCTGTTGGAC TTTGCCCTTG AGCTTGAGTT TCGCAACCTT    600
ACCCCCGGTA ACACCAATAC GCGGGTCTCC CGTTATTCCA GCACTGCTCG CCACCGCCTT    660
CGTCGCGGTG CGGACGGGAC TGCCGAGCTC ACCACCACGG CTGCTACCCG CTTTATGAAG    720
GACCTCTATT TTACTAGTAC TAATGGTGTC GGTGAGATCG GCCGCGGGAT AGCCCTCACC    780
CTGTTCAACC TTGCTGACAC TCTGCTTGGC GGCCTGCCGA CAGAATTGAT TTCGTCGGCT    840
GGTGGCCAGC TGTTCTACTC CCGTCCCGTT GTCTCAGCCA ATGGCGAGCC GACTGTTAAG    900
TTGTATACAT CTGTAGAGAA TGCTCAGCAG GATAAGGGTA TTGCAATCCC GCATGACATT    960
GACCTCGGAG AATCTCGTGT GGTTATTCAG GATTATGATA ACCAACATGA ACAAGATCGG   1020
CCGACGCCTT CTCCAGCCCC ATCGCGCCCT TTCTCTGTCC TTCGAGCTAA TGATGTGCTT   1080
TGGCTCTCTC TCACCGCTGC CGAGTATGAC CAGTCCACTT ATGGCTCTTC GACTGGCCCA   1140
GTTTATGTTT CTGACTCTGT GACCTTGGTT AATGTTGCGA CCGGCGCGCA GGCCGTTGCC   1200
CGGTCGCTCG ATTGGACCAA GGTCACACTT GACGGTCGCC CCCTCTCCAC CATCCAGCAG   1260
TACTCGAAGA CCTTCTTTGT CCTGCCGCTC CGCGGTAAGC TCTCTTTCTG GGAGGCAGGC   1320
ACAACTAAAG CCGGGTACCC TTATAATTAT AACACCACTG CTAGCGACCA ACTGCTTGTC   1380
GAGAATGCCG CCGGGCACCG GGTCGCTATT TCCACTTACA CCACTAGCCT GGGTGCTGGT   1440
CCCGTCTCCA TTTCTGCGGT TGCCGTTTTA GCCCCCCACT CTGCGCTAGC ATTGCTTGAG   1500
GATACCTTGG ACTACCCTGC CCGCGCCCAT ACTTTTGATG ATTTCTGCCC AGAGTGCCGC   1560
CCCCTTGGCC TTCAGGGCTG CGCTTTCCAG TCTACTGTCG CTGAGCTTCA GCGCCTTAAG   1620
ATGAAGGTGG GTAAAACTCG GGAGTTG                                       1647
```

(2) INFORMATION FOR SEQ ID NO:4:

(i) SEQUENCE CHARACTERISTICS:
(A) LENGTH: 1647 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: Hepatitis E virus (Mexico strain) r62kDa, FIGURE 2

(xi) SEQUENCE DESCRIPTION: SEQ ID NO:4:

-continued

| | |
|---|---|
| GCTGTGGCGC CTGCCCATGA CACCTCACCC GTCCCGGACG TTGATTCTCG CGGTGCAATT | 60 |
| CTACGCCGCC AGTATAATTT GTCTACTTCA CCCCTGACAT CCTCTGTGGC CTCTGGCACT | 120 |
| AATTTAGTCC TGTATGCAGC CCCCCTTAAT CCGCCTCTGC CGCTGCAGGA CGGTACTAAT | 180 |
| ACTCACATTA TGGCCACAGA GGCCTCCAAT TATGCACAGT ACCGGGTTGC CCGCGCTACT | 240 |
| ATCCGTTACC GGCCCCTAGT GCCTAATGCA GTTGGAGGCT ATGCTATATC CATTTCTTTC | 300 |
| TGGCCTCAAA CAACCACAAC CCCTACATCT GTTGACATGA ATTCCATTAC TTCCACTGAT | 360 |
| GTCAGGATTC TTGTTCAACC TGGCATAGCA TCTGAATTGG TCATCCCAAG CGAGCGCCTT | 420 |
| CACTACCGCA ATCAAGGTTG GCGCTCGGTT GAGACATCTG GTGTTGCTGA GGAGGAAGCC | 480 |
| ACCTCCGGTC TTGTCATGTT ATGCATACAT GGCTCTCCAG TTAACTCCTA TACCAATACC | 540 |
| CCTTATACCG GTGCCCTTGG CTTACTGGAC TTTGCCTTAG AGCTTGAGTT TCGCAATCTC | 600 |
| ACCACCTGTA ACACCAATAC ACGTGTGTCC CGTTACTCCA GCACGGCCCG TCACCGGCTC | 660 |
| CGCCGAGGGG CCGACGGGAC TGCGGAGCTG ACCACAACTG CAGCCACCAG GTTCATGAAA | 720 |
| GATCTCCACT TTACCGGCCT TAATGGGGTA GGTGAAGTCG GCCGCGGGAT AGCTCTAACA | 780 |
| TTACTTAACC TTGCTGACAC GCTCCTCGGC GGGCTCCCGA CAGAATTAAT TTCGTCGGCT | 840 |
| GGCGGGCAAC TGTTTTATTC CCGCCCGGTT GTCTCAGCCA ATGGCGAGCC AACCGTGAAG | 900 |
| CTCTATACAT CAGTGGAGAA TGCTCAGCAG GATAAGGGTG TTGCTATCCC CCACGATATC | 960 |
| GATCTTGGTG ATTCGCGTGT GGTCATTCAG GATTATGACA ACCAGCATGA GCAGGATCGG | 1020 |
| CCCACCCCGT CGCCTGCGCC ATCTCGGCCT TTTTCTGTTC TCCGAGCAAA TGATGTACTT | 1080 |
| TGGCTGTCCC TCACTGCAGC CGAGTATGAC CAGTCCACTT ACGGGTCGTC AACTGGCCCG | 1140 |
| GTTTATATCT CGGACAGCGT GACTTTGGTG AATGTTGCGA CTGGCGCGCA GGCCGTAGCC | 1200 |
| CGATCGCTTG ACTGGTCCAA AGTCACCCTC GACGGGCGGC CCCTCCCGAC TGTTGAGCAA | 1260 |
| TATTCCAAGA CATTCTTTGT GCTCCCCCTT CGTGGCAAGC TCTCCTTTTG GGAGGCCGGC | 1320 |
| ACAACAAAAG CAGGTTATCC TTATAATTAT AATACTACTG CTAGTGACCA GATTCTGATT | 1380 |
| GAAAATGCTG CCGGCCATCG GGTCGCCATT TCAACCTATA CCACCAGGCT TGGGGCCGGT | 1440 |
| CCGGTCGCCA TTTCTGCGGC CGCGGTTTTG GCTCCACGCT CCGCCCTGGC TCTGCTGGAG | 1500 |
| GATACTTTTG ATTATCCGGG GCGGGCGCAC ACATTTGATG ACTTCTGCCC TGAATGCCGC | 1560 |
| GCTTTAGGCC TCCAGGGTTG TGCTTTCCAG TCAACTGTCG CTGAGCTCCA GCGCCTTAAA | 1620 |
| GTTAAGGTGG GTAAAACTCG GGAGTTG | 1647 |

(2) INFORMATION FOR SEQ ID NO:5:

(i) SEQUENCE CHARACTERISTICS:
  (A) LENGTH: 984 base pairs
  (B) TYPE: nucleic acid
  (C) STRANDEDNESS: double
  (D) TOPOLOGY: linear (ii) MOLECULE TYPE: DNA (genomic)

(iii) HYPOTHETICAL: NO (vi) ORIGINAL SOURCE:
  (C) INDIVIDUAL ISOLATE: Hepatitis E Virus (Burma strain) SG3
   region (xi) SEQUENCE DESCRIPTION: SEQ ID NO:5:

| | |
|---|---|
| GGTGCGGACG GGACTGCCGA GCTCACCACC ACGGCTGCTA CCCGCTTTAT GAAGGACCTC | 60 |
| TATTTTACTA GTACTAATGG TGTCGGTGAG ATCGGCCGCG GGATAGCCCT CACCCTGTTC | 120 |

-continued

```
AACCTTGCTG ACACTCTGCT TGGCGGCCTG CCGACAGAAT TGATTTCGTC GGCTGGTGGC    180

CAGCTGTTCT ACTCCCGTCC CGTTGTCTCA GCCAATGGCG AGCCGACTGT TAAGTTGTAT    240

ACATCTGTAG AGAATGCTCA GCAGGATAAG GGTATTGCAA TCCCGCATGA CATTGACCTC    300

GGAGAATCTC GTGTGGTTAT TCAGGATTAT GATAACCAAC ATGAACAAGA TCGGCCGACG    360

CCTTCTCCAG CCCCATCGCG CCCTTTCTCT GTCCTTCGAG CTAATGATGT GCTTTGGCTC    420

TCTCTCACCG CTGCCGAGTA TGACCAGTCC ACTTATGGCT CTTCGACTGG CCCAGTTTAT    480

GTTTCTGACT CTGTGACCTT GGTTAATGTT GCGACCGGCG CGCAGGCCGT TGCCCGGTCG    540

CTCGATTGGA CCAAGGTCAC ACTTGACGGT CGCCCCCTCT CCACCATCCA GCAGTACTCG    600

AAGACCTTCT TTGTCCTGCC GCTCCGCGGT AAGCTCTCTT TCTGGGAGGC AGGCACAACT    660

AAAGCCGGGT ACCCTTATAA TTATAACACC ACTGCTAGCG ACCAACTGCT TGTCGAGAAT    720

GCCGCCGGGC ACCGGGTCGC TATTTCCACT TACACCACTA GCCTGGGTGC TGGTCCCGTC    780

TCCATTTCTG CGGTTGCCGT TTTAGCCCCC CACTCTGCGC TAGCATTGCT TGAGGATACC    840

TTGGACTACC CTGCCCGCGC CCATACTTTT GATGATTTCT GCCCAGAGTG CCGCCCCCTT    900

GGCCTTCAGG GCTGCGCTTT CCAGTCTACT GTCGCTGAGC TTCAGCGCCT TAAGATGAAG    960

GTGGGTAAAA CTCGGGAGTT GTAG                                           984
```

(2) INFORMATION FOR SEQ ID NO:6:

(i) SEQUENCE CHARACTERISTICS:
(A) LENGTH: 984 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: Hepatits E Virus (Mexico strain) SG3 region (xi) SEQUENCE DESCRIPTION: SEQ ID NO:6:

```
GGGGCCGACG GGACTGCGGA GCTGACCACA ACTGCAGCCA CCAGGTTCAT GAAAGATCTC     60

CACTTTACCG GCCTTAATGG GGTAGGTGAA GTCGGCCGCG GGATAGCTCT AACATTACTT    120

AACCTTGCTG ACACGCTCCT CGGCGGGCTC CCGACAGAAT TAATTTCGTC GGCTGGCGGG    180

CAACTGTTTT ATTCCCGCCC GGTTGTCTCA GCCAATGGCG AGCCAACCGT GAAGCTCTAT    240

ACATCAGTGG AGAATGCTCA GCAGGATAAG GGTGTTGCTA TCCCCCACGA TATCGATCTT    300

GGTGATTCGC GTGTGGTCAT TCAGGATTAT GACAACCAGC ATGAGCAGGA TCGGCCCACC    360

CCGTCGCCTG CGCCATCTCG GCCTTTTTCT GTTCTCCGAG CAAATGATGT ACTTTGGCTG    420

TCCCTCACTG CAGCCGAGTA TGACCAGTCC ACTTACGGGT CGTCAACTGG CCCGGTTTAT    480

ATCTCGGACA GCGTGACTTT GGTGAATGTT GCGACTGGCG CGCAGGCCGT AGCCCGATCG    540

CTTGACTGGT CCAAAGTCAC CCTCGACGGG CGGCCCCTCC CGACTGTTGA GCAATATTCC    600

AAGACATTCT TTGTGCTCCC CCTTCGTGGC AAGCTCTCCT TTTGGGAGGC CGGCACAACA    660

AAAGCAGGTT ATCCTTATAA TTATAATACT ACTGCTAGTG ACCAGATTCT GATTGAAAAT    720

GCTGCCGGCC ATCGGGTCGC CATTTCAACC TATACCACCA GGCTTGGGGC CGGTCCGGTC    780

GCCATTTCTG CGGCCGCGGT TTTGGCTCCA CGCTCCGCCC TGGCTCTGCT GGAGGATACT    840

TTTGATTATC CGGGGCGGGC GCACACATTT GATGACTTCT GCCCTGAATG CCGCGCTTTA    900
```

```
GGCCTCCAGG GTTGTGCTTT CCAGTCAACT GTCGCTGAGC TCCAGCGCCT TAAAGTTAAG      960

GTGGGTAAAA CTCGGGAGTT GTAG                                            984
```

(2) INFORMATION FOR SEQ ID NO:7:

(i) SEQUENCE CHARACTERISTICS:
        (A) LENGTH: 147 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Hepatitis E Virus (Burma strain)
            406.3-2

(xi) SEQUENCE DESCRIPTION: SEQ ID NO:7:

```
ACCTTGGACT ACCCTGCCCG CGCCCATACT TTTGATGATT TCTGCCCAGA GTGCCGCCCC       60

CTTGGCCTTC AGGGCTGCGC TTTCCAGTCT ACTGTCGCTG AGCTTCAGCG CCTTAAGATG      120

AAGGTGGGTA AAACTCGGGA GTTGTAG                                         147
```

(2) INFORMATION FOR SEQ ID NO:8:

(i) SEQUENCE CHARACTERISTICS:
        (A) LENGTH: 147 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Hepatitis E Virus (Mexico strain)
            406.3-2

(xi) SEQUENCE DESCRIPTION: SEQ ID NO:8:

```
ACTTTTGATT ATCCGGGGCG GGCGCACACA TTTGATGACT TCTGCCCTGA ATGCCGCGCT       60

TTAGGCCTCC AGGGTTGTGC TTTCCAGTCA ACTGTCGCTG AGCTCCAGCG CCTTAAAGTT      120

AAGGTGGGTA AAACTCGGGA GTTGTAG                                         147
```

(2) INFORMATION FOR SEQ ID NO:9:

(i) SEQUENCE CHARACTERISTICS:
        (A) LENGTH: 372 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Hepatitis E Virus (Burma Strain)
            ORF-3 region (xi) SEQUENCE DESCRIPTION: SEQ ID NO:9:

```
ATGAATAACA TGTCTTTTGC TGCGCCCATG GGTTCGCGAC CATGCGCCCT CGGCCTATTT       60

TGTTGCTGCT CCTCATGTTT TTGCCTATGC TGCCCGCGCC ACCGCCCGGT CAGCCGTCTG      120

GCCGCCGTCG TGGGCGGCGC AGCGGCGGTT CCGGCGGTGG TTTCTGGGGT GACCGGGTTG      180
```

-continued

```
ATTCTCAGCC CTTCGCAATC CCCTATATTC ATCCAACCAA CCCCTTCGCC CCCGATGTCA    240

CCGCTGCGGC CGGGGCTGGA CCTCGTGTTC GCCAACCCGC CCGACCACTC GGCTCCGCTT    300

GGCGTGACCA GGCCCAGCGC CCCGCCGTTG CCTCACGTCG TAGACCTACC ACAGCTGGGG    360

CCGCGCCGCT AA                                                         372
```

(2) INFORMATION FOR SEQ ID NO:10:

(i) SEQUENCE CHARACTERISTICS:
(A) LENGTH: 372 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: Hepatitis E Virus (Mexico Strain) ORF-3 region (xi) SEQUENCE DESCRIPTION: SEQ ID NO:10:

```
ATGAATAACA TGTGGTTTGC TGCGCCCATG GGTTCGCCAC CATGCGCCCT AGGCCTCTTT     60

TGCTGTTGTT CCTCTTGTTT CTGCCTATGT TGCCCGCGCC ACCGACCGGT CAGCCGTCTG    120

GCCGCCGTCG TGGGCGGCGC AGCGGCGGTA CCGGCGGTGG TTTCTGGGGT GACCGGGTTG    180

ATTCTCAGCC CTTCGCAATC CCCTATATTC ATCCAACCAA CCCCTTTGCC CCAGACGTTG    240

CCGCTGCGTC CGGGTCTGGA CCTCGCCTTC GCCAACCAGC CCGGCCACTT GGCTCCACTT    300

GGCGAGATCA GGCCCAGCGC CCCTCCGCTG CCTCCCGTCG CCGACCTGCC ACAGCCGGGG    360

CTGCGGCGCT GA                                                         372
```

(2) INFORMATION FOR SEQ ID NO:11:

(i) SEQUENCE CHARACTERISTICS:
(A) LENGTH: 99 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: Hepatitis E Virus (Burma strain) 406.4-2 region (xi) SEQUENCE DESCRIPTION: SEQ ID NO:11:

```
GCCAACCCGC CCGACCACTC GGCTCCGCTT GGCGTGACCA GGCCCAGCGC CCCGCCGTTG     60

CCTCACGTCG TAGACCTACC ACAGCTGGGG CCGCGCCGC                            99
```

(2) INFORMATION FOR SEQ ID NO:12:

(i) SEQUENCE CHARACTERISTICS:
(A) LENGTH: 99 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: Hepatitis E Virus (Mexico strain)

406.4-2 region (xi) SEQUENCE DESCRIPTION: SEQ ID NO:12:

GCCAACCAGC CCGGCCACTT GGCTCCACTT GGCGAGATCA GGCCCAGCGC CCCTCCGCTG    60

CCTCCCGTCG CCGACCTGCC ACAGCCGGGG CTGCGGCGC                          99

(2) INFORMATION FOR SEQ ID NO:13:

(i) SEQUENCE CHARACTERISTICS:
        (A) LENGTH: 660 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E Virus (Burma strain)
            ORF-2

(xi) SEQUENCE DESCRIPTION: SEQ ID NO:13:

```
Met Arg Pro Arg Pro Ile Leu Leu Leu Leu Met Phe Leu Pro Met
1               5                   10                  15

Leu Pro Ala Pro Pro Gly Gln Pro Ser Gly Arg Arg Arg Gly Arg
            20                  25                  30

Arg Ser Gly Gly Ser Gly Gly Phe Trp Gly Asp Arg Val Asp Ser
            35                  40                  45

Gln Pro Phe Ala Ile Pro Tyr Ile His Pro Thr Asn Pro Phe Ala Pro
50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Val
            85                  90                  95

Ala Ser Arg Arg Arg Pro Thr Thr Ala Gly Ala Ala Pro Leu Thr Ala
            100                 105                 110

Val Ala Pro Ala His Asp Thr Pro Pro Val Pro Asp Val Asp Ser Arg
            115                 120                 125

Gly Ala Ile Leu Arg Arg Gln Tyr Asn Leu Ser Thr Ser Pro Leu Thr
            130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
            165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
            245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Leu Val Asn Ser Tyr
            275                 280                 285
```

```
Thr Asn Thr Pro Tyr Thr Gly Ala Leu Gly Leu Leu Asp Phe Ala Leu
    290                 295                 300
Glu Leu Glu Phe Arg Asn Leu Thr Pro Gly Asn Thr Asn Thr Arg Val
305                 310                 315                 320
Ser Arg Tyr Ser Ser Thr Ala Arg His Arg Leu Arg Arg Gly Ala Asp
            325                 330                 335
Gly Thr Ala Glu Leu Thr Thr Ala Ala Thr Arg Phe Met Lys Asp
            340                 345                 350
Leu Tyr Phe Thr Ser Thr Asn Gly Val Gly Glu Ile Gly Arg Gly Ile
            355                 360                 365
Ala Leu Thr Leu Phe Asn Leu Ala Asp Thr Leu Leu Gly Gly Leu Pro
    370                 375                 380
Thr Glu Leu Ile Ser Ser Ala Gly Gly Gln Leu Phe Tyr Ser Arg Pro
385                 390                 395                 400
Val Val Ser Ala Asn Gly Glu Pro Thr Val Lys Leu Tyr Thr Ser Val
            405                 410                 415
Glu Asn Ala Gln Gln Asp Lys Gly Ile Ala Ile Pro His Asp Ile Asp
            420                 425                 430
Leu Gly Glu Ser Arg Val Val Ile Gln Asp Tyr Asp Asn Gln His Glu
            435                 440                 445
Gln Asp Arg Pro Thr Pro Ser Pro Ala Pro Ser Arg Pro Phe Ser Val
    450                 455                 460
Leu Arg Ala Asn Asp Val Leu Trp Leu Ser Leu Thr Ala Ala Glu Tyr
465                 470                 475                 480
Asp Gln Ser Thr Tyr Gly Ser Ser Thr Gly Pro Val Tyr Val Ser Asp
            485                 490                 495
Ser Val Thr Leu Val Asn Val Ala Thr Gly Ala Gln Ala Val Ala Arg
            500                 505                 510
Ser Leu Asp Trp Thr Lys Val Thr Leu Asp Gly Arg Pro Leu Ser Thr
            515                 520                 525
Ile Gln Gln Tyr Ser Lys Thr Phe Phe Val Leu Pro Leu Arg Gly Lys
    530                 535                 540
Leu Ser Phe Trp Glu Ala Gly Thr Thr Lys Ala Gly Tyr Pro Tyr Asn
545                 550                 555                 560
Tyr Asn Thr Thr Ala Ser Asp Gln Leu Leu Val Glu Asn Ala Ala Gly
            565                 570                 575
His Arg Val Ala Ile Ser Thr Tyr Thr Thr Ser Leu Gly Ala Gly Pro
            580                 585                 590
Val Ser Ile Ser Ala Val Ala Val Leu Ala Pro His Ser Ala Leu Ala
            595                 600                 605
Leu Leu Glu Asp Thr Leu Asp Tyr Pro Ala Arg Ala His Thr Phe Asp
    610                 615                 620
Asp Phe Cys Pro Glu Cys Arg Pro Leu Gly Leu Gln Gly Cys Ala Phe
625                 630                 635                 640
Gln Ser Thr Val Ala Glu Leu Gln Arg Leu Lys Met Lys Val Gly Lys
            645                 650                 655
Thr Arg Glu Leu
            660

(2) INFORMATION FOR SEQ ID NO:14:

(i) SEQUENCE CHARACTERISTICS:
        (A) LENGTH: 660 amino acids
        (B) TYPE: amino acid
```

-continued

```
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E Virus (Mexico Strain)
            ORF-2

(xi) SEQUENCE D

-continued

```
                  355                 360                 365
Ala Leu Thr Leu Leu Asn Leu Ala Asp Thr Leu Leu Gly Gly Leu Pro
        370                 375                 380
Thr Glu Leu Ile Ser Ser Ala Gly Gly Gln Leu Phe Tyr Ser Arg Pro
385                 390                 395                 400
Val Val Ser Ala Asn Gly Glu Pro Thr Val Lys Leu Tyr Thr Ser Val
                405                 410                 415
Glu Asn Ala Gln Gln Asp Lys Gly Val Ala Ile Pro His Asp Ile Asp
                420                 425                 430
Leu Gly Asp Ser Arg Val Val Ile Gln Asp Tyr Asp Asn Gln His Glu
                435                 440                 445
Gln Asp Arg Pro Thr Pro Ser Pro Ala Pro Ser Arg Pro Phe Ser Val
                450                 455                 460
Leu Arg Ala Asn Asp Val Leu Trp Leu Ser Leu Thr Ala Ala Glu Tyr
465                 470                 475                 480
Asp Gln Ser Thr Tyr Gly Ser Ser Thr Gly Pro Val Tyr Ile Ser Asp
                485                 490                 495
Ser Val Thr Leu Val Asn Val Ala Thr Gly Ala Gln Ala Val Ala Arg
                500                 505                 510
Ser Leu Asp Trp Ser Lys Val Thr Leu Asp Gly Arg Pro Leu Pro Thr
                515                 520                 525
Val Glu Gln Tyr Ser Lys Thr Phe Phe Val Leu Pro Leu Arg Gly Lys
                530                 535                 540
Leu Ser Phe Trp Glu Ala Gly Thr Thr Lys Ala Gly Tyr Pro Tyr Asn
545                 550                 555                 560
Tyr Asn Thr Thr Ala Ser Asp Gln Ile Leu Ile Glu Asn Ala Ala Gly
                565                 570                 575
His Arg Val Ala Ile Ser Thr Tyr Thr Thr Arg Leu Gly Ala Gly Pro
                580                 585                 590
Val Ala Ile Ser Ala Ala Ala Val Leu Ala Pro Arg Ser Ala Leu Ala
                595                 600                 605
Leu Leu Glu Asp Thr Phe Asp Tyr Pro Gly Arg Ala His Thr Phe Asp
        610                 615                 620
Asp Phe Cys Pro Glu Cys Arg Ala Leu Gly Leu Gln Gly Cys Ala Phe
625                 630                 635                 640
Gln Ser Thr Val Ala Glu Leu Gln Arg Leu Lys Val Lys Val Gly Lys
                645                 650                 655
Thr Arg Glu Leu
        660
```

(2) INFORMATION FOR SEQ ID NO:15:

(i) SEQUENCE CHARACTERISTICS:
        (A) LENGTH: 549 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E virus (Burma strain)
           r62kDa, FIGURE 4

(xi) SEQUENCE DESCRIPTION: SEQ ID NO:15:

Ala Val Ala Pro Ala His Asp Thr Pro Pro Val Pro Asp Val Asp Ser

```
1               5                    10                   15

Arg Gly Ala Ile Leu Arg Arg Gln Tyr Asn Leu Ser Thr Ser Pro Leu
                20                  25                  30

Thr Ser Ser Val Ala Thr Gly Thr Asn Leu Val Leu Tyr Ala Ala Pro
            35                  40                  45

Leu Ser Pro Leu Leu Pro Leu Gln Asp Gly Thr Asn Thr His Ile Met
        50                  55                  60

Ala Thr Glu Ala Ser Asn Tyr Ala Gln Tyr Arg Val Ala Arg Ala Thr
65                  70                  75                  80

Ile Arg Tyr Arg Pro Leu Val Pro Asn Ala Val Gly Tyr Ala Ile
                85                  90                  95

Ser Ile Ser Phe Trp Pro Gln Thr Thr Thr Pro Thr Ser Val Asp
                100                 105                 110

Met Asn Ser Ile Thr Ser Thr Asp Val Arg Ile Leu Val Gln Pro Gly
                115                 120                 125

Ile Ala Ser Glu Leu Val Ile Pro Ser Glu Arg Leu His Tyr Arg Asn
        130                 135                 140

Gln Gly Trp Arg Ser Val Glu Thr Ser Gly Val Ala Glu Glu Ala
145                 150                 155                 160

Thr Ser Gly Leu Val Met Leu Cys Ile His Gly Ser Leu Val Asn Ser
                165                 170                 175

Tyr Thr Asn Thr Pro Tyr Thr Gly Ala Leu Gly Leu Leu Asp Phe Ala
                180                 185                 190

Leu Glu Leu Glu Phe Arg Asn Leu Thr Pro Gly Asn Thr Asn Thr Arg
        195                 200                 205

Val Ser Arg Tyr Ser Ser Thr Ala Arg His Arg Leu Arg Arg Gly Ala
    210                 215                 220

Asp Gly Thr Ala Glu Leu Thr Thr Thr Ala Ala Thr Arg Phe Met Lys
225                 230                 235                 240

Asp Leu Tyr Phe Thr Ser Thr Asn Gly Val Gly Glu Ile Gly Arg Gly
                245                 250                 255

Ile Ala Leu Thr Leu Phe Asn Leu Ala Asp Thr Leu Leu Gly Gly Leu
                260                 265                 270

Pro Thr Glu Leu Ile Ser Ser Ala Gly Gly Gln Leu Phe Tyr Ser Arg
            275                 280                 285

Pro Val Val Ser Ala Asn Gly Glu Pro Thr Val Lys Leu Tyr Thr Ser
    290                 295                 300

Val Glu Asn Ala Gln Gln Asp Lys Gly Ile Ala Ile Pro His Asp Ile
305                 310                 315                 320

Asp Leu Gly Glu Ser Arg Val Val Ile Gln Asp Tyr Asp Asn Gln His
                325                 330                 335

Glu Gln Asp Arg Pro Thr Pro Ser Pro Ala Pro Ser Arg Pro Phe Ser
            340                 345                 350

Val Leu Arg Ala Asn Asp Val Leu Trp Leu Ser Leu Thr Ala Ala Glu
                355                 360                 365

Tyr Asp Gln Ser Thr Tyr Gly Ser Ser Thr Gly Pro Val Tyr Val Ser
            370                 375                 380

Asp Ser Val Thr Leu Val Asn Val Ala Thr Gly Ala Gln Ala Val Ala
385                 390                 395                 400

Arg Ser Leu Asp Trp Thr Lys Val Thr Leu Asp Gly Arg Pro Leu Ser
                405                 410                 415

Thr Ile Gln Gln Tyr Ser Lys Thr Phe Phe Val Leu Pro Leu Arg Gly
                420                 425                 430
```

```
Lys Leu Ser Phe Trp Glu Ala Gly Thr Thr Lys Ala Gly Tyr Pro Tyr
            435                 440                 445

Asn Tyr Asn Thr Thr Ala Ser Asp Gln Leu Leu Val Glu Asn Ala Ala
        450                 455                 460

Gly His Arg Val Ala Ile Ser Thr Tyr Thr Thr Ser Leu Gly Ala Gly
465                 470                 475                 480

Pro Val Ser Ile Ser Ala Val Ala Val Leu Ala Pro His Ser Ala Leu
                485                 490                 495

Ala Leu Leu Glu Asp Thr Leu Asp Tyr Pro Ala Arg Ala His Thr Phe
            500                 505                 510

Asp Asp Phe Cys Pro Glu Cys Arg Pro Leu Gly Leu Gln Gly Cys Ala
            515                 520                 525

Phe Gln Ser Thr Val Ala Glu Leu Gln Arg Leu Lys Met Lys Val Gly
            530                 535                 540

Lys Thr Arg Glu Leu
545

(2) INFORMATION FOR SEQ ID NO:16:

(i) SEQUENCE CHARACTERISTICS:
        (A) LENGTH: 549 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E virus (Mexico strain)
            r62kDa, FIGURE 4

(xi) SEQUENCE DESCRIPTION: SEQ ID NO:16:

Ala Val Ala Pro Ala His Asp Thr Ser Pro Val Pro Asp Val Asp Ser
1               5                   10                  15

Arg Gly Ala Ile Leu Arg Arg Gln Tyr Asn Leu Ser Thr Ser Pro Leu
            20                  25                  30

Thr Ser Ser Val Ala Ser Gly Thr Asn Leu Val Leu Tyr Ala Ala Pro
        35                  40                  45

Leu Asn Pro Pro Leu Pro Leu Gln Asp Gly Thr Asn Thr His Ile Met
50                  55                  60

Ala Thr Glu Ala Ser Asn Tyr Ala Gln Tyr Arg Val Ala Arg Ala Thr
65                  70                  75                  80

Ile Arg Tyr Arg Pro Leu Val Pro Asn Ala Val Gly Gly Tyr Ala Ile
            85                  90                  95

Ser Ile Ser Phe Trp Pro Gln Thr Thr Thr Thr Pro Thr Ser Val Asp
            100                 105                 110

Met Asn Ser Ile Thr Ser Thr Asp Val Arg Ile Leu Val Gln Pro Gly
        115                 120                 125

Ile Ala Ser Glu Leu Val Ile Pro Ser Glu Arg Leu His Tyr Arg Asn
130                 135                 140

Gln Gly Trp Arg Ser Val Glu Thr Ser Gly Val Ala Glu Glu Glu Ala
145                 150                 155                 160

Thr Ser Gly Leu Val Met Leu Cys Ile His Gly Ser Pro Val Asn Ser
            165                 170                 175

Tyr Thr Asn Thr Pro Tyr Thr Gly Ala Leu Gly Leu Leu Asp Phe Ala
            180                 185                 190
```

```
Leu Glu Leu Glu Phe Arg Asn Leu Thr Thr Cys Asn Thr Asn Thr Arg
            195                 200                 205

Val Ser Arg Tyr Ser Ser Thr Ala Arg His Arg Leu Arg Arg Gly Ala
    210                 215                 220

Asp Gly Thr Ala Glu Leu Thr Thr Ala Ala Thr Arg Phe Met Lys
225                 230                 235                 240

Asp Leu His Phe Thr Gly Leu Asn Gly Val Gly Val Gly Arg Gly
                245                 250                 255

Ile Ala Leu Thr Leu Leu Asn Leu Ala Asp Thr Leu Leu Gly Gly Leu
            260                 265                 270

Pro Thr Glu Leu Ile Ser Ser Ala Gly Gly Gln Leu Phe Tyr Ser Arg
            275                 280                 285

Pro Val Val Ser Ala Asn Gly Glu Pro Thr Val Lys Leu Tyr Thr Ser
            290                 295                 300

Val Glu Asn Ala Gln Gln Asp Lys Gly Val Ala Ile Pro His Asp Ile
305                 310                 315                 320

Asp Leu Gly Asp Ser Arg Val Val Ile Gln Asp Tyr Asp Asn Gln His
                325                 330                 335

Glu Gln Asp Arg Pro Thr Pro Ser Pro Ala Pro Ser Arg Pro Phe Ser
            340                 345                 350

Val Leu Arg Ala Asn Asp Val Leu Trp Leu Ser Leu Thr Ala Ala Glu
            355                 360                 365

Tyr Asp Gln Ser Thr Tyr Gly Ser Ser Thr Gly Pro Val Tyr Ile Ser
            370                 375                 380

Asp Ser Val Thr Leu Val Asn Val Ala Thr Gly Ala Gln Ala Val Ala
385                 390                 395                 400

Arg Ser Leu Asp Trp Ser Lys Val Thr Leu Asp Gly Arg Pro Leu Pro
                405                 410                 415

Thr Val Glu Gln Tyr Ser Lys Thr Phe Phe Val Leu Pro Leu Arg Gly
            420                 425                 430

Lys Leu Ser Phe Trp Glu Ala Gly Thr Thr Lys Ala Gly Tyr Pro Tyr
            435                 440                 445

Asn Tyr Asn Thr Thr Ala Ser Asp Gln Ile Leu Ile Glu Asn Ala Ala
450                 455                 460

Gly His Arg Val Ala Ile Ser Thr Tyr Thr Thr Arg Leu Gly Ala Gly
465                 470                 475                 480

Pro Val Ala Ile Ser Ala Ala Val Leu Ala Pro Arg Ser Ala Leu
                485                 490                 495

Ala Leu Leu Glu Asp Thr Phe Asp Tyr Pro Gly Arg Ala His Thr Phe
            500                 505                 510

Asp Asp Phe Cys Pro Glu Cys Arg Ala Leu Gly Leu Gln Gly Cys Ala
            515                 520                 525

Phe Gln Ser Thr Val Ala Glu Leu Gln Arg Leu Lys Val Lys Val Gly
            530                 535                 540

Lys Thr Arg Glu Leu
545
```

(2) INFORMATION FOR SEQ ID NO:17:

(i) SEQUENCE CHARACTERISTICS:
        (A) LENGTH: 327 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E Virus (Burma strain) SG3
            region (xi) SEQUENCE DESCRIPTION: SEQ ID NO:17:

```
Gly Ala Asp Gly Thr Ala Glu Leu Thr Thr Thr Ala Ala Thr Arg Phe
1               5                   10                  15

Met Lys Asp Leu Tyr Phe Thr Ser Thr Asn Gly Val Gly Glu Ile Gly
                20                  25                  30

Arg Gly Ile Ala Leu Thr Leu Phe Asn Leu Ala Asp Thr Leu Leu Gly
            35                  40                  45

Gly Leu Pro Thr Glu Leu Ile Ser Ser Ala Gly Gly Gln Leu Phe Tyr
50                      55                  60

Ser Arg Pro Val Val Ser Ala Asn Gly Glu Pro Thr Val Lys Leu Tyr
65                  70                  75                  80

Thr Ser Val Glu Asn Ala Gln Gln Asp Lys Gly Ile Ala Ile Pro His
                85                  90                  95

Asp Ile Asp Leu Gly Glu Ser Arg Val Val Ile Gln Asp Tyr Asp Asn
                100                 105                 110

Gln His Glu Gln Asp Arg Pro Thr Pro Ser Pro Ala Pro Ser Arg Pro
            115                 120                 125

Phe Ser Val Leu Arg Ala Asn Asp Val Leu Trp Leu Ser Leu Thr Ala
130                     135                 140

Ala Glu Tyr Asp Gln Ser Thr Tyr Gly Ser Ser Thr Gly Pro Val Tyr
145                 150                 155                 160

Val Ser Asp Ser Val Thr Leu Val Asn Val Ala Thr Gly Ala Gln Ala
                165                 170                 175

Val Ala Arg Ser Leu Asp Trp Thr Lys Val Thr Leu Asp Gly Arg Pro
            180                 185                 190

Leu Ser Thr Ile Gln Gln Tyr Ser Lys Thr Phe Phe Val Leu Pro Leu
            195                 200                 205

Arg Gly Lys Leu Ser Phe Trp Glu Ala Gly Thr Thr Lys Ala Gly Tyr
210                 215                 220

Pro Tyr Asn Tyr Asn Thr Thr Ala Ser Asp Gln Leu Leu Val Glu Asn
225                 230                 235                 240

Ala Ala Gly His Arg Val Ala Ile Ser Thr Tyr Thr Thr Ser Leu Gly
                245                 250                 255

Ala Gly Pro Val Ser Ile Ser Ala Val Ala Val Leu Ala Pro His Ser
                260                 265                 270

Ala Leu Ala Leu Leu Glu Asp Thr Leu Asp Tyr Pro Ala Arg Ala His
            275                 280                 285

Thr Phe Asp Asp Phe Cys Pro Glu Cys Arg Pro Leu Gly Leu Gln Gly
            290                 295                 300

Cys Ala Phe Gln Ser Thr Val Ala Glu Leu Gln Arg Leu Lys Met Lys
305                 310                 315                 320

Val Gly Lys Thr Arg Glu Leu
                325
```

(2) INFORMATION FOR SEQ ID NO:18:

(i) SEQUENCE CHARACTERISTICS:
        (A) LENGTH: 327 amino acids
        (B) TYPE: amino acid
        (D) TOPOLOGY: linear (ii) MOLECULE TYPE: protein (iii) HYPOTHETICAL: NO (vi) ORIGINAL SOURCE:
  (C) INDIVIDUAL ISOLATE: Hepatitis E Virus (Mexico strain) SG3 region (xi) SEQUENCE DESCRIPTION: SEQ ID NO:18:

```
Gly Ala Asp Gly Thr Ala Glu Leu Thr Thr Thr Ala Ala Thr Arg Phe
1               5                   10                  15

Met Lys Asp Leu His Phe Thr Gly Leu Asn Gly Val Gly Glu Val Gly
                20                  25                  30

Arg Gly Ile Ala Leu Thr Leu Leu Asn Leu Ala Asp Thr Leu Leu Gly
            35                  40                  45

Gly Leu Pro Thr Glu Leu Ile Ser Ser Ala Gly Gln Leu Phe Tyr
        50                  55                  60

Ser Arg Pro Val Val Ser Ala Asn Gly Glu Pro Thr Val Lys Leu Tyr
65                  70                  75                  80

Thr Ser Val Glu Asn Ala Gln Gln Asp Lys Gly Val Ala Ile Pro His
                85                  90                  95

Asp Ile Asp Leu Gly Asp Ser Arg Val Val Ile Gln Asp Tyr Asp Asn
                100                 105                 110

Gln His Glu Gln Asp Arg Pro Thr Pro Ser Pro Ala Pro Ser Arg Pro
            115                 120                 125

Phe Ser Val Leu Arg Ala Asn Asp Val Leu Trp Leu Ser Leu Thr Ala
130                 135                 140

Ala Glu Tyr Asp Gln Ser Thr Tyr Gly Ser Ser Thr Gly Pro Val Tyr
145                 150                 155                 160

Ile Ser Asp Ser Val Thr Leu Val Asn Val Ala Thr Gly Ala Gln Ala
                165                 170                 175

Val Ala Arg Ser Leu Asp Trp Ser Lys Val Thr Leu Asp Gly Arg Pro
            180                 185                 190

Leu Pro Thr Val Glu Gln Tyr Ser Lys Thr Phe Phe Val Leu Pro Leu
        195                 200                 205

Arg Gly Lys Leu Ser Phe Trp Glu Ala Gly Thr Thr Lys Ala Gly Tyr
210                 215                 220

Pro Tyr Asn Tyr Asn Thr Thr Ala Ser Asp Gln Ile Leu Ile Glu Asn
225                 230                 235                 240

Ala Ala Gly His Arg Val Ala Ile Ser Thr Tyr Thr Thr Arg Leu Gly
                245                 250                 255

Ala Gly Pro Val Ala Ile Ser Ala Ala Val Leu Ala Pro Arg Ser
            260                 265                 270

Ala Leu Ala Leu Leu Glu Asp Thr Phe Asp Tyr Pro Gly Arg Ala His
        275                 280                 285

Thr Phe Asp Asp Phe Cys Pro Glu Cys Arg Ala Leu Gly Leu Gln Gly
290                 295                 300

Cys Ala Phe Gln Ser Thr Val Ala Glu Leu Gln Arg Leu Lys Val Lys
305                 310                 315                 320

Val Gly Lys Thr Arg Glu Leu
                325
```

(2) INFORMATION FOR SEQ ID NO:19:

(i) SEQUENCE CHARACTERISTICS:
    (A) LENGTH: 33 amino acids (B) TYPE: amino acid
            (D) TOPOLOGY: linear (ii) MOLECULE TYPE: protein (iii) HYPOTHETICAL: NO (vi) ORIGINAL SOURCE:
            (C) INDIVIDUAL ISOLATE: Hepatitis E Virus (Burma strain)
                406.4-2

(xi) SEQUENCE DESCRIPTION: SEQ ID NO:19:

```
Ala Asn Pro Pro Asp His Ser Ala Pro Leu Gly Val Thr Arg Pro Ser
1               5                  10                  15

Ala Pro Pro Leu Pro His Val Val Asp Leu Pro Gln Leu Gly Pro Arg
            20                  25                  30

Arg
```

(2) INFORMATION FOR SEQ ID NO:20:

(i) SEQUENCE CHARACTERISTICS:
            (A) LENGTH: 33 amino acids
            (B) TYPE: amino acid
            (D) TOPOLOGY: linear (ii) MOLECULE TYPE: protein (iii) HYPOTHETICAL: NO (vi) ORIGINAL SOURCE:
            (C) INDIVIDUAL ISOLATE: Hepatitis E Virus (Mexico strain)
                406.4-2

(xi) SEQUENCE DESCRIPTION: SEQ ID NO:20:

```
Ala Asn Gln Pro Gly His Leu Ala Pro Leu Gly Glu Ile Arg Pro Ser
1               5                  10                  15

Ala Pro Pro Leu Pro Pro Val Ala Asp Leu Pro Gln Pro Gly Leu Arg
            20                  25                  30

Arg
```

(2) INFORMATION FOR SEQ ID NO:21:

(i) SEQUENCE CHARACTERISTICS:
            (A) LENGTH: 124 amino acids
            (B) TYPE: amino acid
            (D) TOPOLOGY: linear (ii) MOLECULE TYPE: protein (iii) HYPOTHETICAL: NO (vi) ORIGINAL SOURCE:
            (C) INDIVIDUAL ISOLATE: Hepatitis E Virus (Burma Strain)
                ORF-3

(xi) SEQUENCE DESCRIPTION: SEQ ID NO:21:

```
Met Asn Asn Met Ser Phe Ala Ala Pro Met Gly Ser Arg Pro Cys Ala
1               5                  10                  15

Leu Gly Leu Phe Cys Cys Cys Ser Ser Cys Phe Cys Leu Cys Cys Pro
            20                  25                  30

Arg His Arg Pro Val Ser Arg Leu Ala Ala Val Val Gly Gly Ala Ala
        35                  40                  45

Ala Val Pro Ala Val Val Ser Gly Val Thr Gly Leu Ile Leu Ser Pro
    50                  55                  60

Ser Gln Ser Pro Ile Phe Ile Gln Pro Thr Pro Ser Pro Pro Met Ser
65                  70                  75                  80
```

```
Pro Leu Arg Pro Gly Leu Asp Leu Val Phe Ala Asn Pro Pro Asp His
                85                  90                  95

Ser Ala Pro Leu Gly Val Thr Arg Pro Ser Ala Pro Pro Leu Pro His
            100                 105                 110

Val Val Asp Leu Pro Gln Leu Gly Pro Arg Arg Glx
        115                 120
```

(2) INFORMATION FOR SEQ ID NO:22:

(i) SEQUENCE CHARACTERISTICS:
        (A) LENGTH: 124 amino acids
        (B) TYPE: amino acid
        (D) TOPOLOGY: linear (ii) MOLECULE TYPE: protein (iii) HYPOTHETICAL: NO (vi) ORIGINAL SOURCE:
       (C) INDIVIDUAL ISOLATE: Hepatitis E Virus (Mexico Strain)
          ORF-3

(xi) SEQUENCE DESCRIPTION: SEQ ID NO:22:

```
Met Asn Asn Met Trp Phe Ala Ala Pro Met Gly Ser Pro Pro Cys Ala
1               5                   10                  15

Leu Gly Leu Phe Cys Cys Cys Ser Ser Cys Phe Cys Leu Cys Cys Pro
            20                  25                  30

Arg His Arg Pro Val Ser Arg Leu Ala Ala Val Gly Gly Ala Ala
        35                  40                  45

Ala Val Pro Ala Val Val Ser Gly Val Thr Gly Leu Ile Leu Ser Pro
    50                  55                  60

Ser Gln Ser Pro Ile Phe Ile Gln Pro Thr Pro Leu Pro Gln Thr Leu
65                  70                  75                  80

Pro Leu Arg Pro Gly Leu Asp Leu Ala Phe Ala Asn Gln Pro Gly His
                85                  90                  95

Leu Ala Pro Leu Gly Glu Ile Arg Pro Ser Ala Pro Pro Leu Pro Pro
            100                 105                 110

Val Ala Asp Leu Pro Gln Pro Gly Leu Arg Arg Glx
        115                 120
```

(2) INFORMATION FOR SEQ ID NO:23:

(i) SEQUENCE CHARACTERISTICS:
        (A) LENGTH: 48 amino acids
        (B) TYPE: amino acid
        (D) TOPOLOGY: linear (ii) MOLECULE TYPE: protein (iii) HYPOTHETICAL: NO (vi) ORIGINAL SOURCE:
       (C) INDIVIDUAL ISOLATE: Hepatitis E Virus (Burma strain)
         406.3-2

(xi) SEQUENCE DESCRIPTION: SEQ ID NO:23:

```
Thr Leu Asp Tyr Pro Ala Arg Ala His Thr Phe Asp Asp Phe Cys Pro
1               5                   10                  15

Glu Cys Arg Pro Leu Gly Leu Gln Gly Cys Ala Phe Gln Ser Thr Val
            20                  25                  30

Ala Glu Leu Gln Arg Leu Lys Met Lys Val Gly Lys Thr Arg Glu Leu
            35                  40                  45
```

(2) INFORMATION FOR SEQ ID NO:24:

(i) SEQUENCE CHARACTERISTICS:
        (A) LENGTH: 48 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E Virus (Mexico strain)
            406.3-2 region (xi) SEQUENCE DESCRIPTION: SEQ ID NO:24:

```
Thr Phe Asp Tyr Pro Gly Arg Ala His Thr Phe Asp Asp Phe Cys Pro
  1               5                  10                  15

Glu Cys Arg Ala Leu Gly Leu Gln Gly Cys Ala Phe Gln Ser Thr Val
             20                  25                  30

Ala Glu Leu Gln Arg Leu Lys Val Lys Val Gly Lys Thr Arg Glu Leu
             35                  40                  45
```

(2) INFORMATION FOR SEQ ID NO:25:

(i) SEQUENCE CHARACTERISTICS:
        (A) LENGTH: 540 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E virus (Burma strain)
            r62kDa, 58.1 kDa (xi) SEQUENCE DESCRIPTION: SEQ ID NO:25:

```
Ala Val Ala Pro Ala His Asp Thr Pro Pro Val Pro Asp Val Asp Ser
  1               5                  10                  15

Arg Gly Ala Ile Leu Arg Arg Gln Tyr Asn Leu Ser Thr Ser Pro Leu
             20                  25                  30

Thr Ser Ser Val Ala Thr Gly Thr Asn Leu Val Leu Tyr Ala Ala Pro
             35                  40                  45

Leu Ser Pro Leu Leu Pro Leu Gln Asp Gly Thr Asn Thr His Ile Met
 50                  55                  60

Ala Thr Glu Ala Ser Asn Tyr Ala Gln Tyr Arg Val Ala Arg Ala Thr
 65                  70                  75                  80

Ile Arg Tyr Arg Pro Leu Val Pro Asn Ala Val Gly Gly Tyr Ala Ile
             85                  90                  95

Ser Ile Ser Phe Trp Pro Gln Thr Thr Thr Thr Pro Thr Ser Val Asp
            100                 105                 110

Met Asn Ser Ile Thr Ser Thr Asp Val Arg Ile Leu Val Gln Pro Gly
            115                 120                 125

Ile Ala Ser Glu Leu Val Ile Pro Ser Glu Arg Leu His Tyr Arg Asn
            130                 135                 140

Gln Gly Trp Arg Ser Val Glu Thr Ser Gly Val Ala Glu Glu Glu Ala
145                 150                 155                 160

Thr Ser Gly Leu Val Met Leu Cys Ile His Gly Ser Leu Val Asn Ser
            165                 170                 175
```

Tyr Thr Asn Thr Pro Tyr Thr Gly Ala Leu Gly Leu Leu Asp Phe Ala
            180                 185                 190

Leu Glu Leu Glu Phe Arg Asn Leu Thr Pro Gly Asn Thr Asn Thr Arg
            195                 200                 205

Val Ser Arg Tyr Ser Ser Thr Ala Arg His Arg Leu Arg Arg Gly Ala
            210                 215                 220

Asp Gly Thr Ala Glu Leu Thr Thr Ala Ala Thr Arg Phe Met Lys
225                 230                 235                 240

Asp Leu Tyr Phe Thr Ser Thr Asn Gly Val Gly Glu Ile Gly Arg Gly
            245                 250                 255

Ile Ala Leu Thr Leu Phe Asn Leu Ala Asp Thr Leu Leu Gly Gly Leu
            260                 265                 270

Pro Thr Glu Leu Ile Ser Ser Ala Gly Gly Gln Leu Phe Tyr Ser Arg
            275                 280                 285

Pro Val Val Ser Ala Asn Gly Glu Pro Thr Val Lys Leu Tyr Thr Ser
            290                 295                 300

Val Glu Asn Ala Gln Gln Asp Lys Gly Ile Ala Ile Pro His Asp Ile
305                 310                 315                 320

Asp Leu Gly Glu Ser Arg Val Val Ile Gln Asp Tyr Asp Asn Gln His
            325                 330                 335

Glu Gln Asp Arg Pro Thr Pro Ser Pro Ala Pro Ser Arg Pro Phe Ser
            340                 345                 350

Val Leu Arg Ala Asn Asp Val Leu Trp Leu Ser Leu Thr Ala Ala Glu
            355                 360                 365

Tyr Asp Gln Ser Thr Tyr Gly Ser Ser Thr Gly Pro Val Tyr Val Ser
            370                 375                 380

Asp Ser Val Thr Leu Val Asn Val Ala Thr Gly Ala Gln Ala Val Ala
385                 390                 395                 400

Arg Ser Leu Asp Trp Thr Lys Val Thr Leu Asp Gly Arg Pro Leu Ser
            405                 410                 415

Thr Ile Gln Gln Tyr Ser Lys Thr Phe Phe Val Leu Pro Leu Arg Gly
            420                 425                 430

Lys Leu Ser Phe Trp Glu Ala Gly Thr Thr Lys Ala Gly Tyr Pro Tyr
            435                 440                 445

Asn Tyr Asn Thr Thr Ala Ser Asp Gln Leu Leu Val Glu Asn Ala Ala
            450                 455                 460

Gly His Arg Val Ala Ile Ser Thr Tyr Thr Thr Ser Leu Gly Ala Gly
465                 470                 475                 480

Pro Val Ser Ile Ser Ala Val Ala Val Leu Ala Pro His Ser Ala Leu
            485                 490                 495

Ala Leu Leu Glu Asp Thr Leu Asp Tyr Pro Ala Arg Ala His Thr Phe
            500                 505                 510

Asp Asp Phe Cys Pro Glu Cys Arg Pro Leu Gly Leu Gln Gly Cys Ala
            515                 520                 525

Phe Gln Ser Thr Val Ala Glu Leu Gln Arg Leu Lys
            530                 535                 540

(2) INFORMATION FOR SEQ ID NO:26:

(i) SEQUENCE CHARACTERISTICS:
        (A) LENGTH: 540 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
    (C) INDIVIDUAL ISOLATE: Hepatitis E virus (Mexico strain) r62kDa, 58.1 kDa (xi) SEQUENCE DESCRIPTION: SEQ ID NO:26:

```
Ala Val Ala Pro Ala His Asp Thr Ser Pro Val Pro Asp Val Asp Ser
1               5                   10                  15

Arg Gly Ala Ile Leu Arg Arg Gln Tyr Asn Leu Ser Thr Ser Pro Leu
            20                  25                  30

Thr Ser Ser Val Ala Ser Gly Thr Asn Leu Val Leu Tyr Ala Ala Pro
            35                  40                  45

Leu Asn Pro Pro Leu Pro Leu Gln Asp Gly Thr Asn Thr His Ile Met
        50                  55                  60

Ala Thr Glu Ala Ser Asn Tyr Ala Gln Tyr Arg Val Ala Arg Ala Thr
65                  70                  75                  80

Ile Arg Tyr Arg Pro Leu Val Pro Asn Ala Val Gly Gly Tyr Ala Ile
                85                  90                  95

Ser Ile Ser Phe Trp Pro Gln Thr Thr Thr Thr Pro Thr Ser Val Asp
                100                 105                 110

Met Asn Ser Ile Thr Ser Thr Asp Val Arg Ile Leu Val Gln Pro Gly
            115                 120                 125

Ile Ala Ser Glu Leu Val Ile Pro Ser Glu Arg Leu His Tyr Arg Asn
        130                 135                 140

Gln Gly Trp Arg Ser Val Glu Thr Ser Gly Val Ala Glu Glu Glu Ala
145                 150                 155                 160

Thr Ser Gly Leu Val Met Leu Cys Ile His Gly Ser Pro Val Asn Ser
                165                 170                 175

Tyr Thr Asn Thr Pro Tyr Thr Gly Ala Leu Gly Leu Leu Asp Phe Ala
                180                 185                 190

Leu Glu Leu Glu Phe Arg Asn Leu Thr Thr Cys Asn Thr Asn Thr Arg
            195                 200                 205

Val Ser Arg Tyr Ser Ser Thr Ala Arg His Arg Leu Arg Arg Gly Ala
        210                 215                 220

Asp Gly Thr Ala Glu Leu Thr Thr Thr Ala Ala Thr Arg Phe Met Lys
225                 230                 235                 240

Asp Leu His Phe Thr Gly Leu Asn Gly Val Gly Glu Val Gly Arg Gly
                245                 250                 255

Ile Ala Leu Thr Leu Leu Asn Leu Ala Asp Thr Leu Leu Gly Gly Leu
                260                 265                 270

Pro Thr Glu Leu Ile Ser Ser Ala Gly Gly Gln Leu Phe Tyr Ser Arg
            275                 280                 285

Pro Val Val Ser Ala Asn Gly Glu Pro Thr Val Lys Leu Tyr Thr Ser
        290                 295                 300

Val Glu Asn Ala Gln Gln Asp Lys Gly Val Ala Ile Pro His Asp Ile
305                 310                 315                 320

Asp Leu Gly Asp Ser Arg Val Val Ile Gln Asp Tyr Asp Asn Gln His
                325                 330                 335

Glu Gln Asp Arg Pro Thr Pro Ser Pro Ala Pro Ser Arg Pro Phe Ser
                340                 345                 350

Val Leu Arg Ala Asn Asp Val Leu Trp Leu Ser Leu Thr Ala Ala Glu
            355                 360                 365

Tyr Asp Gln Ser Thr Tyr Gly Ser Ser Thr Gly Pro Val Tyr Ile Ser
```

-continued

```
              370                 375                 380
Asp Ser Val Thr Leu Val Asn Val Ala Thr Gly Ala Gln Ala Val Ala
385                 390                 395                 400
Arg Ser Leu Asp Trp Ser Lys Val Thr Leu Asp Gly Arg Pro Leu Pro
                    405                 410                 415
Thr Val Glu Gln Tyr Ser Lys Thr Phe Phe Val Leu Pro Leu Arg Gly
                420                 425                 430
Lys Leu Ser Phe Trp Glu Ala Gly Thr Thr Lys Ala Gly Tyr Pro Tyr
                435                 440                 445
Asn Tyr Asn Thr Thr Ala Ser Asp Gln Ile Leu Ile Glu Asn Ala Ala
            450                 455                 460
Gly His Arg Val Ala Ile Ser Thr Tyr Thr Thr Arg Leu Gly Ala Gly
465                 470                 475                 480
Pro Val Ala Ile Ser Ala Ala Val Leu Ala Pro Arg Ser Ala Leu
                    485                 490                 495
Ala Leu Leu Glu Asp Thr Phe Asp Tyr Pro Gly Arg Ala His Thr Phe
                500                 505                 510
Asp Asp Phe Cys Pro Glu Cys Arg Ala Leu Gly Leu Gln Gly Cys Ala
                515                 520                 525
Phe Gln Ser Thr Val Ala Glu Leu Gln Arg Leu Lys
                530                 535                 540
```

(2) INFORMATION FOR SEQ ID NO:27:

(i) SEQUENCE CHARACTERISTICS:
        (A) LENGTH: 525 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E virus (Burma strain)
            r62kDa, 56.5 kDa (xi) SEQUENCE DESCRIPTION: SEQ ID NO:27:

```
Ala Val Ala Pro Ala His Asp Thr Pro Pro Val Pro Asp Val Asp Ser
1                   5                   10                  15
Arg Gly Ala Ile Leu Arg Arg Gln Tyr Asn Leu Ser Thr Ser Pro Leu
                    20                  25                  30
Thr Ser Ser Val Ala Thr Gly Thr Asn Leu Val Leu Tyr Ala Ala Pro
                    35                  40                  45
Leu Ser Pro Leu Leu Pro Leu Gln Asp Gly Thr Asn Thr His Ile Met
            50                  55                  60
Ala Thr Glu Ala Ser Asn Tyr Ala Gln Tyr Arg Val Ala Arg Ala Thr
65                  70                  75                  80
Ile Arg Tyr Arg Pro Leu Val Pro Asn Ala Val Gly Gly Tyr Ala Ile
                    85                  90                  95
Ser Ile Ser Phe Trp Pro Gln Thr Thr Thr Thr Pro Thr Ser Val Asp
                    100                 105                 110
Met Asn Ser Ile Thr Ser Thr Asp Val Arg Ile Leu Val Gln Pro Gly
                    115                 120                 125
Ile Ala Ser Glu Leu Val Ile Pro Ser Glu Arg Leu His Tyr Arg Asn
            130                 135                 140
Gln Gly Trp Arg Ser Val Glu Thr Ser Gly Val Ala Glu Glu Glu Ala
```

```
145                 150                 155                 160
Thr Ser Gly Leu Val Met Leu Cys Ile His Gly Ser Leu Val Asn Ser
                165                 170                 175
Tyr Thr Asn Thr Pro Tyr Thr Gly Ala Leu Gly Leu Leu Asp Phe Ala
                180                 185                 190
Leu Glu Leu Glu Phe Arg Asn Leu Thr Pro Gly Asn Thr Asn Thr Arg
                195                 200                 205
Val Ser Arg Tyr Ser Ser Thr Ala Arg His Arg Leu Arg Arg Gly Ala
                210                 215                 220
Asp Gly Thr Ala Glu Leu Thr Thr Ala Ala Thr Arg Phe Met Lys
225                 230                 235                 240
Asp Leu Tyr Phe Thr Ser Thr Asn Gly Val Gly Glu Ile Gly Arg Gly
                245                 250                 255
Ile Ala Leu Thr Leu Phe Asn Leu Ala Asp Thr Leu Leu Gly Gly Leu
                260                 265                 270
Pro Thr Glu Leu Ile Ser Ser Ala Gly Gly Gln Leu Phe Tyr Ser Arg
                275                 280                 285
Pro Val Val Ser Ala Asn Gly Glu Pro Thr Val Lys Leu Tyr Thr Ser
                290                 295                 300
Val Glu Asn Ala Gln Gln Asp Lys Gly Ile Ala Ile Pro His Asp Ile
305                 310                 315                 320
Asp Leu Gly Glu Ser Arg Val Val Ile Gln Asp Tyr Asp Asn Gln His
                325                 330                 335
Glu Gln Asp Arg Pro Thr Pro Ser Pro Ala Pro Ser Arg Pro Phe Ser
                340                 345                 350
Val Leu Arg Ala Asn Asp Val Leu Trp Leu Ser Leu Thr Ala Ala Glu
                355                 360                 365
Tyr Asp Gln Ser Thr Tyr Gly Ser Ser Thr Gly Pro Val Tyr Val Ser
                370                 375                 380
Asp Ser Val Thr Leu Val Asn Val Ala Thr Gly Ala Gln Ala Val Ala
385                 390                 395                 400
Arg Ser Leu Asp Trp Thr Lys Val Thr Leu Asp Gly Arg Pro Leu Ser
                405                 410                 415
Thr Ile Gln Gln Tyr Ser Lys Thr Phe Phe Val Leu Pro Leu Arg Gly
                420                 425                 430
Lys Leu Ser Phe Trp Glu Ala Gly Thr Thr Lys Ala Gly Tyr Pro Tyr
                435                 440                 445
Asn Tyr Asn Thr Thr Ala Ser Asp Gln Leu Leu Val Glu Asn Ala Ala
                450                 455                 460
Gly His Arg Val Ala Ile Ser Thr Tyr Thr Thr Ser Leu Gly Ala Gly
465                 470                 475                 480
Pro Val Ser Ile Ser Ala Val Ala Val Leu Ala Pro His Ser Ala Leu
                485                 490                 495
Ala Leu Leu Glu Asp Thr Leu Asp Tyr Pro Ala Arg Ala His Thr Phe
                500                 505                 510
Asp Asp Phe Cys Pro Glu Cys Arg Pro Leu Gly Leu Gln
                515                 520                 525

(2) INFORMATION FOR SEQ ID NO:28:

(i) SEQUENCE CHARACTERISTICS:
        (A) LENGTH: 525 amino acids
        (B) TYPE: amino acid
        (C) STRANDEDNESS: single
        (D) TOPOLOGY: linear
```

```
    (ii) MOLECULE TYPE: protein (iii) HYPOTHETICAL: NO (vi) ORIGINAL SOURCE:
         (C) INDIVIDUAL ISOLATE: Hepatitis E virus (Mexico strain)
             r62kDa, 56.5 kDa (xi) SEQUENCE DESCRIPTION: SEQ ID NO:28:

Ala Val Ala Pro Ala His Asp Thr Ser Pro Val Pro Asp Val As

```
Tyr Asp Gln Ser Thr Tyr Gly Ser Ser Thr Gly Pro Val Tyr Ile Ser
    370                 375                 380

Asp Ser Val Thr Leu Val Asn Val Ala Thr Gly Ala Gln Ala Val Ala
385                 390                 395                 400

Arg Ser Leu Asp Trp Ser Lys Val Thr Leu Asp Gly Arg Pro Leu Pro
                405                 410                 415

Thr Val Glu Gln Tyr Ser Lys Thr Phe Phe Val Leu Pro Leu Arg Gly
            420                 425                 430

Lys Leu Ser Phe Trp Glu Ala Gly Thr Thr Lys Ala Gly Tyr Pro Tyr
        435                 440                 445

Asn Tyr Asn Thr Thr Ala Ser Asp Gln Ile Leu Ile Glu Asn Ala Ala
    450                 455                 460

Gly His Arg Val Ala Ile Ser Thr Tyr Thr Thr Arg Leu Gly Ala Gly
465                 470                 475                 480

Pro Val Ala Ile Ser Ala Ala Ala Val Leu Ala Pro Arg Ser Ala Leu
                485                 490                 495

Ala Leu Leu Glu Asp Thr Phe Asp Tyr Pro Gly Arg Ala His Thr Phe
            500                 505                 510

Asp Asp Phe Cys Pro Glu Cys Arg Ala Leu Gly Leu Gln
        515                 520                 525

(2) INFORMATION FOR SEQ ID NO:29:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (iii) HYPOTHETICAL: NO (vi) ORIGINAL SOURCE:
        (C) INDIVIDUAL ISOLATE: HEV 5' primer (xi) SEQUENCE DESCRIPTION: SEQ ID NO:29:

GGGGGGGATC CATATGGCGG TCGCTCCGGC CCATGACACC CCG                    43

(2) INFORMATION FOR SEQ ID NO:30:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (vi) ORIGINAL SOURCE:
        (C) INDIVIDUAL ISOLATE: HEV 3' primer (xi) SEQUENCE DESCRIPTION: SEQ ID NO:30:

ATTAGAAGCT TCCGTGGCCA TTATATG                                      27

(2) INFORMATION FOR SEQ ID NO:31:

(i) SEQUENCE CHARACTERISTICS:
        (A) LENGTH: 33 amino acids
        (B) TYPE: amino acid
        (D) TOPOLOGY: linear
```

```
    (ii) MOLECULE TYPE: protein (iii) HYPOTHETICAL: YES (iv) ANTI-SENSE: NO (v) FRAGMENT TYPE: internal (vi) ORIGINAL SOURCE:
          (C) INDIVIDUAL ISOLATE: internally consistent sequence of
              two HEV 406.4-2 antigens (ix) FEATURE:
          (A) NAME/KEY: Modified-site
          (B) LOCATION: 3
          (D) OTHER INFORMATION: /note= "where Xaa is Q or P"

(ix) FEATURE:
          (A) NAME/KEY: Modified-site
          (B) LOCATION: 5
          (D) OTHER INFORMATION: /note= "where Xaa is G or D"

(ix) FEATURE:
          (A) NAME/KEY: Modified-site
          (B) LOCATION: 7
          (D) OTHER INFORMATION: /note= "where Xaa is L or S"

(ix) FEATURE:
          (A) NAME/KEY: Modified-site
          (B) LOCATION: 12
          (D) OTHER INFORMATION: /note= "where Xaa is E or V"

(ix) FEATURE:
          (A) NAME/KEY: Modified-site
          (B) LOCATION: 13
          (D) OTHER INFORMATION: /note= "where Xaa is I or T"

(ix) FEATURE:
          (A) NAME/KEY: Modified-site
          (B) LOCATION: 22
          (D) OTHER INFORMATION: /note= "where Xaa is P or H"

(ix) FEATURE:
          (A) NAME/KEY: Modified-site
          (B) LOCATION: 24
          (D) OTHER INFORMATION: /note= "where Xaa is A or V"

(ix) FEATURE:
          (A) NAME/KEY: Modified-site
          (B) LOCATION: 29
          (D) OTHER INFORMATION: /note= "where Xaa is P or L"

(ix) FEATURE:
          (A) NAME/KEY: Modified-site
          (B) LOCATION: 31
          (D) OTHER INFORMATION: /note= "where Xaa is L or P"

(xi) SEQUENCE DESCRIPTION: SEQ ID NO:31:

Ala Asn Xaa Pro Xaa His Xaa Ala Pro Leu Gly Xaa Xaa Arg Pro Ser
1               5                   10                  15

Ala Pro Pro Leu Pro Xaa Val Xaa Asp Leu Pro Gln Xaa Gly Xaa Arg
            20                  25                  30

Arg
```